(12) United States Patent
Moreadith et al.

(10) Patent No.: US 6,632,934 B1
(45) Date of Patent: Oct. 14, 2003

(54) MORC GENE COMPOSITIONS AND METHODS OF USE

(75) Inventors: Randall W. Moreadith, Chapel Hill, NC (US); Andrew R. Zinn, Dallas, TX (US); Mark L. Watson, Dallas, TX (US); Norimitsu Inoue, Yao (JP); Karl D. Hess, McDade, TX (US); George M. Albright, Irving, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/409,604

(22) Filed: Sep. 30, 1999

Related U.S. Application Data
(60) Provisional application No. 60/102,575, filed on Sep. 30, 1998.

(51) Int. Cl.[7] .............................................. C07H 21/04
(52) U.S. Cl. ..................................................... 536/23.1
(58) Field of Search ............................... 536/23.5, 23.1; 435/320.1, 325, 69.1, 6, 7.1, 7.21

(56) References Cited

PUBLICATIONS

Bork et al., Genome Research, pp. 398–400, 2000.*
Bowie et al., Science vol. 247, pp. 1306–1310, Mar. 1990.*
Burgess et al., The Journal of Cell Biology, vol. 111, pp. 2129–2138, 1990.*
Lazar et al., Molecular and Cellular Biology, vol. 8, No. 3, pp. 1247–1252, Mar. 1988.*
Harris et al (J. Am Soc. Nephr, 1995, 6:1125–1133).*
Ahn et al (Nature Genetics, 1993, 3(4):283–291).*
Cawthon et al (Genomics, 1991, 9(3):446–460).*
Boehringer Mannheim Biochemicals, 1994, Catalog, p. 93.*
Cattanach et al., "Sex–reversed mice: XX and XO males," *Cytogenetics*, 10(5):318–337, 1971.
Hummel, "New linkages," *Mouse News Letter*, 34:31–32, 1966.
Inoue et al., "New gene family defined by MORC, a nuclear protein required for mouse spermatogenesis," *Human Molecular Genetics*, 8:1201–1207, 1999.
Nagase et al. "Prediction of the coding sequences of unidentified human genes IV. The coding sequences of 40 new genes (KIAA0121–KIAA0160) deduced by analysis of cDNA clones from Human cell line KG–1", *DNA Res.*, 2(4):167–174, 1995.
Okabe, Ikawa, Ashkenas, "Male infertility and the genetics of spermatogenesis," *Am. J. Hum. Genet.*, 62(6):1274–1281, 1998.
Watson et al., "Identification of morc (microrchidia), a mutation that results in arrest of spermatogenesis at an early meiotic stage in the mouse." *Proc Natl Acad Sci USA*, (24):14361–6, 1995. Abstract.

* cited by examiner

*Primary Examiner*—Susan Ungar
(74) *Attorney, Agent, or Firm*—Fulbright & Jaworski L.L.P.

(57) ABSTRACT

Disclosed are compositions and methods comprising a novel mammalian gene, designated MORC, that is expressed in male germ cells. Also disclosed are polynucleotide compositions comprising a MORC gene from human and murine sources, and polypeptides encoded by these nucleic acid sequences. Methods for preparing MORC polypeptides, transformed host cells, and antibodies reactive with MORC polypeptides are also provided. In certain embodiments, the invention describes methods for diagnosing and treating infertility or testicular cancer, as well as methods for identifying MORC-related polynucleotide and polypeptide compositions.

2 Claims, 8 Drawing Sheets

Figure 10:
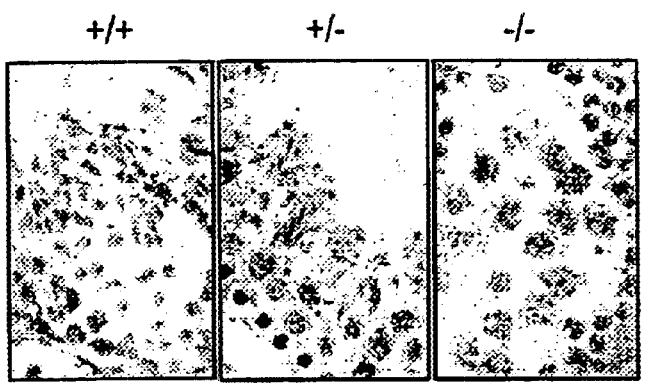

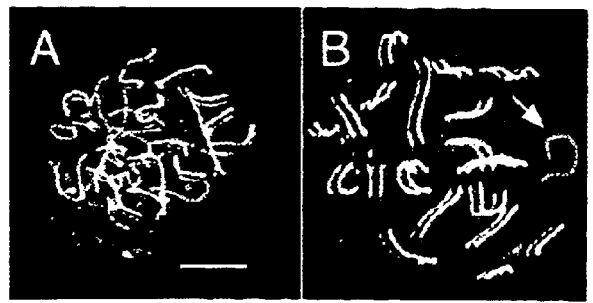
FIG. 3A  FIG. 3B
FIG. 3C  FIG. 3D
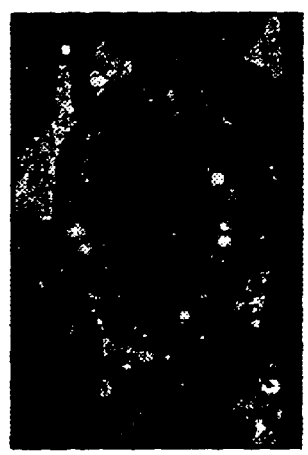 
FIG. 4A  FIG. 4B 10 day old +/- testes 10 day old -/- testes 24 day old +/- testes 24 day old -/- testes

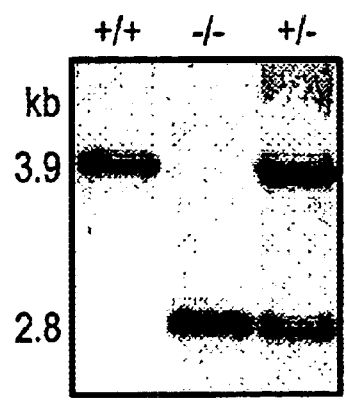 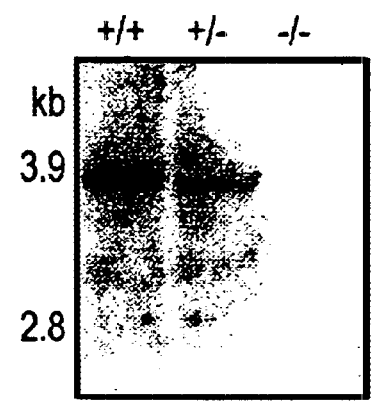
FIG. 12A   FIG. 12B
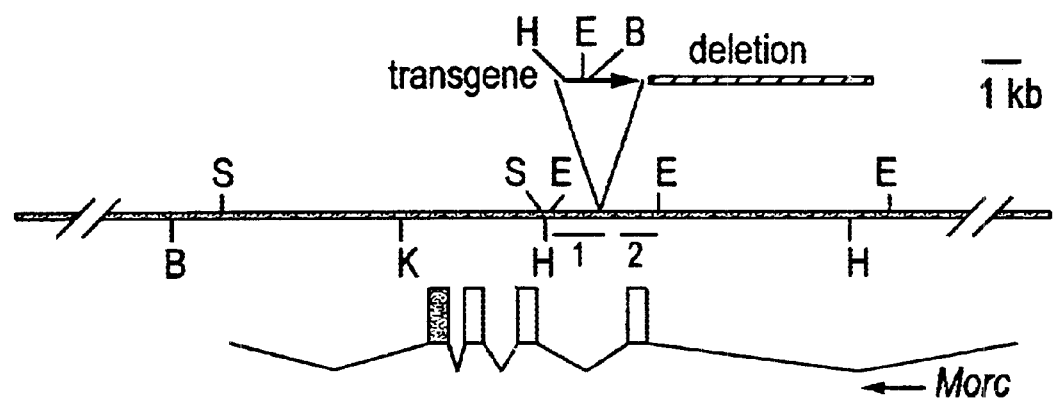
FIG. 13
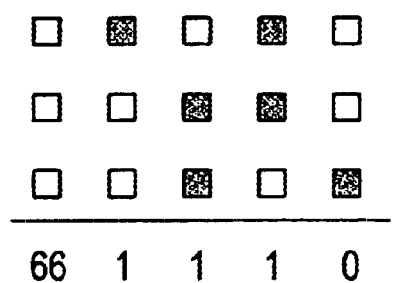
FIG. 14

MORC GENE COMPOSITIONS AND METHODS OF USE

This application claims priority to provisional U.S. Application Serial No. 60/102,575, filed on Sep. 30, 1998, now abandoned.

The United States government has rights in the present invention pursuant to Grant Number HD31376 from the National Institutes of Health.

1.0 BACKGROUND OF THE INVENTION

1.1 Field of the Invention

The present invention relates generally to the field of molecular biology. More particularly, it concerns nucleic acid segments isolated from human and murine sources, which encode a male germ cell specific protein, designated MORC. Various methods for making and using MORC DNA segments, DNA segments encoding synthetically-modified MORC proteins, and native and synthetic MORC polypeptides are disclosed, such as, for example, the use of DNA segments as diagnostic probes and templates for protein production, and the use of proteins, fusion protein carriers and peptides in various immunological and diagnostic applications. Also disclosed are methods for identifying MORC-related polynucleotides and polypeptides, and methods for diagnosing and treating infertility or cancer, and in particular, testicular cancer, as well as screening methods for compounds that are involved with the development of cancer or spermatogenesis.

1.2 Description of Related Art

The genetic control of spermatogenesis is complex (Sassone-Corsi, 1997). Mutations at multiple loci and in structurally and functionally disparate genes in the mouse genome affect gametogenesis (Handel, 1987). Most mutations are pleiotropic, causing multi-system pathologies rather than isolated spermatogenic abnormalities. For example, the autosomal recessive mutation weaver, which results in degeneration of germ cells, also causes loss of the cerebellar granular cell layer and ataxia in affected mice (Vogelweid et al., 1993). The histologic phenotypes of mutations that affect germ cells are varied and include both reduced cell numbers and abnormal cell morphologies. Further complicating the understanding of germ cell biology is the fact that genes known to be essential for spermatogenesis participate in multiple cellular processes, including transcriptional control (Nantel et al., 1996; Blendy et al., 1996), cell proliferation (Toscani et al., 1997), protein folding (Dix et al., 1996) and DNA repair (Baker et al., 1995; Donehower et al., 1992).

1.2.1 Genetic Control of Mouse Spermatogenesis

The genetic control of mouse spermatogenesis has been extensively reviewed in the literature (Handel, 1987). Briefly, spermatogenesis is a complex and highly ordered developmental process, lasting 36 days in mice. Three phases of spermatogenesis can be distinguished: mitotic proliferation and renewal of spermatogonia, or stem cells; meiotic reduction division of spermatocytes; and differentiation of haploid spermatids into mature sperm cells, or spermiogenesis. The first meiotic division in protracted, with cells remaining in pachytene stage for 11 days. During this time, homologous chromosomes pair and recombine, and there is extensive DNA repair synthesis and transcription. Many genes must act during this stage of spermatogenesis, and it is the target of a number of mutations.

1.2.2 Mouse Spermatogenesis Mutations

A large number of spontaneous and induced mouse mutations resulting in abnormalities of normal spermatogenesis and fertility have been identified (Table 1). Recent reviews cataloging these mutations demonstrate the genetic heterogeneity and phenotypic pleiotropy of infertility (Handel, 1987; Chugg, 1989; Simoni, 1994; Wilmut et al., 1991). Mutations can be divided into three general groups. Pretesticular phenotypes are the result of pituitary abnormalities or improper embryogenesis and germ cell migration (e.g., gcd). Intratesticular phenotypes result from mutations which manifest as abnormalities of the germ cells themselves (spermatogonia, spermatocytes, spermatids) (e.g., dazla). Post-testicular phenotypes encompass mutations that produce spermatozoa with abnormal function (e.g., hotfoot).

The majority of the mutations in Table 1 are pleiotropic, causing multisystem pathologies rather than isolated abnormalities involving spermatogenesis. For example, the autosomal recessive mutation sks (skeletal fusions with sterility) results in arrest of germ cell development at late meiotic prophase but also causes skeletal fusions of vertebrae and ribs, resulting in body shortening and tail kinks (Vogelweid et al., 1939). In many of these mutations, the effects on germ cells are broad and include both reduced cell numbers and abnormal cell morphologies. The genes associated with infertility have various and sundry functions and include metabolic proteins (ornithine decarboxylase), heat shock proteins/molecular chaperones proteins (Hsp70-2), transcriptional activators (CREM), and proteins involved in DNA repair and maintenance of genome stability, such as the DNA mismatch repair homologue pms2 and the p53 gene (Baker et al., 1995; Donehower et al., 1992).

1.2.3 Spermatogenesis and DNA Repair Mutations

Some of the best characterized genes required for spermatogenesis are those involved in DNA repair. DNA repair defects that delay or prevent the completion of meiotic recombination lead to disruption of the meiotic process (Baker et al., 1995; Arnheim and Shibata, 1997; Edelmann et al., 1996; Hawley and Friend, 1996; Kolodner, 1995; McKee, 1996; Modrich and Lahue, 1996; Rose and Holm, 1993), typically resulting in arrest at the pachytene stage. Factors have been identified which are exclusively required for meiotic events and others which play roles in both mitotic and meiotic cells. Topoisomerase II conditional mutants are one example of the latter. These mutants exhibit both enhanced mitotic recombination and meiotic pachytene arrest (Rose and Holm, 1993). A number of recent reviews have described how eukaryotes maintain chromosome integrity in meiotic cells through DNA repair (Kleckner, 1996; Stahl, 1996; Roeder, 1997). Meiotic cells seem to have developed mechanisms functionally equivalent to mitotic cell cycle checkpoints to sense DNA strand breaks and prevent cells from progressing through the cell cycle until DNA damage is resolved. In yeast it has been shown that several of the proteins involved in mitotic DNA strand-break cell cycle checkpoints (Rad17, Rad 24 and Mec1) are necessary for preventing cells from progressing into meiotic division I before recombination is complete (Handel, 1987). Based on these and similar observations, it has been proposed that the meiotic cell cycle is an evolutionary product of mitosis, with diploidy and strand break-sensing checkpoint mechanisms serving to ensure the integrity of the genome (Kleckner, 1996).

An interesting feature of mice missing various DNA repair components is that many targeted mutations that disrupt normal DNA repair and genome stability genes also have profound effects on germ cell development and spermatogenesis (Arnheim and Shibata, 1997)(Table 2). Some of these mutations involve defects in gametogenesis in both sexes (for example the mlh1 and Atm−/−mice), while deficiencies in other genes cause male germ cell arrest specifically (pms2−/−mice). Clearly male and female gametogenesis are biologically different processes although the molecular basis for the difference is not known.

TABLE 1

MOUSE SPERMATOGENESIS MUTATIONS

| Locust[a] | Type[b] | Female Fertile? | Germ Cell Phenotype | Other Phenotype | Ref |
|---|---|---|---|---|---|
| A-myb | KO | Yes | Lack of spermatids, post meiotic cells, degeneration of primary spermatocytes, apoptosis. | Mammary proliferation defective | [1] |
| Bax (Bcl-2 partner) | KO | No | Multinucleate giant cell, cell death, no mature spermatids | Lymphoid hyperplasia | [4] |
| bs (blind sterile) | AR | Yes | Acrosome absent in spermatids | bilenticular cataracts | [12] |
| c (albino) | AR | Yes | Reduced spermatids, abnormal sperm in epidydimis | pigmentation loss | [13] |
| CREM (cyclic AMP response element modulator | KO | Yes | Heterozygotes- reduced fertility. Homozygotes- apoptosis, absence of spermatids/spermatozoa | Runting | [2, 14] |
| dazla | KO | No | Azoospermia, depletion of germ cells after mitotic proliferation | None identified. | [15] |
| desert hedgehog | KO | Yes | Few spermatids on 129-C57BL/6J background, primary spermatocyte degeneration on 129 | None identified. | [16] |
| gcd (germ cell deficient) | TKO | No | Depletion of germ cells by dpc 11.5 | None identified | [17] |
| H-ras-MMTV | TR | Yes | Normal sperm count, 10% of sperm with normal motility | Mammary/salivary gland tumors | [18] |
| ho (hotfoot) | TKO/AR | Subfertile | Sperm unable to penetrate zona pellucida | motor disorders | [19] |
| inhibin | KO | No | Initial normal spermatogenesis, then regression with gonadal stromal tumors | Gonadal stromal tumors | [20] |
| jcd (juvenile spermatagonial depletion) | AR | Yes | azoospermia, single wave of spermatogenesis with degeneration | None identified. | [21] |
| kit receptor/ligand | AR | No | Primordial germ cell development | Defects in melanogenesis, hematopoiesis | [22] |
| Lvs (lacking vigorous sperm) | AD, TR | Yes | HCK protooncogene transgenic, abnormal spermatids | None identified | [23] |
| Mshi | AR | Yes | Disorganized seminiferous epithelium, reduced spermatogonia. | Rejection of skin grafts from syngeneic, sex-matched mice. | [24] |
| Hsp70-2 | KO | Yes | No postmeiotic spermatids/mature sperm, synaptonemal complex abnormal | None identified. | [3] |
| pcd (Purkinje cell degeneration | AR | Yes | Few sperm, most abnormal with vacuolization | Ataxia, degeneration of Purkinje cells at day 15 | [25] |
| sys (symplastic spermatids) | TKO | Yes | azoospermia, Syncytia of spermatids, Sertoli cell vacuolization, | None identified. | [26] |
| t haplotypes | complex | Yes | Transmission ratio distortion | tailess with T/T genotype | [27, 28] |
| wv (weaver) | AR | Yes | Rare elongating spermatids, germ cell degeneration | Ataxia, hyperreflexability, loss of cerebellar granular layer | [9] |

[a]spontaneous, transgenic and knockout loci are listed together, see column 2 for designation.
[b]AR autosomal recessive, AD autosomal dominant, TR Transgenic, TKO Transgene knockout, KO, targeted homologous recombination.

TABLE 2

DNA REPAIR AND GENOME STABILITY GENES INACTIVATED BY TARGETED HOMOLOGOUS RECOMBINATION

| Gene | Human Homolog | Mouse Cancers | Females Fertile? | Male Infertility Phenotype | Ref |
|---|---|---|---|---|---|
| p53 | Li-Fraumeni | Lymphoma, hemangiosarcoma, osteosarcoma, sarcoma | Yes | Reduced male fertility in pCAT/p53 transgenics with 129 strain background | (Donehower et al., 1992) |
| pms2 (mutL homologue) | HNPCC, also endometrial, ovarian, stomach | Lymphoma, cervical sarcoma | Yes | Abnormal spermatozoa. Misshapen spermatids, Primary spermatocyes with vacuolization. Frequent asynapsis. | (Baker et al., 1995) |
| MLH1 (mutL homologuel) | HNPCC | None RER + phenotype | No (No meiosis II) | Meiosis I arrest Small testes, | (Edelmann et al., 1996) |

TABLE 2-continued

DNA REPAIR AND GENOME STABILITY GENES INACTIVATED BY TARGETED HOMOLOGOUS RECOMBINATION

| Gene | Human Homolog | Mouse Cancers | Females Fertile? | Male Infertility Phenotype | Ref |
|---|---|---|---|---|---|
| ATM | Ataxia Telangectasia (lymphoretic CA) | Thymic lymphoblastic lymphomas | No, estrous | Disrupted spermatogenesis | (Barlow et al., 1996) |

1.2.4 Drosophila Spermatogenesis Genes

Many insights into germ cell development have come from utilizing *Drosophila melanogaster* and *Drosophila hydei* as model systems. Drosophila has a number of advantages over other organisms for studies of germ cells, including the ease of generating large numbers of new mutants tagged with selectable transposable elements, well defined developmental germ cell stages (Lindsley and Tokuyasu, 1980) with characterized mutants at each stage, and a small genome with few chromosomes to simplify genetic and cytogenetic analyses. These advantages have led to the generation of a significant number of mutants that interrupt gametogenesis at various stages (Maines and Wasserman, 1998; Williamson and Lehmann, 1996).

Analysis of several Drosophila spermatogenesis mutants has defined stage specific defects that can be grouped into proliferative, growth phase, meiotic and postmeiotic mutants (Castrillon et al., 1993). Several mutants interrupt spermatogenesis at the mitotic to meiotic transition.

The twine mutant affects a cell cycle cdc2 homologue that is expressed specifically in germ cells (Alphey et al., 1992; Courtot et al., 1992). Twine arrests development at the 16 cell stage in spermatocyte cysts, but interestingly, some spermatid cell differentiation continues in these tetraploid cells. Twine seems to be involved in preparation of chromosomes in both males and females for the two meiotic reduction divisions (Eberhart and Wasserman, 1995; White-Cooper et al., 1993). Two other mutants, pelota and boule, were identified in a screen for viable male sterile mutations. Like twine, pelota arrests the meiotic reduction process but allows some differentiation to proceed, albeit aberrant (Castrillon et al., 1993; Eberhart and Wasserman, 1995). Boule has a similar phenotype to pelota (Eberhart et al., 1996), but is unique in that its expression is testes specific (Shan et al., 1996), and it has a human homologue, DAZ, which is frequently deleted in azoospermic men (Reijo et al., 1995; Simoni et al., 1997).

Four separate spermatogenesis mutants: always early, cannonball, meiosis I arrest and spermatocyte arrest have also been identified. These mutations are unique in that they arrest both spermatogenesis at the mitotic to meiotic transition and also block postmeiotic differentiation, in contrast to twine, pelota and boule (Lin et al., 1996). Mutations at the bocce locus produce cysts that have primary spermatocytes in variable number. However progression to meiotic cysts is generally arrested, with only rare postmeiotic cysts present (Castrillon et al., 1993).

There are several significant differences between Drosophila and mammalian spermatogenesis. These differences include: 1) the absence of meiotic recombination in Drosophila males, 2) the ability of Drosophila germ cells to progress through spermatogenesis despite the cessation of transcription at entry into meiosis (Brink, 1968), 3) the presence of apbptosis during normal germ cell differentiation in rodents and humans, and 4) the protracted duration of mammalian meiosis. Teleologically, these differences may serve to limit the number of defective gametes in mammals, in whom small numbers of progeny may impose strong selection against production of zygotes with DNA mutations or chromosomal abnormalities.

1.3 Deficiencies in the Prior Art

There remains a need in the art for polynucleotide and polypeptide compositions useful in the diagnosis and treatment of male infertility, defects in spermatogenesis, and in the detection and treatment of male cancers, and in particular, testicular cancer and related disorders. The identification and characterization of male germ cell specific nucleic acid and amino acid compositions that are involved in spermatogenesis, particularly in the progression through meiosis, would represent a significant advance in the art.

2.0 SUMMARY OF THE INVENTION

The present invention overcomes these and other limitations in the prior art by providing a novel male germ cell polypeptide (designated MORC) and the gene which encodes it (designated MORC). The gene encoding the murine MORC polypeptide is given in SEQ ID NO:1, with the corresponding murine MORC polypeptide shown in SEQ ID NO:2. The gene encoding the human MORC polypeptide is given in SEQ ID NO:3, with the corresponding human MORC polypeptide shown in SEQ ID NO:4.

The present invention provides an isolated nucleic acid segment comprising a gene encoding a MORC polypeptide, wherein the MORC polypeptide comprises a contiguous amino acid sequence of at least 27 amino acids SEQ ID NO:2 or SEQ ID NO:4. In certain preferred embodiments, the MORC polypeptide comprises the contiguous amino acid sequence of SEQ ID NO:2 or SEQ ID NO:4.

In particular aspects, the gene comprises the nucleic acid sequence from position 105 to position 2954 of SEQ ID NO:1, or the nucleic acid sequence from position 63 to position 3014 of SEQ ID NO:3, or a complement thereof, or a sequence that hybridizes to the sequence from position 105 to position 2954 of SEQ ID NO:1, or the nucleic acid sequence from position 63 to position 3014 of SEQ ID NO:3, under conditions of high stringency.

In preferred embodiments of the invention, the nucleic acid segment is isolated from a mammalian cell, including, but not limited to, a rodent cell, such as a mouse or a rat cell, or in particularly preferred aspects, a human cell.

In further aspects of the invention, the nucleic acid segment is operably linked to a promoter that directs the expression of the nucleic acid segment in a host cell. In certain aspects, the promoter is a heterologous promoter.

In other preferred embodiments of the present invention, the isolated nucleic acid segment is comprised within a recombinant vector. Exemplary recombinant vectors include, but are not limited to, artificial chromosome vectors such as bacterial artificial chromosomes and yeast artificial chromosomes, viral vectors such as adenoviral, adeno-associated viral, retroviral, herpes viral, vaccinia viral or baculoviral vectors, plasmids, cosmids and phagemids.

The present invention also provides an isolated nucleic acid segment characterized as an isolated nucleic acid segment comprising a sequence region that consists of at least 23 contiguous nucleotides that have the same sequence as, or are complementary to, at least 23 contiguous nucleotides of SEQ ID NO:1 or SEQ ID NO:3; or an isolated nucleic acid segment of from 23 to about 20,000 nucleotides in length that hybridizes to the nucleic acid segment of SEQ ID NO:1 or SEQ ID NO:3; or the complement thereof, under stringent hybridization conditions.

In certain aspects of the invention, the nucleic acid segment comprises a sequence region of at least 30 nucleotides, at least 50 nucleotides, at least 100 nucleotides, at least 250 nucleotides, at least 500 nucleotides, at least 1000 nucleotides, at least 2000 nucleotides or at least 2500 nucleotides, or the nucleic acid segment is 30, 50, 100, 250, 500, 1000, 2000 or 2500 nucleotides in length. In particular aspects, the nucleic acid segment comprises the sequence of SEQ ID NO:1 or SEQ ID NO:3. In other aspects of the invention, the nucleic acid is up to 10,000, up to 5,000 or up to 3,000 base pairs in length.

A further objective of the invention is to provide polynucleotide segments comprising all or parts of a gene encoding MORC. Polynucleotide probes and primers specific for these MORC. genes also represent important compositions provided by the invention.

The present invention further provides a recombinant host cell comprising an isolated nucleic acid segment comprising a gene encoding a MORC polypeptide, wherein the MORC polypeptide comprises a contiguous amino acid sequence of at least 27 amino acids SEQ ID NO:2 or SEQ ID NO:4. In preferred aspects, the recombinant host cell is further defined as a prokaryotic cell, such as a bacterial cell or, more particularly, an *E. coli* cell. In other preferred aspects, the recombinant host cell is further defined as a eukaryotic cell, such as an animal cell or a fungal cell. In particularly preferred embodiments, the animal cell is a mammalian cell, exemplified by, but not limited to, a human, mouse, rat, monkey, chicken, dog, cat, horse, pig, cow, sheep, goat or hamster cell. In still other preferred aspects, the mammalian cell is a tumor cell, such as a testicular cancer cell.

In further embodiments, the isolated nucleic acid segment is introduced into the cell by a recombinant vector, wherein the host cell expresses the isolated nucleic acid segment to produce a MORC peptide or polypeptide. In additional aspects, the MORC peptide or polypeptide comprises a contiguous amino acid sequence of at least about 27 amino acids from SEQ ID NO:2 or SEQ ID NO:4.

Another aspect of the present invention is an animal cell, such as a human or other animal cell, that comprises a MORC polypeptide or polynucleotide. In a preferred embodiment, the cell is a mouse male germ cell that produces a MORC polypeptide of approximately 108-kDa, and that is identical to, or substantially homologous with, the MORC polypeptide identified in SEQ ID NO:2, or a human male germ cell that produces a MORC polypeptide of approximately 118-kDa, and that is identical to, or substantially homologous with, the MORC polypeptide identified in SEQ ID NO:4.

A further aspect of the present invention is a vector (such as a plasmid, cosmid, virus, phagemid, or the like), that includes within its nucleotide sequence a nucleic acid segment that comprises one or more MORC genes, or portions thereof. Preferably such a vector is comprised within a transformed host cell. The transformed host cell may be a bacterial, animal, fungal, or plant cell, and may be comprised within a transgenic animal, or may be comprised within a culture of bacteria, yeast, fungus, animal or plant cells.

Another embodiment of the invention provides polypeptides and peptides comprising at least 26 or more, and preferably, substantially all of the amino acid sequences disclosed in SEQ ID NO:2 and SEQ ID NO:4. Polypeptides having MORC activity represent important compositions provided by the invention. It is a further objective of the invention to provide methods for identifying MORC polypeptide and polynucleotide compositions, methods for producing such compositions, and methods for using these compositions in a variety of diagnostic and therapeutic regimens. The invention also provides methods and compositions for the detection of MORC compositions in biological and clinical samples.

The present invention also provides a method of preparing a MORC peptide or polypeptide, comprising the steps of expressing an isolated nucleic acid segment comprising a MORC gene encoding a MORC polypeptide, wherein the MORC polypeptide comprises a contiguous amino acid sequence of at least 27 amino acids SEQ ID NO:2 or SEQ ID NO:4, the nucleic acid segment operably linked to a promoter, in a host cell, and collecting the MORC peptide or polypeptide so expressed.

Also provided are nucleic acid detection kits comprising, in a suitable container, an isolated nucleic acid segment characterized as an isolated nucleic acid segment comprising a sequence region that consists of at least 23 contiguous nucleotides that have the same sequence as, or are complementary to, at least 23 contiguous nucleotides of SEQ ID NO:1 or SEQ ID NO:3; or an isolated nucleic acid segment of from 23 to about 20,000 nucleotides in length that hybridizes to the nucleic acid segment of SEQ ID NO:1 or SEQ ID NO:3; or the complement thereof, under stringent hybridization conditions, and a detection reagent.

Thus, the present invention provides a method for detecting a nucleic acid sequence encoding a MORC polypeptide, comprising the steps of contacting sample nucleic acids suspected of encoding a MORC polypeptide with at least a first isolated nucleic acid segment comprising a nucleic acid sequence of at least about 23 contiguous nucleotides of from position 105 to position 2954 of SEQ ID NO:1 or from position 63 to position 3014 of SEQ ID NO:3 under conditions effective to allow hybridization of substantially complementary nucleic acids, and detecting the hybridized complementary nucleic acids thus formed, wherein the presence of hybridized complementary nucleic acids is indicative of the presence of a nucleic acid sequence encoding a MORC polypeptide in the sample nucleic acids. In certain aspects, the sample nucleic acids contacted are located within a cell, while in other aspects, the sample nucleic acids are separated from a cell prior to contact. In further aspects, the isolated nucleic acid comprises a detectable label and the complex is detected by detecting the label.

In another embodiment, there is provided a monoclonal antibody that binds immunologically to a male germ cell polypeptide designated as MORC. The antibody may be non-cross reactive with other human polypeptides, or it may bind to non-human MORC, but not to human MORC. The antibody may further comprise a detectable label, such as a fluorescent label, a chemiluminescent label, a radiolabel or an enzyme. Also encompassed are hybridoma cells and cell lines producing such antibodies.

In another embodiment, there is included a polyclonal antisera, antibodies of which bind immunologically to a MORC polypeptide. The antisera may be derived from any animal, but preferably is from an animal other than a human. Preferred antigens for the preparation of such sera include a MORC polypeptide isolated from a human, rat, goat, rabbit, pig, horse, cat, dog, hamster, monkey or other such animal cell line. Preferred hosts for the preparation of a polyclonal antisera specific for MORC include animals such as rabbits, goats, and other such animals.

The invention also provides pharmaceutical compositions which comprise one or more of the MORC compositions disclosed herein. Such compositions may include MORC or MORC-derived polypeptides, polynucleotides, antisense oligonucleotides, ribozymes, antibodies, antisera, antigens, peptide epitopes, protein fusions, peptides and the like.

The present invention also provides a purified polypeptide comprising a sequence region of at least 27, at least 30, at least 35, at least 50, at least 100, at least 200, at least 500 or at least 900 contiguous amino acids from SEQ ID NO:2 or SEQ ID NO:4. In certain aspects of the invention, the purified polypeptide comprises the sequence of SEQ ID NO:2 or SEQ ID NO:4. In these aspects of the invention, the polypeptide may be encoded by the nucleic acid sequence from position 105 to position 2954 of SEQ ID NO:1, or the nucleic acid sequence from position 63 to position 3014 of SEQ ID NO:3. In certain preferred aspects of the invention, the purified polypeptide is operatively linked to a selected amino acid sequence.

Thus, the present invention further provides a fusion protein comprising a purified polypeptide comprising a sequence region of at least 27 contiguous amino acids from SEQ ID NO:2 or SEQ ID NO:4, operatively linked to a selected amino acid sequence. In particular embodiments, the selected amino acid sequence is an antigenic amino acid sequence.

The present invention also provides an antibody that specifically binds to a polypeptide comprising a sequence region of at least 27 contiguous amino acids from SEQ ID NO:2 or SEQ ID NO:4. In preferred embodiments, the antibody is a monoclonal antibody.

The present invention further provides a method for detecting a MORC polypeptide in a biological sample, comprising the steps of contacting a biological sample suspected of containing a MORC polypeptide with at least a first antibody that specifically binds to a MORC peptide or polypeptide, under conditions effective to allow the formation of complexes, and detecting the complexes so formed.

Additionally provided are immunodetection kits comprising, in a suitable container, an antibody that specifically binds to a polypeptide comprising a sequence region of at least 27 contiguous amino acids from SEQ ID NO:2 or SEQ ID NO:4, and an immunodetection reagent.

In still yet a further embodiment, there is provided transgenic mammal in which both copies of the native MORC gene are interrupted or replaced with another gene.

The present invention also provides a transgenic non-human animal having incorporated into its genome a polynucleotide comprising a transgene that encodes a polypeptide comprising a sequence region of at least 27 contiguous amino acids from SEQ ID NO:2 or SEQ ID NO:4.

Also provided is a composition comprising a MORC polypeptide prepared by a process comprising the steps of culturing a host cell comprising a nucleic acid segment encoding a polypeptide comprising the amino acid sequence of SEQ ID NO:2 or SEQ ID NO:4 under conditions effective to produce the polypeptide, and obtaining the MORC polypeptide from the cell.

The invention also provides a method of identifying a male patient having or at risk for developing infertility, comprising determining the amount of a MORC composition present within a biological sample from the male patient, wherein the absence of the MORC composition in comparison to a sample from a normal male subject, is indicative of a male patient having or at risk for developing infertility. The invention also provides a method of treating infertility, comprising administering to a patient in need of infertility treatment a therapeutically effective amount of a MORC composition.

The invention further provides a method of identifying a male patient having or at risk for developing a germ cell cancer, such as testicular cancer, comprising determining the amount of a MORC composition present within a biological sample from the male patient, wherein the absence of the MORC composition in comparison to a sample from a normal male subject, is indicative of a male patient having or at risk for developing a germ cell cancer, such as testicular cancer.

The invention also provides a method of treating a germ cell cancer, such as testicular cancer, comprising administering to a patient in need of treatment a therapeutically effective amount of a MORC composition. The invention further provides a method of treating a subject having cancer comprising administering contacting a cancer cell within the subject with an expression vector comprising a nucleic acid segment encoding an MORC polypeptide under the transcriptional control of a promoter, wherein expression of the MORC polypeptide is at a level effective to confer a therapeutic benefit on the subject. Treatment of any subject with cancer, including humans, is contemplated. Moreover, in another aspect of the invention, methods of treating cancer also include contacting a cancer cell with an anti-cancer agent. Anticancer agents include those agents used in chemotherapy, radiotherapy, immunotherapy, and gene therapy for the treatment of cancer. A combination gene therapy approach is also provided by the present invention. For example, a MORC polypeptide and a 123F2 polypeptide, which interacts with a MORC polypeptide, may be provided simultaneously or sequentially to a cancer cell as a combination therapy.

In other embodiments of the present invention, screening methods to identify compounds that are involved in spermatogenesis or cancer are provided. The MORC polypeptide interacts with a 123F2 polypeptide, and the 123F2 polypeptide relocalizes MORC from the nucleus to the cytoplasm. Such methods concern finding compounds that modulate the interaction between a MORC polypeptide and a 123F2 polypeptide. These compounds would then be implicated in either the cancer process or spermatogenesis.

The present invention also provides a method of treating microrchidia, comprising administering to a patient in need of treatment a therapeutically effective amount of a MORC composition. Further, the present invention provides a method of altering spermatogenesis, comprising administering to a patient in need of spermatogenesis alteration a therapeutically effective amount of a MORC composition. Also, the invention provides a method of male contraception, comprising administering to a male animal in need of contraception a biologically effective amount of a MORC composition.

The foregoing objects of the invention and others that are now readily apparent to those of skill in the art having the benefit of the present disclosure are described more fully in the sections which follow:

2.1 MORC DNA Segments

In one embodiment, the present invention concerns DNA segments, that can be isolated from virtually any source, that are free from total genomic DNA and that encode the whole or a portion of the novel peptide disclosed herein. The murine MORC gene (position 105 to position 2954 of SEQ ID NO:1) encodes a MORC polypeptide having the contiguous amino acid sequence shown in SEQ ID NO:2. The human MORC gene (position 63 to position 3014 of SEQ ID NO:3) encodes a MORC polypeptide having the contiguous amino acid sequence shown in SEQ ID NO:4. The inventors contemplate a variety of MORC DNA segments from the present invention will find particular utility. For example, those segments that encode all or portions of the MORC polypeptide, or subunits, functional domains, and the like of MORC and MORC-related polypeptides, or those segments that comprise one or more MORC promoter or enhancer regions will be useful in a variety of diagnostic, and therapeutic regimens. Such DNA segments may be native DNA segments isolated using molecular biological methods, or alternatively, such segments may be mutagenized segments, or even segments which have been synthesized in vitro either partially or entirely, using chemical synthesis methods that are well-known to those of skill in the art.

As used herein, the term "DNA segment " refers to a DNA molecule that has been isolated free of total genomic DNA of a particular species. Therefore, a DNA segment encoding a MORC polypeptide or peptide refers to a DNA segment that contains a MORC polypeptide-coding sequence yet is isolated away from, or purified free from, total genomic DNA of the species from which the DNA segment is obtained. Included within the term "DNA segment ", are DNA segments comprising one or more entire MORC genes and/or promoter regions, as well as all partial and smaller fragments and subfragments isolatable from such entire gene-comprising segments, and also recombinant vectors (such as plasmids, cosmids, phagemids, phage, viruses, and the like) which comprise one or more of the MORC-specific polynucleotide sequences of the invention.

Similarly, a DNA segment comprising an isolated or purified MORC polypeptide-encoding gene refers to a DNA segment which may include in addition to peptide encoding sequences, certain other elements such as, regulatory sequences, isolated substantially away from other naturally occurring genes or protein-encoding sequences. In this respect, the term "gene " is used for simplicity to refer to a functional protein-, polypeptide- or peptide-encoding unit. As will be understood by those in the art, this functional term includes not only genomic sequences, including extrachromosomal DNA sequences, but also operon sequences and/or engineered gene segments that express, or may be adapted to express, proteins, polypeptides or peptides.

"Isolated substantially away from other coding sequences" means that the gene of interest, in this case, a MORC gene, forms the significant part of the coding region of the DNA segment, and that the DNA segment does not contain large portions of naturally-occurring coding DNA, such as large chromosomal fragments or other functional genes or operon coding regions. Of course, this refers to the DNA segment as originally isolated, and does not exclude genes, recombinant genes, synthetic linkers, or coding regions later added to the segment by the hand of man.

In particular embodiments, the invention concerns isolated DNA segments and recombinant vectors incorporating DNA sequences that encode a MORC polypeptide that includes within its amino acid sequence an at least ten amino acid contiguous sequence from SEQ ID NO:2 or SEQ ID NO:4, and more preferably still, a polypeptide that includes within its amino acid sequence a sequence essentially as set forth in SEQ ID NO:2 or SEQ ID NO:4. In a preferred embodiment, such a DNA segment comprises a gene encoding the amino acid sequence of SEQ ID NO:2 or SEQ ID NO:4, and more preferably still, comprises a polynucleotide which is identical to, or substantially homologous with, a contiguous polynucleotide sequence from SEQ ID NO:1 or SEQ ID NO:3.

The term "a sequence essentially as set forth in SEQ ID NO:2 or SEQ ID NO:4," means that the sequence substantially corresponds to a portion of the sequence of SEQ ID NO:2 or SEQ ID NO:4 and has relatively few amino acids that are not identical to, or a biologically functional equivalent of, the amino acids of any of these sequences. The term "biologically functional equivalent" is well understood in the art and is further defined in detail herein (e.g., see Illustrative Embodiments). Accordingly, sequences that have between about 70% and about 80%, or more preferably between about 81% and about 90%, or even more preferably between about 91% and about 99% amino acid sequence identity or functional equivalence to the amino acids of SEQ ID NO:2 or SEQ ID NO:4 will be sequences that are "essentially as set forth in SEQ ID NO:2 or SEQ ID NO:4."

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared that include a short contiguous stretch encoding the whole or a portion of the peptide sequence disclosed in SEQ ID NO:2 or SEQ ID NO:4, or that are identical to or complementary to DNA sequences which encode the peptide disclosed in SEQ ID NO:2 or SEQ ID NO:4, and particularly the DNA segment disclosed in either of SEQ ID NO:1 or SEQ ID NO:3. For example, DNA sequences such as about 23 nucleotides, and that are up to about 10,000, about 5,000, about 3,000, about 2,000, about 1,000, about 500, about 200, about 100, about 50, and about 23 base pairs in length (including all intermediate lengths) are also contemplated to be useful.

It will be readily understood that "intermediate lengths", in these contexts, means any. length between the quoted ranges, such as 23, 24, 25, 26, 27, 28, 29, 30, 31, 32, 33, 34, 35, 36, 37, 38, 39, 40, 41, 42, 43, etc.; 50, 51, 52, 53, etc.; 100, 101, 102, 103, etc.; 150, 151, 152, 153, etc.; including all integers through the 200–500; 500–1,000; 1,000–2,000; 2,000–3,000; 3,000–5,000; and up to and including sequences of about 6,000, 7,000, 8,000, 9,000, 10,000, 10,001, 10002, 10003, 11000, 12000, 13000, or so nucleotides and the like.

It will also be understood that this invention is not limited to the particular nucleic acid sequences which encode peptides of the present invention, or which encode the amino acid sequence of SEQ ID NO:2 or SEQ ID NO:4, including the DNA sequence which is particularly disclosed in SEQ ID NO:1 and SEQ ID NO:3. Recombinant vectors and isolated DNA segments may therefore variously include the peptide-coding regions themselves, coding regions bearing selected alterations or modifications in the basic coding region, or they may encode larger polypeptides that nevertheless include these peptide-coding regions or may encode biologically functional equivalent proteins or peptides that have variant amino acids sequences.

The DNA segments of the present invention encompass biologically-functional, equivalent peptides. Such sequences may arise as a consequence of codon redundancy and functional equivalency that are known to occur naturally within nucleic acid sequences and the proteins thus encoded. Alternatively, functionally-equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level.

If desired, one may also prepare fusion proteins and peptides, e.g., where the peptide-coding regions are aligned within the same expression unit with other proteins or peptides having desired functions, such as for purification or immunodetection purposes (e.g., proteins that may be purified by affinity chromatography and enzyme label coding regions, respectively).

Recombinant vectors form further aspects of the present invention. Particularly useful vectors are contemplated to be those vectors in which the coding portion of the DNA segment, whether encoding a full length protein or smaller peptide, is positioned under the control of a promoter. The promoter may be in the form of the promoter that is naturally associated with a gene encoding peptides of the present invention, as may be obtained by isolating the 5' non-coding sequences located upstream of the coding segment or exon, for example, using recombinant cloning and/or PCR™ technology, in connection with the compositions disclosed herein.

2.2 DNA Segments as Hybridization Probes and Primers

In addition to their use in directing the expression of the gene product of the novel MORC genes of the present invention, the nucleic acid sequences contemplated herein also have a variety of other uses. For example, they also have utility as probes or primers in nucleic acid hybridization embodiments. As such, it is contemplated that nucleic acid segments that comprise a sequence region that consists of at least a 23 nucleotide long contiguous sequence that has the same sequence as, or is complementary to, a 23 nucleotide long contiguous DNA segment of SEQ ID NO:1 or SEQ ID NO:3 will find particular utility. Longer contiguous identical or complementary sequences, e.g., those of about 25, 30, 35, 40, 45, 50, 60, 70, 80, 90, 100, 200, 300, 400, 500, 600, 700, 800, 900, 1000, 2000, 5000, 10000 etc. (including all intermediate lengths and up to and including full-length sequences) will also be of use in certain embodiments.

The ability of such nucleic acid probes to specifically hybridize to MORC and MORC-related gene sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of 23, 24, 25, 26, 27, 28, 29, 30, 35, 40, 45, 50, or even of 100–200 nucleotides or so, identical or complementary to the DNA sequence of SEQ ID NO:1 or SEQ ID NO:3, are particularly contemplated as hybridization probes for use in, e.g., Southern and Northern blotting. Smaller fragments will generally find use in hybridization embodiments, wherein the length of the contiguous complementary region may be varied, such as between about 23 and about 100 or so nucleotides, but larger contiguous complementarity stretches may be used, according to the length complementary sequences one wishes to detect.

The use of a hybridization probe of about 23 nucleotides in length allows the formation of a duplex molecule that is both stable and selective. Molecules having contiguous complementary sequences over stretches greater than 23 bases in length are generally preferred, though, in order to increase stability and selectivity of the hybrid, and thereby improve the quality and degree of specific hybrid molecules obtained. One will generally prefer to design nucleic acid molecules having gene-complementary stretches of 23 to 35 contiguous nucleotides, or even longer where desired.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. Nos. 4,683,195 and 4,683,202 (each incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C. Such selective conditions tolerate little, if any, mismatch between the probe and the template or target strand, and would be particularly suitable for isolating polynucleotide segments comprising MORC or MORC-related gene(s). Detection of DNA segments via hybridization is well-known to those of skill in the art, and the teachings of U.S. Pat. Nos. 4,965,188 and 5,176,995 (each incorporated herein by reference) are exemplary of the methods of hybridization analyses. Teachings such as those found in the texts of Maloy et al., 1994; Segal 1976; Prokop, 1991; and Kuby, 1991, are particularly relevant.

Of course, for some applications, for example, where one desires to prepare mutants employing a mutant primer strand hybridized to an underlying template or where one seeks to isolate MORC polypeptide-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

2.3 MORC Polypeptide Compositions

The invention also discloses and claims a composition comprising a MORC or MORC-related polypeptide. The composition may comprises one or more host cells which express a MORC or MORC-related polypeptide, recombinant host cells expresses the protein, cell suspensions, extracts, inclusion bodies, or tissue cultures or culture extracts which contain the MORC protein, culture supernatant, disrupted cells, cell extracts, lysates, homogenates, and the like. The compositions may be in aqueous form, or alternatively, in dry, semi-wet, or similar forms such as cell paste, cell pellets, or alternatively freeze dried, powdered, lyophilized, evaporated, or otherwise similarly prepared in dry form. Such means for preparing MORC polypeptides are well-known to those of skill in the art of protein isolation and purification. In certain embodiments, the MORC polypeptides may be purified, concentrated, admixed with other reagents, or processed to a desired final form. Preferably, the composition will comprise from about 1% to about 90% by weight of the MORC polypeptide, and more preferably from about 5% to about 50% by weight.

In a preferred embodiment, the MORC polypeptide compositions of the invention may be prepared by a process which comprises the steps of culturing a host cell which expresses a MORC or MORC-related polypeptide under conditions effective to produce such a protein, and then obtaining the protein from the cell. The obtaining of such a MORC polypeptide may further include purifying, concentrating, processing, or admixing the protein with one or more reagents. Preferably, the MORC or MORC-related polypeptide is obtained in an amount of from between about 1% to about 90% by weight, and more preferably from about 5% to about 70% by weight, and even more preferably from about 10% to about 20% to about 30%, or even to about 40% or 50% by weight.

The invention also relates to a method of preparing a MORC polypeptide composition. Such a method generally involves the steps of culturing a host cell which expresses a MORC polypeptide under conditions effective to produce the protein, and then obtaining the protein so produced. In a preferred embodiment the cell is an male germ cell, or any recombinant host cell which contains a MORC-encoding DNA segment. Alternatively, the recombinant plasmid vectors of the invention may be used to transform other suitable bacterial or eukaryotic cells to produce the MORC polypeptide of the invention. Eukaryotic host cells including human, mouse, and monkey, as well as yeast cells are contemplated to be particularly useful in the preparation of the MORC protein. Likewise, prokaryotic host cells including Gram-negative cells such as *E. coli*, Pseudomonas spp. and related Enterobacteraceae and the like are all contemplated to be useful in the preparation of the MORC polypeptides of the invention.

In such embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding a MORC polypeptide or peptide in its natural environment. Such promoters may include promoters normally associated with other genes, and/or promoters isolated from any bacterial, viral, or eukaryotic cell. Preferred eukaryotic cells are animal cells, with mammalian cells, particularly human cells, being most preferred. Naturally, it will be important to employ a promoter that effectively directs the expression of the DNA segment in the cell type, tissue, organism, animal, or recombinant host cell chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the Pichia expression vector system (Pharmacia LKB Biotechnology).

In connection with expression embodiments to prepare recombinant proteins and peptides, it is contemplated that longer DNA segments will most often be used, with DNA segments encoding the entire peptide sequence being most preferred. However, it will be appreciated that the use of shorter DNA segments to direct the expression of polypeptides or epitopic core regions, such as may be used to generate anti-MORC antibodies, also falls within the scope of the invention. DNA segments that encode peptide antigens from about 8 to about 50 amino acids in length, or more preferably, from about 8 to about 30 amino acids in length, or even more preferably, from about 8 to about 20 amino acids in length are contemplated to be particularly useful. Such peptide epitopes may be amino acid sequences which comprise contiguous amino acid sequences from SEQ ID NO:2 or SEQ ID NO:4.

2.4 MORC Transgenes and Transformed Host Cells Expressing MORC

In yet another aspect, the present invention provides methods for producing a transgenic cell, and in particular a plant or animal cell which expresses a nucleic acid segment encoding the novel MORC polypeptide of the present invention. The process of producing transgenic cells is well-known in the art. In general, the method comprises transforming a suitable host cell with a DNA segment which contains a promoter operatively linked to a coding region that encodes a MORC polypeptide. Such a coding region is generally operatively linked to a transcription-terminating region, whereby the promoter is capable of driving the transcription of the coding region in the cell, and hence providing the cell the ability to produce the recombinant protein in vivo. Alternatively, in instances where it is desirable to control, regulate, or decrease the amount of a particular recombinant MORC polypeptide expressed in a particular transgenic cell, the invention also provides for the expression of MORC-specific mRNA, and antisense polynucleotides that specifically bind to MORC-specific mRNA. The use of antisense compositions as a means of controlling or decreasing the amount of a given protein of interest in a cell is well-known in the art, and is described in detail herein.

In a preferred embodiment, the invention encompasses an animal cell which has been transformed with a nucleic acid segment of the invention, and which expresses a gene or gene segment encoding one or more of the novel polypeptide compositions disclosed herein. As used herein, the term "transgenic host cell" is intended to refer to a host cell, either prokaryotic or eukaryotic, that has incorporated DNA sequences, including but not limited to genes which are perhaps not normally present, DNA sequences not normally transcribed into RNA or translated into a protein ("expressed"), or any other genes or DNA sequences which one desires to introduce into the non-transformed host cell, such as genes which may normally be present in the non-transformed cell but which one desires to either genetically engineer or to have altered expression.

It is contemplated that in some instances the genome of a transgenic host cell of the present invention will have been augmented through the stable introduction of a MORC transgene, either-native MORC, or synthetically modified or mutated MORC. In some instances, more than one transgene will be incorporated into the genome of the transformed host cell. Such is the case when more than one MORC polypeptide-encoding DNA segment is incorporated into the genome of such a cell. In certain situations, it may be desirable to have one, two, three, four, or even more MORC polypeptides (either native or recombinantly-engineered) incorporated and stably expressed in the transformed transgenic host cell. In preferred embodiments, the introduction of the transgene into the genome of the host cell results in a stable integration wherein the progeny of such cells also contain a copy of the transgene in their genome.

A preferred gene which may be introduced includes, for example, a DNA segment comprising one or more MORC gene(s), and particularly one or more of the MORC or MORC-like polypeptides disclosed herein. Highly preferred nucleic acid sequences are those which have the nucleic acid sequence of SEQ ID NO:1 or SEQ ID NO:3, or biologically-functional equivalents thereof, sequences which hybridize to the sequence of SEQ ID NO:1 or SEQ ID NO:3, or sequences which encode the amino acid sequence of SEQ ID NO:2 or SEQ ID NO:4, or sequences which encode a biologically functional equivalent protein of SEQ ID NO:2 or SEQ ID NO:4, or any of those sequences which have been genetically engineered to alter, modify, change, decrease or increase the suppressor activity or specificity of the MORC polypeptide in such a transformed host cell.

Means for transforming a host cell and the preparation of a transgenic cell line are well-known in the art (as exemplified in U.S. Pat. Nos. 5,550,318; 5,508,468; 5,482,852; 5,384,253; 5,276,269; and 5,225,341, all specifically incorporated herein by reference), and are briefly discussed herein. Vectors, including plasmids, cosmids, phage, phagemids, BACs (bacterial artificial chromosomes), YACs (yeast artificial chromosomes), and DNA segments for use in transforming such cells will, of course, generally comprise either the operons, genes, or gene-derived sequences of the present invention, either native, or synthetically-derived, and particularly those encoding the disclosed polypeptides. These DNA constructs can further include structures such as promoters, enhancers, polylinkers, or even gene sequences which have positively- or negatively-regulating activity upon the particular genes of interest as desired. The DNA segment or gene may encode either a native or modified polypeptide, which will be expressed in the resultant recombinant cells, and/or which will impart a desired phenotype to the transformed host cell.

2.5 Compositions and Methods for Producing MORC-specific Antibodies

In particular embodiments, the inventors contemplate the use of antibodies, either monoclonal or polyclonal which specifically bind to one or more of the MORC polypeptides disclosed herein. Means for preparing and characterizing antibodies are well known in the art (See, e.g, Harlow and Lane, 1988; incorporated herein by reference). The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified MORC polypeptide, polypeptide or peptide. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986, pp. 60–61), but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, (Gefter et al., 1977). The use of electrically induced fusion methods is also appropriate (Goding, 1986, pp. 71–74).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two wk. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three wk) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

2.6 MORC Polypeptide Screening Methods and Immunodetection Kits

The present invention also provides compositions, methods and kits for screening samples suspected of containing a MORC polypeptide or a MORC polynucleotide that encodes such a polypeptide. Alternatively, the invention provides compositions, methods and kits for screening samples suspected of containing MORC or MORC-related polypeptides or genes encoding MORC or MORC-related polypeptides which are functionally equivalent to, or substantially homologous to, the MORC polypeptides disclosed herein. Such screening may be performed on samples such as transformed host cells, clinical or laboratory samples suspected of containing or producing such a polypeptide or nucleic acid segment. A kit can contain a novel nucleic acid segment or an antibody of the present invention. The kit can contain reagents for detecting an interaction between a sample and a nucleic acid or an antibody of the present invention. The provided reagent can be radio-, fluorescently- or enzymatically-labeled. The kit can contain a known radiolabeled agent capable of binding or interacting with a nucleic acid or antibody of the present invention.

The reagent of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media, a test plate having a plurality of wells, or a microscope slide. When the reagent provided is a dry powder, the powder can be reconstituted by the addition of a suitable solvent, that may be provided.

In still further embodiments, the present invention concerns immunodetection methods and associated kits. It is proposed that the MORC polypeptides or peptides of the present invention may be employed to detect antibodies having reactivity therewith, or, alternatively, antibodies prepared in accordance with the present invention, may be employed to detect MORC or MORC-related polypeptides, peptides, or epitope-containing sequences specific to MORC. In general, these methods will include first obtaining a sample suspected of containing such a protein, peptide or antibody, contacting the sample with an antibody or peptide in accordance with the present invention, as the case may be, under conditions effective to allow the formation of an immunocomplex, and then detecting the presence of the immunocomplex.

In general, the detection of immunocomplex formation is quite well known in the art and may be achieved through the application of numerous approaches. For example, the present invention contemplates the application of ELISA, RIA, immunoblot (e.g., dot blot), indirect immunofluorescence techniques and the like. Generally, immunocomplex formation will be detected through the use of a label, such as a radiolabel or an enzyme tag (such as alkaline phosphatase, horseradish peroxidase, or the like). Of course, one may find additional advantages through the use of a secondary binding ligand such as a second antibody or a biotin/avidin ligand binding arrangement, as is known in the art.

For assaying purposes, it is proposed that virtually any sample suspected of comprising either a MORC polypeptide, a MORC-derived peptide or a MORC-related peptide or antibody sought to be detected, as the case may be, may be employed. It is contemplated that such embodiments may have application in the titering of antigen or antibody samples, in the selection of hybridomas, and the like. In related embodiments, the present invention contemplates the preparation of kits that may be employed to detect the presence of MORC polypeptides or related peptides and/or antibodies in a sample. Samples may include cells, cell supernatants, cell suspensions, cell extracts, enzyme fractions, protein extracts, or other cell-free compositions suspected of containing MORC polypeptides or peptide fragments thereof. Generally speaking, kits in accordance with the present invention will include a suitable MORC polypeptide, peptide or an antibody directed against such a protein or peptide, together with an immunodetection reagent and a means for containing the antibody or antigen and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container will generally include a vial into which the antibody, antigen or detection reagent may be placed, and preferably suitably aliquotted. The kits of the present invention will also typically include a means for containing the antibody, antigen, and reagent containers in close confinement for commercial sale. Such containers may include injection or blow-molded plastic containers into which the desired vials are retained.

2.7 MORC-derived Epitopic Sequences

The present invention is also directed to MORC protein or peptide compositions, free from total cells and other peptides, which comprise a purified MORC protein or peptide which incorporates an epitope that is immunologically cross-reactive with one or more anti-MORC antibodies. In particular, the invention concerns epitopic core sequences derived from MORC and MORC-derived proteins or peptides.

As used herein, the term "incorporating an epitope(s) that is immunologically cross-reactive with one or more anti-MORC antibodies" is intended to refer to a peptide or protein antigen which includes a primary, secondary or tertiary structure similar to an epitope located within a MORC polypeptide. The level of similarity will generally be to such a degree that monoclonal or polyclonal antibodies directed against the MORC polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of MORC immunodominant epitopes, and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, e.g., Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of about 8 to about 20 amino acids in length, and more preferably about 8 to about 15 amino acids in length. It is proposed that shorter antigenic MORC-derived peptides will provide advantages in certain circumstances, for example, in the preparation of immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to MORC polypeptides, and in particular mammalian MORC and/or MORC-related polypeptide sequences. These epitopic core sequences are identified herein in particular aspects as hydrophilic regions of the particular polypeptide antigen. It is proposed that these regions represent those which are most likely to promote T-cell or B-cell stimulation, and, hence, elicit specific antibody production.

An epitopic core sequence, as used herein, is a relatively short stretch of amino acids that is "complementary" to, and therefore will bind, antigen binding sites on the MORC polypeptide-directed antibodies disclosed herein. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence anticipated by the present disclosure would generally be on the order of about 8 amino acids in length, with sequences on the order of 10 to 20 being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins (see e.g., Jameson and Wolf, 1988; Wolf et al., 1988). Computerized peptide sequence analysis programs (e.g., DNAStar® software, DNAStar, Inc., Madison, Wis.) may also be useful in designing synthetic peptides in accordance with the present disclosure.

Syntheses of epitopic sequences, or peptides which include an antigenic epitope within their sequence, are readily achieved using conventional synthetic techniques such as the solid phase method (e.g., through the use of commercially available peptide synthesizer such as an Applied Biosystems Model 430A Peptide Synthesizer). Peptide antigens synthesized in this manner may then be aliquotted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at about 4° C., or more preferably, frozen. Of course, where the peptides are stored in a lyophilized or powdered state, they may be stored virtually indefinitely, e.g., in metered aliquots that may be rehydrated with a predetermined amount of water (preferably distilled) or buffer prior to use.

3.0 BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Figure 1A:
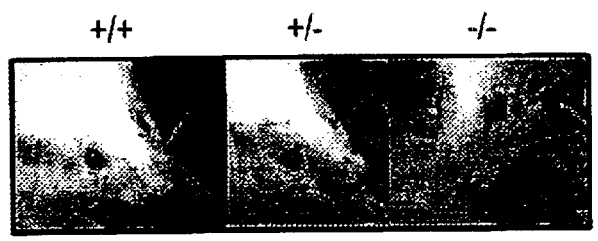
Figure 1B:

FIG. 1A and FIG. 1B. Gross appearance of morc mice. FIG. 1A. The wild-type FVB (+/+) pink (albino) eye color contrasts with the brown (+/− mice) or black (−/− mice) eye pigmentation due to one or two copies of the morc transgene, respectively. FIG. 1B. A marked size reduction is noted in the −/− testis compared with +/+ or +/− testis. Epididymides were of similar size in all three genotypes (the normal epididymis was inadvertently removed from the +/− specimen). The +/− testis is slightly pigmented due to transgene expression (see below).

Figures 2A, 2B:
Figures 2C, 2D:

FIG. 2A, FIG. 2B, FIG. 2C and FIG. 2D. Testes histology of morc mice. Representative H&E sections from testes of adult +/− (FIG. 2A, FIG. 2C) or −/− (FIG. 2B, FIG. 2D) mice demonstrate absence of spermatocytes in the −/− animals. Numerous pyknotic cells were present in −/− mice at the location where primary spermatocytes are found (magnification: FIG. 2A, FIG. 2B 400X; FIG. 2C, FIG. 2D 1000X).

FIG. 3A, FIG. 3B, FIG. 3C and FIG. 3D. Molecular analysis of morc spermatogenic arrest. Immunofluorescence analysis of spermatocytes from 24 day-old morc +/– (FIG. 3A, FIG. 3B) or –/– (FIG. 3C, FIG. 3D) mice, with anti-COR1 (red), recognizing mouse SYCP3, and anti-SYN1 (green), recognizing mouse SYCP1. In all panels, the green image is deliberately offset from the red image to facilitate visualization of coincidence of staining. FIG. 3A. Normal zygotene spermatocyte from a +/– mouse, with well developed axes staining with anti-COR1; these axes are not completely paired, and initiation of synapsis is recognized by staining with anti-SYN1. FIG. 3B. Normal pachytene spermatocyte from a +/– mouse; note coincident immunoreactivity for SYN1 with all axes indicating full and complete synapsis, except for the sex chromosomes (arrow), which normally synapse only in the most terminal region. FIG. 3C. Abnormal zygotene-like spermatocyte from a –/– animal. Even though full axial elements are formed, no pairing is seen. FIG. 3D. A morc –/– zygotene spermatocyte with focal regions of initiation of synapsis. Bar=10 µm.

FIG. 4A and FIG. 4B. Apoptosis in testes of adult morc mice. FIG. 4A. Most (>90%) wild-type tubules revealed no TUNEL positivity; the section shown here demonstrates the occasional apoptotic cells present in wild-type animals. FIG. 4B. In contrast, the majority of germ cells from –/– mice are undergoing apoptosis. Magnification: 200×.

Figure 5:
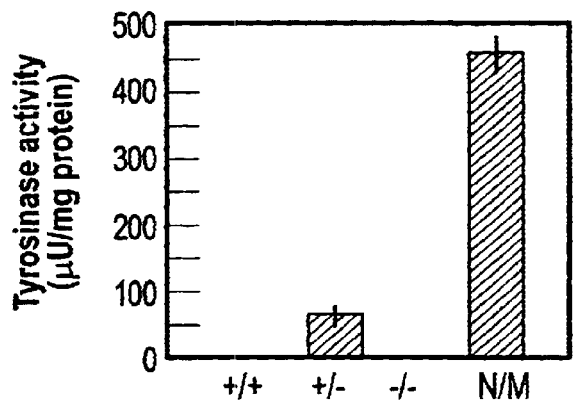

FIG. 5. Expression of tyrosinase in morc mice. Tyrosinase activity in testes extracts from morc +/+, +/–, or –/–, as compared to cultured mouse melanocytes. (NM). Histograms represent average of triplicate measurements and bars indicate standard deviation of the mean. Wild-type controls (+/+) show no antibody staining. Intense staining is seen in the germ cell cytoplasm of +/– testes. Fairit staining is also present in –/– germ cells. Magnification: 400X.

Figure 6A:
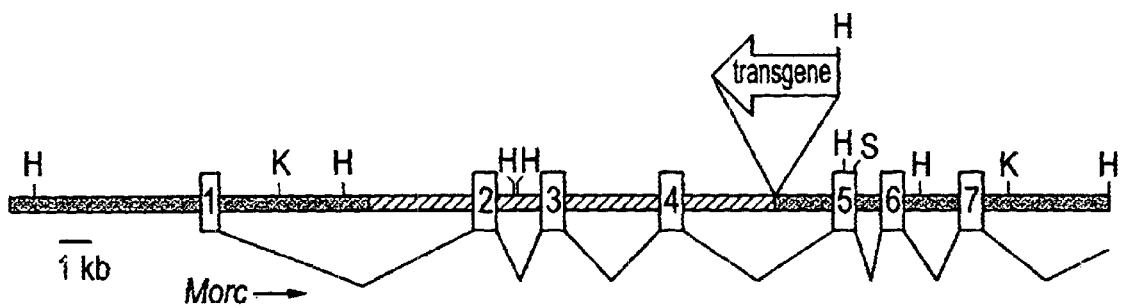
Figure 6B:
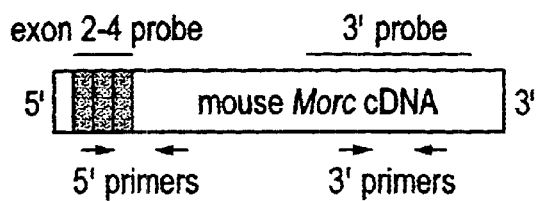

FIG. 6A and FIG. 6B. FIG. 6A. Physical map of the morc locus. Isolation of a P1 phage clone containing the transgene insertion site was previously described (Watson et al., 1998). H, HindIII; S, SalI; K, KpnI. Exons not drawn to scale. Diagonal hatches denote genomic deletion. Gray box indicates region sequenced. The precise structure of the transgene has not been determined. RT-PCR™ results indicate that it contains sequences integrated in head-to-head fashion. FIG. 6B. Schematic representation of Northern hybridization probes and RT-PCR™ primers. The exon 2–4 probe was an EcoRI/HindIII mouse Morc cDNA subclone (nt 161–333) radiolabeled with α-$^{32}$P dCTP by PCR™ using LacZ forward and reverse primers (Gibco BRL). A random-primer labeled mouse Morc cDNA fragment (nt 1771 to 3008) was used for the 3' region probe. Oligonucleotides were AGATGCCGGGGCTGTAAGACTCG (SEQ ID NO:12) and TTCATCCGGGGTTCAAAATACAGA (SEQ ID NO:13) (5' primers) and AAGCGCAGCCGCA-GAAGTCTCAACT (SEQ ID NO:14) and GCCG-GCAGCTGACAGTCACCACTC (SEQ ID NO:15) (3' primers).

Figure 7A:
Figure 7B:
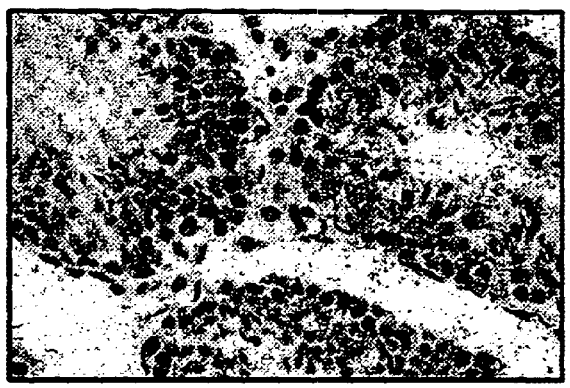
Figure 7C:
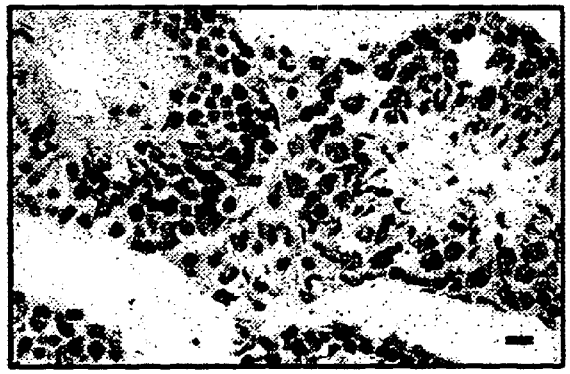

FIG. 7A, FIG. 7B and FIG. 7C. FIG. 7A. Nuclear localization of N-terminal FLAG epitope-tagged mouse MORC protein. The FLAG epitope was added at the N- or C-terminus of the mouse Morc peptide sequence by replacing the initiator methionine codon with a SalI restriction site (Watanabe et al., 1996) or the termination codon with an NruI restriction site (Nakamura et al., 1997), respectively. The FLAG-tagged MORC constructs were transiently expressed in COS7 cells using the pMEPy vector (Ohishi et al., 1996). Protein was visualized by fluorescence microscopy using biotinylated anti-FLAG antibody M2 (Eastman Kodak) and fluoresceinated streptavidin (Vector Laboratories). Nuclei and membranes were stained with DAPI and DiIC$_{18}$(3) (Molecular Probes), respectively. Cells were photographed using Ektachrome 400 color film and a Zeiss Axiphot fluorescence microscope with triple-pass filter. FIG. 7B. RNA in situ hybridization to serial sections of wild-type testis was performed as described previously (Yashima et al., 1998) using Morc antisense probes corresponding to the entire Morc cDNA coding region. Bar=20 µM. FIG. 7C. RNA in situ hybridization to serial sections of wild-type testis was performed as described previously (Yashima et al., 1998) using Morc sense probes corresponding to the entire Morc cDNA coding region. Bar=20 µM.

Figure 8:
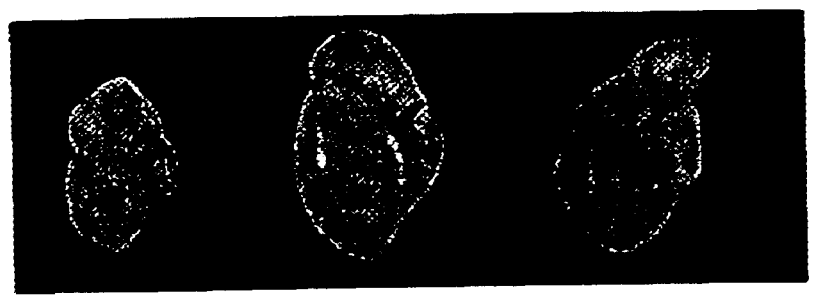

FIG. 8. Gross morphology of microrchidia –/–, +/+, and +/– testes. Note the dramatic size reduction in the –/– testis (left) and normal sized epididymis compared with wild type testis (middle). The +/– testis (right) is normal in size, with a slightly pigmented appearance probably due to transgene expression (see text). Epididymis was inadvertently removed from the +/– specimen but was normal.

Figure 9:
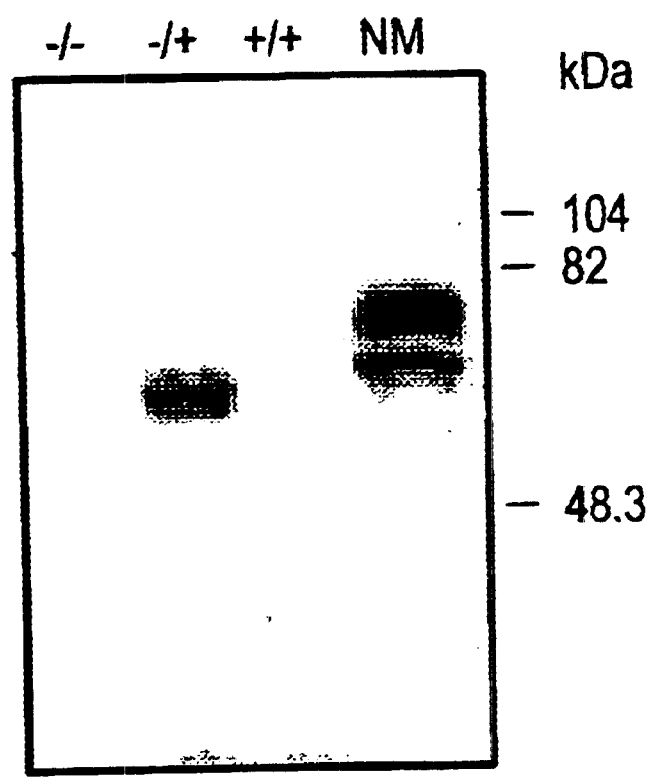

FIG. 9. Western blot of testes extracts from microchidia –/–, +/– and +/+ mice. Whole tissue extracts were isolated from the three types of mice followed by SDS-PAGE and western blotting. Pep7 antibody staining reveals a single band in heterozygous mice of approximately 60 kDa (predicted 62 kDa) (Kwon et al., 1989). No staining was present in mutant mice (–/–) or in wild type controls. Tyrosinase from normal melanocytes (NM) demonstrated reduced electrophoretic mobility, probably due to post-translational processing.

FIG. 10. Immunohistochemical staining of tyrosinase in wild type and microrchidia +/– and –/– testis. Positive staining in is seen in the cytoplasm of germ cells in +/– animals (middle panel) and weakly in –/– mice (right panel). Wild type controls show no antibody staining (left panel).

Figure 11:
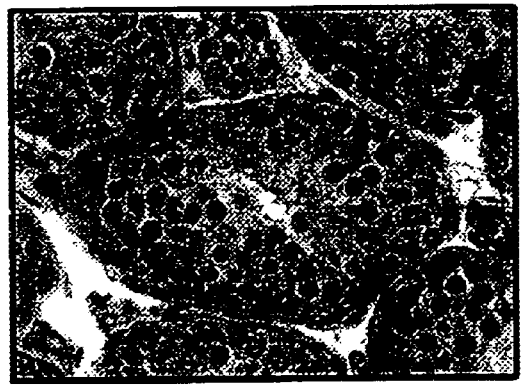
Figure 11:
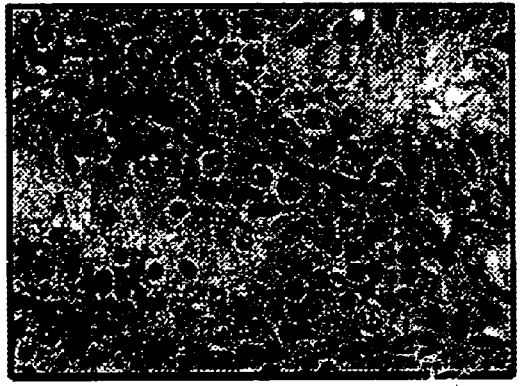
Figure 11:
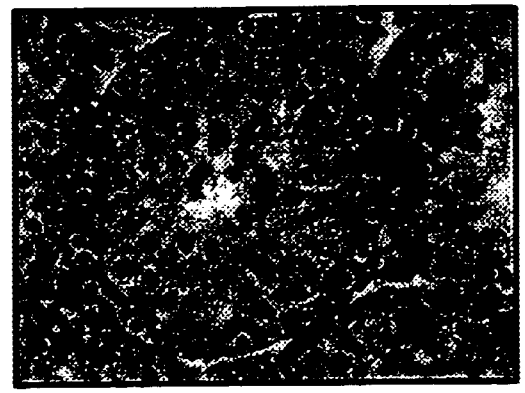
Figure 11:

FIG. 11. Longitudinal studies of testis histology of –/– versus +/– mice.

FIG. 12A and FIG. 12B. Southern blotting using a probe flanking the transgene. Genomic DNA from +/+, +/–, or –/– animals was digested with EcoRI and hybridized with probe 1(A) or probe 2(B) (see FIG. 13).

FIG. 13. Physical map of the microrchidia locus. Restriction map of transgene insertion site. B, BamHI; E, EcoRI; H, HindIII; K, KpnI; S, SalI. Six exons of the Morc gene are shown (boxes); shaded exon was identified by exon trapping; hatched exons are deleted. Arrows indicate direction of transcription. Probes 1 and 2 used for Southern blots are indicated.

FIG. 14. Mapping of the mouse Morc gene. Filled and open boxes represent homozygous and heterozygous genotypes respectively.

Figure 15:
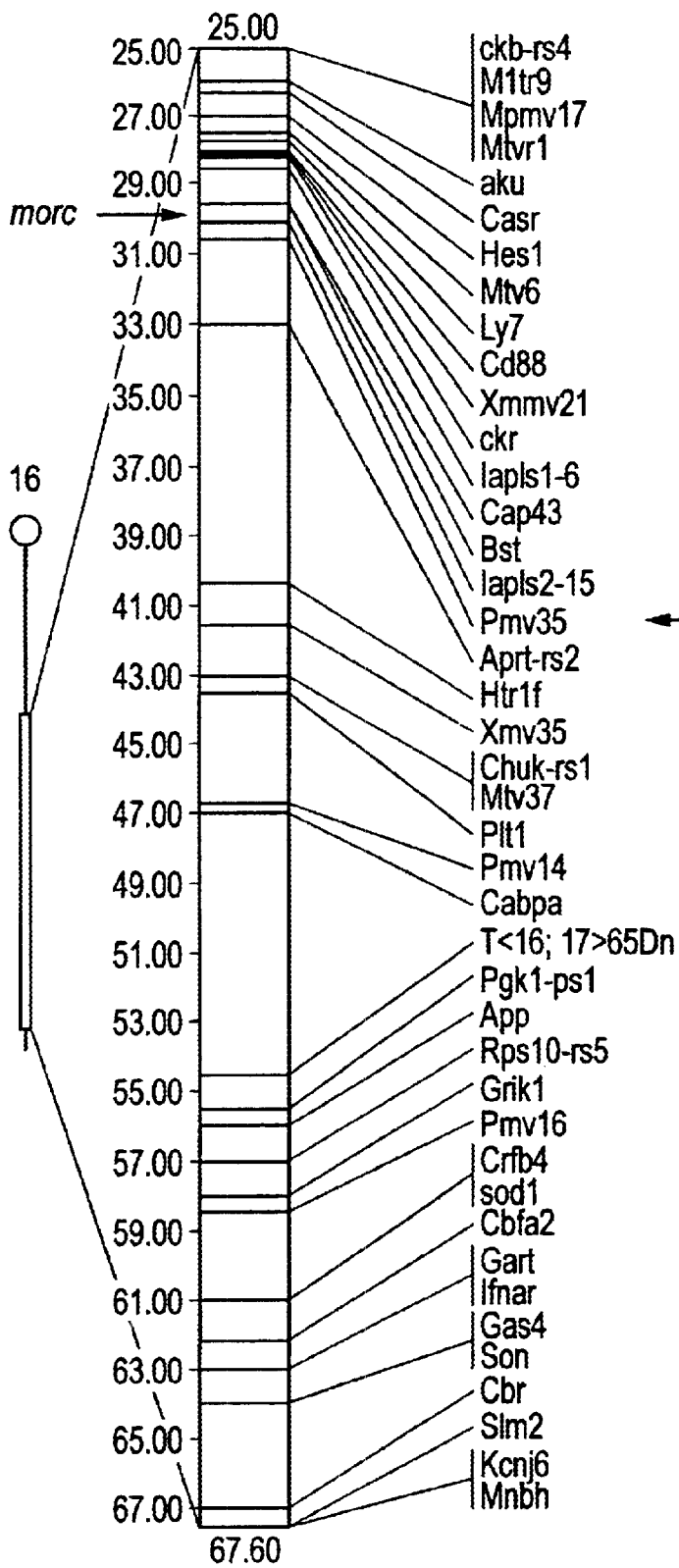

FIG. 15. Synteny map for mouse chromosome 16, showing map location of the mouse MORC gene.

4.0 DESCRIPTION OF ILLUSTRATIVE EMBODIMENTS

The inventors have exploited a transgene insertion-deletion event to positionally clone a novel mammalian spermatogenesis gene. The microchidia mutation specifically blocks male germ cell development at the entry to meiosis, a mutant phenotype that to our knowledge has not been previously described in mammals. Morc encodes a protein critical for the transition from progenitors to committed haploid germ cells.

4.1 Comparison of MORC to other Spermatogenesis Genes

MORC has several salient features that distinguish it from previously characterized mouse or Drosophila spermatogenesis genes. First, the gene does not appear to be required for germ cell proliferation. Second, the mutation is not pleiotropic. Third, the gene is expressed solely in testis, consistent with the lack of pleiotropy. Fourth, the mutant arrests early in spermatogenesis, prior to the pachytene stage of meiosis I, without discernible "leakiness."

4.2 Infertility

Infertility is a common clinical problem, affecting about 10% of all couples. Many cases are likely to have genetic etiologies, and some could be due to mutations in the biochemical pathway(s) in which morc acts. The histophenotype of older morc −/− mice is reminiscent of the "Sertoli cell only" class of human male infertility. In addition, genes such as morc that are required specifically for spermatogenesis may also provide attractive new targets for male contraception.

The search for genes that are specifically responsible for human infertility has yielded several candidates. An example is the identification of DAZ (Deleted in Azoospermia), a gene that maps to a Y chromosomal region deleted in 10% of sterile men (Lahn and Page, 1997; Vogt, 1997). The murine homologue of DAZ (Dazla) has been knocked out (Ruggiu et al., 1997), and like morc, Dazla −/− male mice show severe disruption of spermatogenesis from an early age. However, germ cell proliferation and tubule formation is markedly decreased during early testis development in Dazla −/− mice, suggesting that Dazla acts premeiotically. By contrast, morc −/− males have normal premeiotic development and show germ cell arrest only upon entry into meiosis. Further, Dazla −/− females are infertile and show a severe lack of germ cells entering meiosis from 15 dpc onward (Ruggiu et al., 1997), in contrast to the histologically normal ovaries in fertile morc −/− females.

Other "spermatogenesis genes" have been identified by the phenotypes of mouse knockouts. An interesting example of a rapidly growing class of such genes are those functioning in recombination, especially the mismatch repair (MMR) family members, which include the mouse homologues of the bacterial mutS and mutL genes. The initial focus in MMR was in relation to this system's ability to remove unpaired stretches of DNA formed by polymerase errors or misincorporation (Modrich and Lahue, 1996). However, it soon became apparent from studies of knockout mice that MMR is required for completion of meiosis. Mice deficient for mutL homologues Alh1 or Pms2 have meiotic arrest phenotypes (Baker et al., 1995; Edelmann et al., 1996). Of note, the Mlh1 −/− phenotype is different from that of morc (and Pms2 −/− mice) in that both sexes are infertile. The Mlh1 −/− testes histophenotype is similar to the morc locus described herein in that arrest occurs early in meiosis I and produces condensed pyknotic primary spermatocytes (Edelmann et al., 1996). The Pms2 −/− phenotype is male-specific, as is morc. However, in contrast to morc −/− males, Pms2 −/− males produce round and elongating spermatids, although with many morphological abnormalities. During meiotic prophase, meiotic chromosomes from Pms2 −/− spermatocytes exhibit aberrant synapsis formation, resulting in large numbers of asynaptic bivalents (Baker et al., 1995).

Other interesting DNA repair and genome stability genes that resulted in germ cell abnormalities when knocked out are the Ataxia telangiectasia mutated (ATM) and BRCA2 genes (Barlow et al., 1996; Xu et al., 1996; Elson et al., 1996; Connor et al., 1997). In fact, a major role for ATM may be to monitor DNA damage during meiosis (Keegan et al., 1996; Barlow et al., 1997). These and many other mutant mice have unequivocally linked DNA repair with gametogenesis, and similarities between the phenotypes of morc and DNA repair and that of recombination deficient mice raise the possibility that morc functions in recombination.

The TUNEL data show that germ cells in testes lacking morc die by programmed cell death. Apoptosis has also been shown to be a mechanism of germ cell loss in mutants such as the Mlh1 −/− mice (Edelmann et al., 1996) or Bclw knockout mice (Ross et al., 1998). Multicellular organisms have exploited apoptosis for many purposes, including regulation of germ cell quantity and quality, but also tissue renovation, organogenesis, immune cell selection and cancer protection. Apoptosis occurs via a complex and highly regulated sequence of events. In the testis, apoptosis is a normal feature of germinal epithelium, producing a final wave of sperm that reflects the constant removal of both defective and probably also normal cells (Roosen-Runge, 1955; Roosen-Runge, 1973; Allan et al., 1987). Teleologically it makes sense that there exists a low threshold for apoptosis of male gametes with genomic errors, since their progeny could waste precious female reproductive resources if they were able to fertilize an oocyte (Braun, 1998). Two germ cell apoptotic pathways have been distinguished. The first depends on the presence of normal p53, for example, the germ cell apoptosis induced by ionizing radiation (Beumer et al., 1997; Odorisio et al., 1998). The second is a p53-independent pathway that is triggered by chromosomal abnormalities such as asynapsis during prophase I of meiosis (Odorisio et al., 1998).

Random insertional mutagenesis has found wide application in Drosophila genetics, where it is possible to systematically screen for desired phenotypes, including male sterility (Castrillon et al., 1993). Such screens are impractical in mammals, but a number of mutations have been identified serendipitously during planned creation of transgenic mice. These mutations have provided major insights into mammalian development. For example, phenotypes involving germ cell proliferation (Pellas et al., 1991), limb formation (Woychik et al., 1985), and aging (Kuro-o et al., 1997) have been reported, and in the latter two cases novel genes were identified (Kuro-o et al., 1997; Woychik et al., 1990). Similarly, the insertional mutation described in Example 1 may be used to isolate the Morc gene and may likely yield significant insight into male germ cell development and human infertility.

4.3 Male Infertility

Male infertility is a common clinical problem and represents approximately 40 percent of all causes of inability of couples to conceive. Many of these cases are likely to be due to genetic defects in spermatogenesis. Particular attention has been drawn to genes encoded by the Y-chromosome (e.g., DAZ, RBM), which appear to be especially prone to deletions and may explain up to 10% of azoospermic cases. By contrast, autosomal recessive mutations in a gene such as MORC would be expected to explain only a small fraction of cases. Nevertheless, the inventors believe the potential medical relevance of MORC to human sterility does merit exploration. In addition, humans provide a valuable system for understanding the range of. phenotypes associated with specific mutations, i.e. the effects of varying genetic backgrounds or environments. For example, DAZ mutations are associated with a clinical and histologic spectrum ranging from normal fertility to reduced sperm cell numbers (oligospermia) to azoospermia with meiotic arrest to azoospermia with absent germ cells (Reijo et al., 1995; 1996).

The best technique to find human mutations is to scrutinize genomic DNA. However, mutation detection is exceedingly laborious, especially for a large gene like MORC. As an alternative approach, one may first screen for absence of MORC expression, then look for the causative mutation(s). For instance, missense mutations that do not affect mRNA stability will not be detected. Another problem is false positives. If MORC expression is confined to germ cells, expression would be absent in testes that lack germ cells for any reason. Most of these false positives may be eliminated by focusing on infertile men with spermatogonia present on testicular biopsy. Samples from men with spermatogenic arrest and known DAZ deletions may be examined, and it is expected that such men will show normal or only mildly reduced levels of MORC expression.

The cDNA microarray system is a new approach recently developed at the Lawrence Livermore National Laboratory to monitor in parallel the expression of large numbers of genes (up to $10^4$). The power of this system is that cDNA clones are spotted at high density and hybridization probes can be prepared from small amounts of mRNA by reverse transcription. The method uses two-color fluorescence to detect differences in relative transcript levels. This approach minimizes the effort necessary to assay each gene for abnormal expression and allows large numbers of samples to be tested. A set of more than 60 genes have been identified that will occupy the first human reproductive cDNA microarray and have collected human cDNAs for approximately two thirds of these genes.

Blood and testis tissue samples have been collected from the following four groups of men, all less than 50 years old: 1) Fertile controls with a history of paternity and no history of fertility risk factors or prior fertility surgery. 2) Patients with a history significant for infertility and a semen evaluation that reveals a sperm concentration of less than $1 \times 10^7$ sperm/ml or a total motile sperm count (TMC) of less than $5 \times 10^6$ sperm. 3) Patients with azoospermia with testis biopsy-proven spermatogenic arrest or germ cell absence. 4) The parents and siblings of patients.

Results of gene expression analysis may indicate potential mutations in patients that will require verification by DNA analysis of parents or siblings. If any such patients are identified, they may be scrutinized for mutations in the MORC gene. Additional family information and blood and germ cell samples may be collected as necessary. To determine the intron/exon structure and splice sites sequences for the human MORC gene, primers from the human MORC cDNA sequence may be used to directly sequence exon/intron boundaries from the human MORC P1 genomic using published techniques (Boysen et al., 1997; Benes et al., 1997) or a $^{33}$P cycle sequencing kit (Amersham Life Science, Cleveland, Ohio).

4.4 Pharmaceutical Compositions

In certain embodiments, the present invention concerns formulation of one or more of the polynucleotide and/or polypeptide compositions disclosed herein in pharmaceutically-acceptable solutions for administration to a cell or an animal, either alone, or in combination with one or more other modalities of therapy or treatment.

It will also be understood that, if desired, the nucleic acid segment, RNA, DNA or PNA compositions disclosed herein may be administered in combination with other agents as well, such as, e.g., proteins or polypeptides or various pharmaceutically-active agents. As long as the composition comprises at least one MORC polynucleotide or polypeptide composition, there is virtually no limit to other components which may also be included, given that the additional agents do not cause a significant adverse effect upon contact with the target cells or host tissues. The RNA, DNA, or PNA-derived compositions may thus be delivered along with various other agents as required in the particular instance. Such RNA, DNA, or PNA compositions may be purified from host cells or other biological sources, or alternatively may be chemically synthesized as described herein. Likewise, such compositions may comprise substituted or derivatized RNA, DNA, or PNA compositions. Such compositions may also include modified peptide or nucleic acid substituent derivatives, as long as the base sequence of the RNA, DNA, or PNA molecule corresponds to one or more of the contiguous base sequences described herein.

The formulation of pharmaceutically-acceptable excipients and carrier solutions are well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

4.4.1 Oral Delivery

The pharmaceutical compositions disclosed herein may be delivered via oral administration to an animal, and as such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. No. 5,641,515; U.S. Pat. No. 5,580,579 and U.S. Pat. No. 5,792,451, each specifically incorporated herein by reference in its entirety). The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Typically, these formulations may contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as those containing sodium borate, glycerin and potassium bicarbonate, or dispersed in a dentifrice, including: gels, pastes, powders and slurries, or added in a therapeutically effective amount to a paste dentifrice that may include water, binders, abrasives, flavoring agents, foaming agents, and humectants, or alternatively fashioned into a tablet or solution form that may be placed under the tongue or otherwise dissolved in the mouth.

4.4.2 Injectable Delivery

Alternatively, the pharmaceutical compositions disclosed herein may be administered parenterally, intravenously, intramuscularly, or even intraperitoneally as described in U.S. Pat. No. 5,543,158; U.S. Pat. No. 5,641,515 and U.S. Pat. No. 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria. and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption. delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

4.4.3 Nasal Delivery

In certain embodiments, the pharmaceutical compositions of the invention may be deliverable to an animal by intranasal sprays, inhalation, and/or other aerosol delivery vehicles. Methods for delivering genes, nucleic acids, and peptide compositions directly to the lungs via nasal aerosol sprays has been described e.g., in U.S. Pat. No. 5,756,353 and U.S. Pat. No. 5,804,212 (each specifically incorporated herein by reference in its entirety), and delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

4.4.4 Additional Modes of Delivery for MORC Compositions

In addition to the methods of delivery described above, the following techniques are also contemplated as alternative methods of MORC composition delivery. Sonophoresis (i.e., ultrasound) has been used and described in U.S. Pat. No. 5,656,016 (specifically incorporated herein by reference in its entirety) as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. No. 5,770,219 and U.S. Pat. No. 5,783,208) and feedback controlled delivery (U.S. Pat. No. 5,697,899), each specifically incorporated herein by reference in its entirety.

4.5 Pharmaceutical Delivery Formulations 4.5.1 Liposome-, Nanocapsule-, and Microparticle-Mediated Delivery In certain embodiments, the inventors contemplate the use of liposomes, nanocapsules, microparticles, microspheres, lipid particles, vesicles, and the like, for the introduction of the pharmaceutical compositions comprising one or more of the polynucleotides or polypeptides of the present invention into suitable host cells. In particular, the compositions of the present invention may be formulated for delivery either encapsulated in a lipid particle, a liposome, a vesicle, a nanosphere, or a nanoparticle or the like.

Such formulations may be preferred for the introduction of pharmaceutically-acceptable formulations of the nucleic acids and polypeptides disclosed herein. The formation and use of liposomes is generally known to those of skill in the art (see for example, Couvreur et al., 1977; Couvreur, 1988; Lasic, 1998; which describes the use of liposomes and nanocapsules in the targeted antibiotic therapy for intracellular bacterial infections and diseases). Recently, liposomes were developed with improved serum stability and circulation half-times (Gabizon and Papahadjopoulos, 1988; Allen and Choun, 1987; U.S. Pat. No. 5,741,516, specifically incorporated herein by reference in its entirety). Further, various methods of liposome and liposome like preparations as potential drug carriers have been reviewed (Takakura, 1998; Chandran et al., 1997; Margalit, 1995; U.S. Pat. No. 5,567,434; U.S. Pat. 5,552,157; U.S. Pat. No. 5,565,213; U.S. Pat. No. 5,738,868 and U.S. Pat. No. 5,795,587, each specifically incorporated herein by reference in its entirety).

Liposomes have been used successfully with a number of cell types that are normally resistant to transfection by other procedures including T cell suspensions, primary hepatocyte cultures and PC 12 cells (Renneisen et al., 1990; Muller et al., 1990). In addition, liposomes are free of the DNA length constraints that are typical of viral-based delivery systems. Liposomes have been used effectively to introduce genes, drugs (Heath and Martin, 1986; Heath et al., 1986; Balazsovits et al., 1989; Fresta and Puglisi, 1996), radiotherapeutic agents (Pikul et al., 1987), enzymes (Imaizumi et al., 1990a; Imaizumi et al., 1990b), viruses (Faller and Baltimore, 1984), transcription factors and allosteric effectors (Nicolau and Gersonde, 1979) into a variety of cultured cell lines and animals. In addition, several successful clinical trails examining the effectiveness of liposome-mediated drug delivery have been completed (Lopez-Berestein et al., 1985a; 1985b; Coune, 1988; Sculier et al., 1988). Furthermore, several studies suggest that the use of liposomes is not associated with autoimmune responses, toxicity or gonadal localization after systemic delivery (Mori and Fukatsu, 1992).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 $\mu$m. Sonication of MLVs results in the formation of small unilamellar vesicles (SUVs) with diameters in the range of 200 to 500 Å, containing an aqueous solution in the core.

Liposomes bear resemblance to cellular membranes and are contemplated for use in connection with the present invention as carriers for the peptide compositions. They are widely suitable as both water- and lipid-soluble substances can be entrapped, i.e. in the aqueous spaces and within the bilayer itself, respectively. It is possible that the drug-bearing liposomes may even be employed for site-specific delivery of active agents by selectively modifying the liposomal formulation.

In addition to the teachings of Couvreur et al. (1977; 1988), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins such as cytochrome c bind, deform and penetrate the bilayer, thereby causing changes in permeability. Cholesterol inhibits this penetration of proteins, apparently by packing the phospholipids more tightly. It is contemplated that the most useful liposome formations for antibiotic and inhibitor delivery will contain cholesterol.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicochemical properties of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity and surface charge. They may persist in tissues for h or days, depending on their composition, and half lives in the blood range from min to several h. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow and lymphoid organs.

Targeting is generally not a limitation in terms of the present invention. However, should specific targeting be desired, methods are available for this to be accomplished. Antibodies may be used to bind to the liposome surface and to direct the antibody and its drug contents to specific antigenic receptors located on a particular cell-type surface. Carbohydrate determinants (glycoprotein or glycolipid cell-surface components that play a role in cell-cell recognition, interaction and adhesion) may also be used as recognition sites as they have potential in directing liposomes to particular cell types. Mostly, it is contemplated that intravenous injection of liposomal preparations would be used, but other routes of administration are also conceivable.

Alternatively, the invention provides for pharmaceutically-acceptable nanocapsule formulations of the polynucleotide or polypeptide compositions of the present invention. Nanocapsules can generally entrap compounds in a stable and reproducible way (Henry-Michelland et al., 1987; Quintanar-Guerrero et al., 1998; Douglas et al., 1987). To avoid side effects due to intracellular polymeric overloading, such ultrafine particles (sized around 0.1 $\mu$m) should be designed using polymers able to be degraded in vivo. Biodegradable polyalkyl-cyanoacrylate nanoparticles that meet these requirements are contemplated for use in the present invention, and such particles may be are easily made, as described (Couvreur et al., 1980; 1988; zur Muhlen et al., 1998; Zambaux et al. 1998; Pinto-Alphandry et al., 1995 and U.S. Pat. No. 5,145,684, specifically incorporated herein by reference in its entirety). In particular, methods of antisense oligonucleotide delivery to a target cell using either nanoparticles or nanospheres (Schwab et al., 1994; Truong-Le et al., 1998) are also particularly contemplated to be useful in formulating the disclosed compositions for administration to an animal, and to a human in particular.

4.5.2 Peptide Vectors for MORC Antisnese Therapies

The recent development of an antisense delivery method based on the use of a short peptide vector, termed MPG (27 residues), is also contemplated. The MPG peptide contains a hydrophobic domain derived from the fusion sequence of HIV gp41 and a hydrophilic domain from the nuclear localization sequence of SV40 T-antigen (Morris et al., 1997). It was demonstrated in that several molecules of the MPG peptides coat the antisense oligonucleotides and can be delivered into cultured mammalian cells in less than 1 hour with relatively high efficiency (90%). Further, the interaction with MPG strongly increases both the stability of the oligonucleotide to nuclease and the ability to cross the plasma membrane (Morris et al., 1997).

4.6 Therapeutic and Diagnostic Kits

The invention also encompasses one or more of the compositions together with one or more pharmaceutically-acceptable excipients, carriers, diluents, adjuvants, and/or other components, such as additional antihypertensive compositions, oligonucleotides, peptides, antigens, or other therapeutic compositions as may be employed in the formulation of particular polynucleotide or polypeptide delivery formulations, and in the preparation of pharmaceutical agents for administration to an animal.

As such, preferred animals for administration of the pharmaceutical compositions disclosed herein include mammals, and particularly humans. Other preferred animals include murines, bovines, equines, porcines, canines, and felines. The composition may include partially or significantly purified compositions, either alone, or in combination with one or more additional active ingredients, which may be obtained from natural or recombinant sources, or which may be obtainable naturally or either chemically synthesized, or alternatively produced in vitro from recombinant host cells expressing DNA segments encoding such additional active ingredients.

Therapeutic kits may also be prepared that comprise at least one of the MORC compositions disclosed herein and instructions for using the composition as a therapeutic agent. The container means for such kits may typically comprise at least one vial, test tube, flask, bottle, syringe or other container means, into which the antisense composition(s) may be placed, and preferably suitably aliquoted. Where a second pharmaceutical composition is also provided, the kit may also contain a second distinct container means into which this second composition may be placed. Alternatively, the plurality of MORC compositions may be prepared in a single pharmaceutical composition, and may be packaged in a single container means, such as a vial, flask, syringe, bottle, or other suitable single container means. The kits of the present invention will also typically include a means for containing the vial(s) in close confinement for commercial sale, such as, e.g., injection or blow-molded plastic containers into which the desired vial(s) are retained.

Alternatively, for the preparation of diagnostic kits, and for methods relating to the use of these compounds in the identification of MORC-specific nucleic acids in a biological sample, such kits may be prepared that comprise at least one of the MORC polynucleotides disclosed herein and instructions for using the composition as a probe for MORC-specific nucleic acids in a hybridization assay. The container means for such kits may typically comprise at least one vial, test tube, microcentrifuge tube, or other container means, into which the antisense composition(s) may be placed and suitably aliquoted. Where a radiolabel or fluorigenic label or other such detecting means is included within the kit, the labeling agent may be provided either in the same container as the oligonucleotide composition, or may alternatively be placed in a second distinct container means into which this second composition may be placed and suitably aliquoted. Alternatively, the oligonucleotide composition and the label may be prepared in a single container means, and in most cases, the kit will also typically include a means for containing the vial(s) in close confinement for commercial sale and/or convenient packaging and delivery.

4.7 MORC mRNA-Specific Oligonucleotide Compositions

As mentioned, in certain aspects, the MORC-encoding DNA sequence information provided by the present disclosure allows for the preparation of relatively short DNA, RNA, PNA, or derivatives thereof having the ability to specifically hybridize to an MORC-specific mRNA sequence encoding all or a portion of the MORC polypeptide, which the inventors have demonstrated useful in (1) the regulation, control, alteration, reduction and/or inhibition of MORC activity in a cell; (2) the treatment of cancer in an animal; and (3) the detection of MORC-specific nucleic acid sequences in a biological sample.

With respect to the latter, suitable oligonucleotide compositions comprising a sequence region of an appropriate length may be prepared based on a consideration of the natural mRNA sequence to which it will hybridize, and the size of the particular oligonucleotide used. Such segments may be those that are complementary to native MORC or MORC-derived coding sequences, or alternatively, may be sequences which have undergone site-specific mutations to generate one or more mutations in the oligonucleotide sequence. The ability of such polynucleotides to specifically hybridize to the corresponding MORC-specific mRNA sequences lend them particular utility in a variety of embodiments, including means for altering the MORC activity in a cell, means for inhibiting the translation of MORC-specific mRNA, and means for detecting MORC message in a cell, as well as a transformed host cell comprising one or more MORC compositions, a transgenic non-human mammal, and in the in vivo therapy of an animal and human disease resulting in elevated MORC activity.

The oligonucleotide sequences of the invention will also find particular utility as the basis for diagnostic hybridization assays for detecting MORC-specific RNA or DNA in clinical samples. Exemplary clinical samples that can be assayed for the presence of MORC or MORC-encoding mRNAs or DNAs include, but are not limited to, blood, serum, plasma, lymph, middle ear fluids, cerebrospinal fluid, sputum, bronchoalveolar fluid and the like. Such samples may be of mammalian origins, and in particular, or human, murine, equine, bovine, feline, porcine, or canine origin. A variety of hybridization techniques and systems are known that can be used in connection with the hybridization aspects of the invention, including diagnostic assays such as those described in U.S. Pat. No. 4,358,535, incorporated herein by reference. Samples derived from non-human mammalian sources, including animals of economic significance such as domestic farm animals, may also provide the basis for clinical specimens.

Accordingly, the nucleotide sequences of the invention are important for their ability to selectively form duplex molecules with complementary stretches of the nucleic acid segments encoding MORC epitopes. Depending on the application envisioned, one will desire to employ varying conditions of hybridization to achieve varying degrees of selectivity of the probe toward the target sequence. For applications requiring a high degree of selectivity, one will typically desire to employ relatively stringent conditions to form the hybrids. These conditions are particularly selective, and tolerate little, if any, mismatch between the probe and the template or target strand.

Of course, for some applications, for example, where one desires to prepare mutants employing a mutant primer strand hybridized to an underlying template, less stringent hybridization conditions are called for in order to allow formation of the heteroduplex. In these circumstances, one may desire to employ lower or reduced stringency hybridization conditions. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, one may desire to employ nucleic acid probes to isolate variants from clone banks containing mutated MORC-encoding clones. In particular embodiments, mutant clone colonies growing on solid media that contain variants of the MORC-encoding gene sequence could be identified on duplicate filters using hybridization conditions and methods, such as those used in colony blot assays, to only obtain hybridization between probes containing sequence variants and nucleic acid sequence variants contained in specific colonies. In this manner, small hybridization probes containing short variant sequences of these genes may be utilized to identify those clones growing on solid media that contain sequence variants of the entire genes. These clones can then be grown to obtain desired quantities of the variant nucleic acid sequences or the corresponding antigens.

In clinical and certain diagnostic embodiments, polynucleotide sequences of the present invention are used in combination with an appropriate means, such as a label, for determining hybridization. A wide variety of appropriate indicator means are known in the art, including radioactive, enzymatic or other ligands, such as avidin/biotin, that are capable of giving a detectable signal. In preferred diagnostic embodiments, one will likely desire to employ an enzyme tag such as urease, alkaline phosphatase or peroxidase, instead of radioactive or other environmentally undesirable reagents. In the case of enzyme tags, colorimetric indicator substrates are known that can be employed to provide a means visible to the human eye or spectrophotometrically, to identify specific hybridization with pathogen nucleic acid-containing samples.

In general, it is envisioned that the hybridization probes described herein will be useful both as reagents in solution hybridizations as well as in embodiments employing a solid phase. In embodiments involving a solid phase, the test DNA (or RNA) from suspected clinical samples, such as exudates, body fluids (e.g., middle ear effusion, bronchoalveolar lavage fluid) or even tissues, is adsorbed or otherwise affixed to a selected matrix or surface. This fixed, nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantified, by means of the label.

4.8 Peptide Nucleic Acid Compositions

In certain embodiments, the inventors contemplate the use of peptide nucleic acids (PNAs) in the practice of the methods of the invention. PNA is a DNA mimic in which the nucleobases are attached to a pseudopeptide backbone (Good and Nielsen, 1997). PNA is able to be utilized in a number methods that traditionally have used RNA or DNA. Often PNA sequences perform better in techniques than the corresponding RNA or DNA sequences and have utilities that are not inherent to RNA or DNA. An excellent review of PNA including methods of making, characteristics of, and methods of using, is provided by Corey (1997) and is incorporated herein by reference. As such, in certain embodiments, one may prepare PNA sequences that are homologous to, identical to, or complementary to one or more portions of the MORC polynucleotide sequences disclosed herein, and such PNA compositions may be used in any of the embodiments in which polynucleotide compositions may be used. For example, to regulate, alter, decrease, or reduce the translation of MORC-specific mRNA, and thereby alter the level of MORC activity in a host cell to which such PNA compositions have been administered, or to detect the presence of MORC-specific sequences via hybridization, or to prepare primers for amplification or mutagenesis procedures, or for preparing polynucleotide compositions for pharmaceutical formulations.

4.8.1 Methods of Making PNAs

PNAs have 2-aminoethyl-glycine linkages replacing the normal phosphodiester backbone of DNA (Nielsen et al., 1991; Hanvey et al., 1992; Hyrup and Nielsen, 1996; Neilsen, 1996). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Boc (Dueholm et al., 1994) or Fmoc (Thomson et al., 1995) protocols for solid-phase peptide synthesis, although other methods, including a modified Merrifield method, have been used (Christensen et al., 1995).

PNA monomers or ready-made oligomers are commercially available from PerSeptive Biosystems (Framingham, Mass., USA). PNA syntheses by either Boc or Fmoc protocols are straightforward using manual or automated protocols (Norton et al., 1995). The manual protocol lends itself to the production of chemically modified PNAs or the simultaneous synthesis of families of closely related PNAs.

As with peptide synthesis, the success of a particular PNA synthesis will depend on the properties of the chosen sequence. For example, while in theory PNAs can incorporate any combination of nucleotide bases, the presence of adjacent purines can lead to deletions of one or more residues in the product. In expectation of this difficulty, it is suggested that, in producing PNAs with adjacent purines, one should repeat the coupling of residues likely to be added inefficiently. This should be followed by the purification of PNAs by reverse-phase high-pressure liquid chromatography (Norton et al., 1995) providing yields and purity of product similar to those observed during the synthesis of peptides.

Modifications of PNAs for a given application may be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (Norton et al., 1995; Haaima et al., 1996; Stetsenko et al., 1996; Petersen et al., 1995; Orum et al., 1995; Footer et al., 1996; Griffith et al., 1995; Pardridge et al., 1995; Boffa et al., 1995; Lansdorp et al., 1996; Gambacorti-Passerini et al., 1996; Armitage et al., 1997; Seeger et al., 1997; Rusckowski et al., 1997). U.S. Pat. No. 5,700,922 discusses PNA-DNA-PNA chimeric molecules and their uses in diagnostics, modulating protein in organisms, and treatment of conditions susceptible to therapeutics.

4.8.2 Physical Properties of PNAs

In contrast to DNA and RNA, which contain negatively charged linkages, the PNA backbone is neutral. In spite of this dramatic alteration, PNAs recognize complementary DNA and RNA by Watson-Crick pairing (Egholm et al., 1993), validating the initial modeling by Nielsen et al. (1991). PNAs lack 3' to 5' polarity and can bind in either parallel or antiparallel fashion, with the antiparallel mode being preferred (Egholm et al., 1993).

Hybridization of DNA oligonucleotides to DNA and RNA is destabilized by electrostatic repulsion between the negatively charged phosphate backbones of the complementary strands. By contrast, the absence of charge repulsion in PNA-DNA or PNA-RNA duplexes increases the melting temperature ($T_m$) and reduces the dependence of $T_m$ on the concentration of mono- or divalent cations (Nielsen et al., 1991). The enhanced rate and affinity of hybridization are significant because they are responsible for the surprising ability of PNAs to perform strand invasion of complementary sequences within relaxed double-stranded DNA. In addition, the efficient hybridization at inverted repeats suggests that PNAs can recognize secondary structure effectively within double-stranded DNA. Enhanced recognition also occurs with PNAs immobilized on surfaces, and Wang et al. have shown that support-bound PNAs can be used to detect hybridization events (Wang et al., 1997).

One might expect that tight binding of PNAs to complementary sequences would also increase binding to similar (but not identical) sequences, reducing the sequence specificity of PNA recognition. As with DNA hybridization, however, selective recognition can be achieved by balancing oligomer length and incubation temperature. Moreover, selective hybridization of PNAs is encouraged by PNA-DNA hybridization being less tolerant of base mismatches than DNA-DNA hybridization. For example, a single mismatch within a 16 bp PNA-DNA duplex can reduce the $T_m$ by up to 15° C. (Egholm et al., 1993). This high level of discrimination has allowed the development of several PNA-based strategies for the analysis of point mutations (Wang et al., 1997; Carlsson et al., 1996; Thiede et al., 1996; Webb and Hurskainen, 1996; Perry-O'Keefe et al, 1996).

High-affinity binding provides clear advantages for molecular recognition and the development of new applications for PNAs. For example, 11–13 nucleotide PNAs inhibit the activity of telomerase, a ribonucleo-protein that extends telomere ends using an essential RNA template, while the analogous DNA oligomers do not (Norton et al., 1996).

Neutral PNAs are more hydrophobic than analogous DNA oligomers, and this can lead to difficulty solubilizing them at neutral pH, especially if the PNAs have a high purine content or if they have the potential to form secondary structures. Their solubility can be enhanced by attaching one or more positive charges to the PNA termini (Nielsen et al., 1991).

4.8.3 Applications of PNAS

Findings by Allfrey and colleagues suggest that strand invasion will occur spontaneously at sequences within chromosomal DNA (Boffa et al., 1995; Boffa et al., 1996). These studies targeted PNAs to triplet repeats of the nucleotides CAG and used this recognition to purify transcriptionally active DNA (Boffa et al., 1995) and to inhibit transcription (Boffa et al., 1996). This result suggests that if PNAs can be delivered within cells then they will have the potential to be general sequence-specific regulators of gene expression. Studies and reviews concerning the use of PNAs as antisense and anti-gene agents include Nielsen et al. (1993b), Hanvey et al. (1992), and Good and Nielsen (1997). Koppelhus et al. (1997) have used PNAs to inhibit HIV-1 inverse transcription, showing that PNAs may be used for antiviral therapies.

Methods of characterizing the antisense binding properties of PNAs are discussed in Rose (1993) and Jensen et al. (1997). Rose uses capillary gel electrophoresis to determine binding of PNAs to their complementary oligonucleotide, measuring the relative binding kinetics and stoichiometry. Similar types of measurements were made by Jensen et al. using BIAcore™ technology.

Other applications of PNAs include use in DNA strand invasion (Nielsen et al., 1991), antisense inhibition (Hanvey et al., 1992), mutational analysis (Orum et al., 1993), enhancers of transcription (Mollegaard et al., 1994), nucleic acid purification (Orum et al., 1995), isolation of transcriptionally active genes (Boffa et al., 1995), blocking of transcription factor binding (Vickers et al., 1995), genome cleavage (Veselkov et al., 1996), biosensors (Wang et al., 1997), in situ hybridization (Thisted et al., 1996), and in a alternative to Southern blotting (Perry-O'Keefe, 1996).

4.9 Methods of Nucleic Acid Delivery and DNA Transfection

In certain embodiments, it is contemplated that one or more RNA, DNA, PNAs and/or substituted polynucleotide compositions disclosed herein will be used to transfect an appropriate host cell. Technology for introduction of PNAs, RNAs, and DNAs into cells is well-known to those of skill in the art.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Wong and Neumann, 1982; Fromm et al., 1985; Tur-Kaspa et al., 1986; Potter et al., 1984; Suzuki et al., 1998; Vanbever et al., 1998), direct microinjection (Capecchi, 1980; Harland and Weintraub, 1985), DNA-loaded liposomes (Nicolau and Sene, 1982; Fraley et al., 1979; Takura, 1998) and lipofectamine-DNA complexes, cell sonication (Fechheimer et al., 1987), gene bombardment using high velocity microprojectiles (Yang et al., 1990; Klein et al., 1992), and receptor-mediated transfection (Curiel et al., 1991; Wagner et al., 1992; Wu and Wu, 1987; Wu and Wu, 1988). Some of these techniques may be successfully adapted for in vivo or ex vivo use.

Moreover, the use of viral vectors (Lu et al., 1993; Eglitis and Anderson, 1988; Eglitis et al., 1988), including retroviruses, baculoviruses, adenoviruses, adenoassociated viruses, vaccinia viruses, Herpes viruses, and the like are well-known in the art, and are described in detail herein.

4.10 Protein Isolation and Purifacation

In certain embodiments it may be desirable to purify MORC polypeptides, MORC epitopes, MORC-derived peptide fragments, or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1973; Capaldi et al., 1974; Capaldi et al., 1977). It will therefore be appreciated that under differing electrophoresis conditions, the apparent molecular weights of purified or partially purified expression products may vary.

High performance liquid chromatography (HPLC) is characterized by a very rapid separation with extraordinary resolution of peaks. This is achieved by the use of very fine particles and high pressure to maintain an adequate flow rate. Separation can be accomplished in a matter of min, or at most an h. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and Helix pomatia lectin. Lectins themselves are purified using affinity chromatography with carbohydrate ligands. Lactose has been used to purify lectins from castor bean and peanuts; maltose has been useful in extracting lectins from lentils and jack bean; N-acetyl-D-galactosamine is used for purifying lectins from soybean; N-acetylglucosamine binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

4.11 Synthetic MORC and MORC-Derived Peptides

To achieve certain objectives of the invention, it may be desirable to prepare one or more MORC-derived peptides and polypeptide fragments for use in various diagnostic and therapeutic applications. Because of their relatively small size, MORC-derived peptides and smaller polypeptide fragments obtained from MORC polypeptides may be proteolytically prepared from larger MORC polypeptides, or alternatively synthesized either partially or totally de novo in accordance with one of the many conventional techniques of protein and peptide synthesis, such as for example, in solution or on a solid support. Various automatic synthesizers are commercially available and can be used in accordance with known protocols. See, for example, Stewart and Young, (1966); Voss et al., (1983); Merrifield, (1986); and Barany and Merrifield (1979), each incorporated herein by reference. Short peptide sequences, or libraries of overlapping peptides, usually from about 6 or so amino acids, and up to and including about 35 to 50 or so amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

4.12 MORC-derived Antigen Compositions

The present invention also provides for the use of MORC proteins or peptides as antigens for the immunization of animals relating to the production of antibodies. It is envisioned that either MORC, or portions thereof, will be coupled, bonded, bound, conjugated or chemically-linked to one or more agents via linkers, polylinkers or derivatized amino acids. This may be performed such that a bispecific or multivalent composition or vaccine is produced. It is further envisioned that the methods used in the preparation of these compositions will be familiar to those of skill in the art and should be suitable for administration to animals, i.e., pharmaceutically acceptable. Preferred agents are the carriers are keyhole limpet hemocyannin (KLH) or bovine serum albumin (BSA).

4.13 Expression Vectors

The present invention contemplates an expression vector comprising at least one polynucleotide of the present invention. Such polynucleotides may comprise all or part of a sequence region encoding a MORC peptide or a MORC polypeptide, or alternatively, may be constructed with a specific DNA molecule oriented in an antisense direction to produce an RNA sequence which is complementary to, and specifically binds to, a MORC-specific mRNA. Alternatively, the MORC coding region or gene may be operably linked to a homologous or heterologous promoter that is expressible in a host cell, such as a prokaryotic (and in particular, bacterial) host cell, or an eukaryotic (and in particular, animal, fungal, or plant) host cell. In such embodiments, one or more promoter(s), either alone or in combination with one or more enhancer elements or other expression elements may be operatively linked to a sequence region that encodes a functional RNA such as an mRNA, a tRNA, an antisense mRNA, or a ribozyme.

As used herein, the term "operatively linked" means that a promoter is connected to a sequence that encodes a functional RNA in such a way that the transcription of that functional RNA is controlled and regulated by that promoter. Means for operatively linking a promoter to a functional RNA are well known in the art.

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the functional RNA to which it is operatively linked.

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

A variety of methods have been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

4.14 Transgenic Animals Comprising MORC-specific Compositions

It is contemplated that in some instances the genome of a transgenic non-human animal of the present invention will have been altered through the stable introduction of one or more of the MORC polynucleotide compositions described herein, either native, synthetically modified, or mutated, full-length, truncated, or oligonucleotide primers, antisense molecules, or derivatives thereof. As used herein, the term "transgenic animal" is intended to refer to an animal that has incorporated exogenous DNA sequences into its genome. In designing a heterologous gene for expression in animals, sequences which interfere with the efficacy of gene expression, such as polyadenylation signals, polymerase II termination sequences, hairpins, consensus splice sites and the like, are eliminated. Current advances in transgenic approaches and techniques have permitted the manipulation of a variety of animal genomes via gene addition, gene deletion, or gene modifications (Franz et al., 1997). For example, mosquitos (Fallon, 1996), trout (Ono et al., 1997), zebrafish (Caldovic and Hackett, 1995), pigs (Van Cott et al., 1997) and cows (Haskell and Bowen, 1995), are just a few of the many animals being studied by transgenics.

The creation of transgenic animals that express human proteins such as α-1-antitrypsin, in sheep (Carver et al., 1993); decay accelerating factor, in pigs (Cozzi et al., 1997); and plasminogen activator, in goats (Ebert et al., 1991) have previously been demonstrated. The transgenic synthesis of human hemoglobin (U.S. Pat. No. 5,602,306) and fibrinogen (U.S. Pat. No. 5,639,940) in non-human animals have also been disclosed, each specifically incorporated herein by reference in its entirety. Further, transgenic mice and rat models have recently been described as new directions to study and treat cardiovascular diseases such as hypertension in humans (Franz et al., 1997; Pinto-Siestma and Paul, 1997). The construction of a transgenic mouse model has recently been used to assay potential treatments for Alzheimer's disease (U.S. Pat. No. 5,720,936, specifically incorporated herein by reference in its entirety). It is contemplated in the present invention that transgenic animals contribute valuable information as models for studying the effects of MORC polypeptide and polynucleotide compositions.

4.15 Antisense Oligonucleotides Targeted to MORC mRNAS

In certain embodiments it may be desirable to regulate or alter the expression of MORC in a host cell by means of an antisense construct that specifically binds to a MORC-specific mRNA and alters translation of the mRNA into functional MORC polypeptide. The targeting of antisense oligonucleotides that specifically bind mRNA is an important means for altering protein synthesis in vivo. For example, the synthesis of polygalactauronase and the muscarine type 2 acetylcholine receptor are inhibited by antisense oligonucleotides directed to their respective mRNA sequences (U.S. Pat. No. 5,739,119 and U.S. Pat. No. 5,759,829, each specifically incorporated herein by reference in its entirety). Further, examples of antisense inhibition have been demonstrated with the nuclear protein cyclin, the multiple drug resistance gene (MDG1), ICAM-1, E-selectin, STK-1, striatal $GABA_A$ receptor and human EGF (Jaskulski et al., 1988; Vasanthakumar and Ahmed, 1989; Peris et al., 1998; U.S. Pat. No. 5,801,154; U.S. Pat. No. 5,789,573; U.S. Pat. No. 5,718,709 and U.S. Pat. No. 5,610,288, each specifically incorporated herein by reference in its entirety). Antisense constructs have also been described that inhibit and can be used to treat a variety of abnormal cellular proliferations, e.g. cancer (U.S. Pat. No. 5,747,470; U.S. Pat. No. 5,591,317 and U.S. Pat. No. 5,783,683, each specifically incorporated herein by reference in its entirety).

As used herein, the letters, A, G, C, T, and U respectively indicate nucleotides in which the nucleoside is Adenosine (Ade), Guanosine (Gua), Cytidine (Cyt), Thymidine (Thy), and Uridine (Ura). As used in the specification and claims, compounds that are antisense to the MORC DNA or mRNA sense strand are compounds which have a nucleoside sequence complementary to the sense strand. Table 3 shows the four possible sense strand nucleosides and their complements present in an antisense compound.

TABLE 3

| Sense | Antisense |
| --- | --- |
| Ade | Thy |
| Gua | Cyt |
| Cyt | Gua |
| Thy | Ade |
| Ura | Ade |

It will be understood by those skilled in the art that the present invention broadly includes oligonucleotide compounds which are capable of binding to the sense strand encoding a marnmalian MORC polypeptide. Thus, the invention includes compounds which are not strictly antisense: the compounds may have some non-complementary bases provided such compound have sufficient binding affinity for MORC mRNA to inhibit or otherwise alter expression and/or translation of the mRNA into functional MORC polypeptide.

In some cases, mutant polypeptides may not be non-functional. Rather, they may have aberrant functions that cannot be overcome by replacement gene therapy, even where the "wild-type" molecule is expressed in amounts in excess of the mutant polypeptide. Therefore, an important aspect of the invention concerns the preparation and use of MORC antisense constructs. Such antisense technology may be used to "knock-out" or reduce the function or expression of MORC in a cell, or may ablate the function of MORC in the development of cell line or in a transgenic mouse or other animal used in research, or diagnostic and/or screening methods.

The methodology for antisense techniques is well-known to molecular biologists. In a general sense, antisense methods take advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense-constructs will include regions complementary to intron/exon splice junctions. Thus, it is proposed that a preferred embodiment includes an antisense construct with complementarity to regions within 50–200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology as well as non-homologous regions (e.g., ribozyme) could be designed. These molecules, though having less than 50% homology, would bind to target sequences under appropriate conditions. The preparation and use of such ribozymes are described in detail in the following section.

In some circumstances, it may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

4.16 Ribozymes

Another embodiment of the invention concerns the formulation of and methods of using ribozymes. Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 (specifically incorporated herein by reference) reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., 1992). Thus, the specificity of action of a ribozyme is greater than that of an antisense oligonucleotide binding the same RNA site.

The enzymatic nucleic acid molecule may be formed in a hammerhead, hairpin, a hepatitis δ virus, group I intron or RNaseP RNA (in association with an RNA guide sequence) or Neurospora VS RNA motif. Examples of hammerhead motifs are described by Rossi et al. (1992). Examples of hairpin motifs are described by Hampel et al. (Eur. Pat. Appl. Publ. No. EP 0360257), Hampel and Tritz (1989), Hampel et al. (1990) and U.S. Pat. No. 5,631,359 (specifically incorporated herein by reference). An example of the hepatitis δ virus motif is described by Perrotta and Been (1992); an example of the RNaseP motif is described by Guerrier-Takada et al. (1983); Neurospora VS RNA ribozyme motif is described by Collins (Saville and Collins, 1990; Saville and Collins, 1991; Collins and Olive, 1993); and an example of the Group I intron is described in (U.S. Pat. No. 4,987,071, specifically incorporated herein by reference). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

In certain embodiments, it may be important to produce enzymatic cleaving agents which exhibit a high degree of specificity for the RNA of a desired target, such as one of the sequences disclosed herein. The enzymatic nucleic acid molecule is preferably targeted to a highly conserved sequence region of a target mRNA. Such enzymatic nucleic acid molecules can be delivered exogenously to specific cells as required. Alternatively, the ribozymes can be expressed from DNA or RNA vectors that are delivered to specific cells.

Small enzymatic nucleic acid motifs (e.g., of the hammerhead or the hairpin structure) may also be used for exogenous delivery. The simple structure of these molecules increases the ability of the enzymatic nucleic acid to invade targeted regions of the mRNA structure. Alternatively, catalytic RNA molecules can be expressed within cells from eukaryotic promoters (e.g., Scanlon et al., 1991; Kashani-Sabet et al., 1992; Dropulic et al., 1992; Weerasinghe et al., 1991; Ojwang et al., 1992; Chen et al., 1992; Sarver et al., 1990). Those skilled in the art realize that any ribozyme can be expressed in eukaryotic cells from the appropriate DNA vector. The activity of such ribozymes can be augmented by their release from the primary transcript by a second ribozyme (Int. Pat. Appl. Publ. No. WO 93/23569, and Int. Pat. Appl. Publ. No. WO 94/02595, both hereby incorporated by reference; Ohkawa et al., 1992; Taira et al., 1991; and Ventura et al., 1993).

Ribozymes may be added directly, or can be complexed with cationic lipids, lipid complexes, packaged within liposomes, or otherwise delivered to target cells. The RNA or RNA complexes can be locally administered to relevant tissues ex vivo, or in vivo through injection, aerosol inhalation, infusion pump or stent, with or without their incorporation in biopolymers.

Ribozymes may be designed as described in Int. Pat. Appl. Publ. No. WO 93/23569 and Int. Pat. Appl. Publ. No. WO 94/02595, each specifically incorporated herein by reference) and synthesized to be tested in vitro and in vivo, as described. Such ribozymes can also be optimized for delivery. While specific examples are provided, those in the art will recognize that equivalent RNA targets in other species can be utilized when necessary.

Hammerhead or hairpin ribozymes may be individually analyzed by computer folding (Jaeger et al., 1989) to assess whether the ribozyme sequences fold into the appropriate secondary structure. Those ribozymes with unfavorable intramolecular interactions between the binding arms and the catalytic core are eliminated from consideration. Varying binding arm lengths can be chosen to optimize activity. Generally, at least 5 or so bases on each arm are able to bind to, or otherwise interact with, the target RNA.

Ribozymes of the hammerhead or hairpin motif may be designed to anneal to various sites in the mRNA message, and can be chemically synthesized. The method of synthesis used follows the procedure for normal RNA synthesis as described in Usman et al., (1987) and in Scaringe et al. (1990) and makes use of common nucleic acid protecting and coupling groups, such as dimethoxytrityl at the 5'-end, and phosphoramidites at the 3'-end. Average stepwise coupling yields are typically >98%. Hairpin ribozymes may be synthesized in two parts and annealed to reconstruct an active ribozyme. (Chowrira and Burke, 1992). Ribozymes may be modified extensively to enhance stability by modification with nuclease resistant groups, for example, 2'-amino, 2'-C-allyl, 2'-flouro, 2'-o-methyl, 2'-H (for a review see e.g., Usman and Cedergren, 1992). Ribozymes may be purified by gel electrophoresis using general methods or by high pressure liquid chromatography and resuspended in water.

Ribozyme activity can be optimized by altering the length of the ribozyme binding arms, or chemically synthesizing ribozymes with modifications that prevent their degradation by serum ribonucleases (see e.g., Int. Pat. Appl. Publ. No. WO 92/07065; Perrault et al, 1990; Pieken et al., 1991; Usman and Cedergren, 1992; Int. Pat. Appl. Publ. No. WO 93/15187; Int. Pat. Appl. Publ. No. WO 91/03162; Eur. Pat.

Appl. Publ. No. 92110298.4; U.S. Pat. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Sullivan et al. (Int. Pat. Appl. Publ. No. WO 94/02595) describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Int. Pat. Appl. Publ. No. WO 94/02595 and Int. Pat. Appl. Publ. No. WO 93/23569, each specifically incorporated herein by reference.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells (Elroy-Stein and Moss, 1990; Gao and Huang, 1993; Lieber et al., 1993; Zhou et al., 1990). Ribozymes expressed from such promoters can function in mammalian cells (e.g. Kashani-Saber et al., 1992; Ojwang et al., 1992; Chen et al., 1992; Yu et al., 1993; L'Huillier et al., 1992; Lisziewicz et al., 1993). Such transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

Ribozymes of this invention may be used as diagnostic tools to examine genetic drift and mutations within diseased cells. They can also be used to assess levels of the target RNA molecule. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These studies will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNA associated with an IL-5 related condition. Such RNA is detected by determining the presence of a cleavage product after treatment with a ribozyme using standard methodology.

4.17 Vectors for Cloning, Gene Transfer and Expression

In certain embodiments of the invention, expression vectors are employed to express a MORC or MORC-derived polypeptide product, which can then be purified and, for example, be used to vaccinate animals, or to generate antisera or monoclonal antibodies which may be used in a variety of diagnostic and therapeutic applications. In other embodiments, an expression vector comprising a MORC or MORC-derived polynucleotide may be used in gene therapy.

Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

4.17.1 Regularity Elements

Throughout this application, the term "expression construct" is meant to include any type of genetic construct containing a nucleic acid coding for a gene product in which part or all of the nucleic acid encoding sequence is capable of being transcribed. Preferably, such a sequence encodes all or part of a gene which encodes a MORC polypeptide. The transcript may be translated into a protein, but it need not be. In certain embodiments, expression includes both transcription of a gene and translation of mRNA into a gene product. In other embodiments, expression only includes transcription of the nucleic acid encoding a gene of interest.

In preferred embodiments, the nucleic acid encoding a MORC polypeptide may be placed under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter employed to control the expression of a nucleic acid sequence of interest is not believed to be important, so long as it is capable of direction the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of the gene product. A variety of elements/promoters which are well-known to those of skill in the art may be employed in the context of the present invention to regulate expression of a MORC gene construct.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

4.17.2 Selectable Markers

In certain embodiments of the invention, a host cell transformed with one or more MORC nucleic acid segments may be identified in vitro or in vivo by including a "marker" or "reporter" gene in the expression construct and/or vector which comprises the MORC polynucleotide. Such reporter or marker would confer an identifiable change to the cell permitting easy identification of cells containing the expression construct. For example, the inclusion of a drug selection marker aids in cloning and in the selection of transformants. Genes that confer resistance to neomycin, puromycin, hygromycin, DHFR, GPT, zeocin and histidinol are often employed as selectable markers. Alternatively, enzymes such as herpes simplex virus thymidine kinase (tk) or chloramphenicol acetyltransferase (CAT) may also be employed, as well as one or more immunologic markers.

The selectable marker employed is not believed to be important, so long as it is capable of being expressed simultaneously with the nucleic acid encoding a gene product. Further examples of selectable markers are well known to one of skill in the art.

4.17.3 Multigene Constructs and IRES

In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Samow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

4.17.4 Delivery of Expression Vectors

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986).

One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Generation and propagation of adenovirus vectors, which are replication deficient, depend on a unique helper cell line, designated 293, which was transformed from human embryonic kidney cells by AdS DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Rich et al. 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Methods for culturing 293 cells and propagating adenovirus have been described. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another. format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the *gag, pol*, and *env* genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975). A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact-sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al., recently introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et al.,. 1991).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. . Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In one embodiment, such expression constructs may be entrapped in a liposome, lipid complex, nanocapsule, or other formulation using one or more of the methods disclosed in Section 4.8. Also contemplated are lipofectamine-DNA complexes. For example, liposome-mediated nucleic acid delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Eur. Pat. Appl. Publ. No. EP 0360257, specifically incorporated herein by reference).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e. a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent T-cells.

Large scale suspension culture of mammalian cells in stirred tanks is a common method for production of recombinant proteins. Two suspension culture reactor designs are in wide use—the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

4.18 Diagnosing Cancers Involving MORC

The present inventors have determined that alterations in MORC are associated with malignancy. Therefore, a MORC polypeptide or a MORC gene may be employed as a diagnostic or prognostic indicator of cancer. More specifically, point mutations, deletions, insertions or regulatory perturbations relating to MORC may cause cancer or promote cancer development, cause or promoter tumor progression at a primary site, and/or cause or promote metastasis. Other phenomena associated with malignancy that may be affected by MORC expression include angiogenesis and tissue invasion.

One embodiment of the instant invention comprises a method for detecting variation in the expression of MORC. This may comprises determining that level of MORC or determining specific alterations in the expressed product. Obviously, this sort of assay has importance in the diagnosis of related cancers. Such cancer may involve cancers of the breast or ovaries, or alternatively, cancers involving the lung, liver, spleen, brain kidney, pancreas, small intestine, blood cells, lymph node, colon, endometrium, stomach, prostate, testicle, skin, head and neck, esophagus, bone marrow, blood or other tissue. In particular, the present invention relates to the diagnosis of germ cell cancers, especially of the testes.

The biological sample can be any tissue or fluid. Various embodiments include cells of the skin, muscle, facia, brain, prostate, breast, endometrium, lung, head & neck, pancreas, small intestine, blood cells, liver, testes, ovaries, colon, skin, stomach, esophagus, spleen, lymph node, bone marrow or kidney. Other embodiments include fluid samples such as peripheral blood, lymph fluid, ascites, serous fluid, pleural effusion, sputum, cerebrospinal fluid, lacrimal fluid, stool or urine.

Nucleic acid used is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given patient with a statistically significant reference group of normal patients and patients that have MORC-related pathologies. In this way, it is possible to correlate the amount or kind of MORC detected with various clinical states.

Various types of defects are to be identified. Thus, "alterations" should be read as including deletions, insertions, point mutations and duplications. Point mutations result in stop codons, frameshift mutations or amino acid substitutions. Somatic mutations are those occurring in non-germline tissues. Germ-line tissue can occur in any tissue and are inherited. Mutations in and outside the coding region also may affect the amount of MORC produced, both by altering the transcription of the gene or in destabilizing or otherwise altering the processing of either the transcript (mRNA) or protein.

A variety of different assays are contemplated in this regard, including but not limited to, fluorescent in situ hybridization (FISH), direct DNA sequencing, PFGE analysis Southern or Northern blotting, single-stranded conformation analysis (SSCA), RNAse protection assay, allele-specific oligonucleotide (ASO), dot blot analysis, denaturing gradient gel electrophoresis, RFLP and PCR-SSCP.

4.18.1 Primers and Probes

The term primer, as defined herein, is meant to encompass any nucleic acid that is capable of priming the synthesis of a nascent nucleic acid in a template-dependent process. Typically, primers are oligonucleotides from about ten to about fifteen base pairs in length or even longer sequences such as those from about twenty to about 30 base pairs or more in length, with even longer sequences be employed for certain applications. Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process.

In preferred embodiments, the probes or primers are labeled with radioactive species ($^{32}$P, $^{14}$C, $^{35}$S, $^{3}$H, or other label), with a fluorophore (rhodamine, fluorescein) or a chemiluminescent (luciferase).

4.18.2 Template Dependent Amplification Methods

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in its entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure (RT-PCR™) may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

Another method for amplification is the ligase chain reaction ("LCR"), disclosed in EPO No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[α-thio]-triphosphates in one strand of a restriction site may also be useful in the amplification of nucleic acids in the present invention, Walker et al., (1992).

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2,202,328, and in PCT Application No. PCT/US89/01025, each of which is incorporated herein by reference in its entirety, may be used in accordance with the present invention. In the former application, "modified" primers are used in a PCR-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989; Int. Pat. Appl. Publ. No. WO 88/10315, incorporated herein by reference in their entirety). In NASBA, the nucleic acids can be prepared: for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Eur. Pat. Appl. Publ. No. EP 329,822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR™" (Frohman, 1990; Ohara et al., 1989; each herein incorporated by reference in their entirety).

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu and Wang, (1989), incorporated herein by reference in its entirety.

4.18.3 Southern/Northern Blotting

Blotting techniques are well known to those of skill in the art. Southern blotting involves the use of DNA as a target, whereas Northern blotting involves the use of RNA as a target. Each provide different types of information, although cDNA blotting is analogous, in many aspects, to blotting or RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will binding a portion of the target sequence under renaturing conditions. Unbound probe is then removed, and detection is accomplished as described above.

4.18.4 Seration Methods

It normally is desirable, at one stage or another, to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989. Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder et al., 1968a, Freifelder et al., 1968b; Freifelder, 1982).

4.18.5 Detection Methods

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by a labeled probe. The techniques involved are well known to those of skill in the art and can be found in many standard books on molecular protocols (see Sambrook et al., 1989). For example, chromophore or radiolabel probes or primers identify the target during or following amplification. One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

In addition, the amplification products described above may be subjected to sequence analysis to identify specific kinds of variations using standard sequence analysis techniques. Within certain methods, exhaustive analysis of genes is carried out by sequence analysis using primer sets designed for optimal sequencing (Pignon et al, 1994). The present invention provides methods by which any or all of these types of analyses may be used. Using the sequences disclosed herein, oligonucleotide primers may be designed to permit the amplification of sequences throughout the MORC gene that may then be analyzed by direct sequencing.

4.18.6 Kit Components

All the essential materials and reagents required for detecting and sequencing MORC and variants thereof may be assembled together in a kit. This generally will comprise preselected primers and probes. Also included may be enzymes suitable for amplifying nucleic acids including various polymerases (RT, Taq, Sequenase™, etc.), deoxynucleotides and buffers to provide the necessary reaction mixture for amplification. Such kits also generally will comprise, in suitable means, distinct containers for each individual reagent and enzyme as well as for each primer or probe.

4.18.7 Relative Quantitative RT-PCR™

Reverse transcription (RT) of RNA to cDNA followed by relative quantitative PCR™ (RT-PCR™) can be used to determine the relative concentrations of specific mRNA species isolated from patients. By determining that the concentration of a specific mRNA species varies, it is shown that the gene encoding the specific mRNA species is differentially expressed.

In PCR™, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR™ amplification is directly proportional to the starting concentration of the target before the reaction began. By determining the concentration of the amplified products of the target DNA in PCR™ reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundance of the specific mRNA from which the target sequence was derived can be determined for the respective tissues or cells. This direct proportionality between the concentration of the PCR™ products and the relative mRNA abundance is only true in the linear range of the PCR™ reaction.

The final concentration of the target DNA in the plateau portion of the curve is determined by the availability of reagents in the reaction mix and is independent of the original concentration of target DNA. Therefore, the first condition that must be met before the relative abundance of a mRNA species can be determined by RT-PCR™ for a collection of RNA populations is that the concentrations of the amplified PCR™ products must be sampled when the PCR™ reactions are in the linear portion of their curves.

The second condition that must be met for an RT-PCR™ experiment to successfully determine the relative abundance of a particular mRNA species is that relative concentrations of the amplifiable cDNAs must be normalized to some independent standard. The goal of an RT-PCR™ experiment is to determine the abundance of a particular mRNA species relative to the average abundance of all mRNA species in the sample. In the studies described below, mRNAs for β-actin, asparagine synthetase and lipocortin II were used as external and internal standards to which the relative abundance of other mRNAs are compared.

Most protocols for competitive PCR™ utilize internal PCR™ standards that are approximately as abundant as the target. These strategies are effective if the products of the PCR™ amplifications are sampled during their linear phases. If the products are sampled when the reactions are approaching the plateau phase, then the less abundant product becomes relatively over represented. Comparisons of relative abundance made for many different RNA samples, such as is the case when examining RNA samples for differential expression, become distorted in such a way as to make differences in relative abundance of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR™ assay for clinically derived materials. The problems inherent in clinical samples are that they are of variable quantity (making normalization problematic), and that they are of variable quality (necessitating the co-amplification of a reliable internal control, preferably of larger size than the target). Both of these problems are overcome if the RT-PCR™ is performed as a relative quantitative RT-PCR™ with an internal standard in which the internal standard is an amplifiable cDNA fragment that is larger than the target cDNA fragment and in which the abundance of the mRNA encoding the internal standard is roughly 5–100 fold higher than the mRNA encoding the target. This assay measures relative abundance, not absolute abundance of the respective mRNA species.

Other studies may be performed using a more conventional relative quantitative RT-PCR™ assay with an external standard protocol. These assays sample the PCR™ products in the linear portion of their amplification curves. The number of PCR™ cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR™ assays can be superior to those derived from the relative quantitative RT-PCR™ assay with an internal standard.

One reason for this advantage is that without the internal standard/competitor, all of the reagents can be converted into a single PCR™ product in the linear range of the amplification curve, thus increasing the sensitivity of the assay. Another reason is that with only one PCR™ product, display of the product on an electrophoretic gel or another display method becomes less complex, has less background and is easier to interpret.

4.18.8 Chip Technologies

Specifically contemplated by the present inventors are chip-based DNA technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization. See also Pease et al. (1994); Fodor et al. (1991).

4.19 Methods for Screening Active Compounds

The present invention also contemplates the use of MORC and active fragments, and MORC nucleic acids, in the screening of compounds for activity in either stimulating MORC activity, overcoming the lack of MORC, or blocking the effect of a mutant MORC molecule. These assays may make use of a variety of different formats and may depend on the kind of "activity" for which the screen is being conducted. Contemplated functional "read-outs" include binding to a compound, inhibition of binding to a substrate, ligand, receptor or other binding partner by a compound, phosphatase activity, anti-phosphatase activity, phosphorylation of MORC, dephosphorylation of MORC, inhibition or stimulation of cell-to-cell signaling, growth, metastasis, cell division, cell migration, soft agar colony formation, contact inhibition, invasiveness, angiogenesis, apoptosis, tumor progression or other malignant phenotype.

4.19.1 In Vitro Assays

In one embodiment, the invention is to be applied for the screening of compounds that bind to the MORC molecule or fragment thereof. The polypeptide or fragment may be either free in solution, fixed to a support, expressed in or on the surface of a cell. Either the polypeptide or the compound may be labeled, thereby permitting determining of binding.

In another embodiment, the assay may measure the inhibition of binding of MORC to a natural or artificial substrate or binding partner. Competitive binding assays can be performed in which one of the agents (MORC, binding partner or compound) is labeled. Usually, the polypeptide will be the labeled species. One may measure the amount of free label versus bound label to determine binding or inhibition of binding. Alternatively, these techniques may be used to monitor an interaction between MORC and a polypeptide with which it interacts, such as the 123F2 polypeptide. Assays to characterize and monitor protein:protein interactions, particularly direct interactions, are well known to those of skill in the art, and some of these methods are described in other sections infra. Modulators of this interaction can be identified and characterized based on monitoring of the interaction in the presence and absence of a candidate modulator. Modulators may be involved in either a carcinogenesis pathway or spermatogenesis. Because 123F2 causes MORC to relocalize in the cytoplasm instead of the nucleus, modulators that interfere, for example, with this localization can also be identified. Their localizations can be determined using an epitope tag system in which a fusion protein is employed. A fusion protein can comprise all or part of the interacting protein and an epitope tag. The epitope tag may be, for example, FLAG, Green Fluorescent Protein (GFP), Histidine tag, hemagglutinin (HA), or c-myc. Antibodies to the epitope tag are then used to provide information about the polypeptide that is fused to the tag.

Another technique for high throughput screening of compounds is described in WO 84/03564. Large numbers of small peptide test compounds are synthesized on a solid substrate, such as plastic pins or some other surface. The peptide test compounds are reacted with MORC and washed. Bound polypeptide is detected by various methods.

Purified MORC can be coated directly onto plates for use in the aforementioned drug screening techniques. However, non-neutralizing antibodies to the polypeptide can be used to immobilize the polypeptide to a solid phase. Also, fusion proteins containing a reactive region (preferably a terminal region) may be used to link the MORC active region to a solid phase.

Various cell lines containing wild-type or natural or engineered mutations in MORC can be used to study various functional attributes of MORC and how a candidate compound affects these attributes. Methods for engineering mutations are described elsewhere in this document, as are naturally-occurring mutations in MORC that lead to, contribute to and/or otherwise cause malignancy. In such assays, the compound would be formulated appropriately, given its biochemical nature, and contacted with a target cell. Depending on the assay, culture may be required. The cell may then be examined by virtue of a number of different physiologic assays. Alternatively, molecular analysis may be performed in which the function of MORC, or related pathways, may be explored. This may involve assays such as those for protein expression, enzyme function, substrate utilization, phosphorylation states of various molecules including MORC, cAMP levels, mRNA expression (including differential display of whole cell or polyA RNA), polypeptide interactions, and others.

4.19.2 In Vivo Assays

The present invention also encompasses the use of various animal models. Here, the identity seen between human and mouse MORC provides an excellent opportunity to examine the function of MORC in a whole animal system where it is normally expressed. By developing or isolating mutant cells lines that fail to express normal MORC, one can generate cancer models in mice that will be highly predictive of cancers in humans and other mammals. These models may employ the orthotopic or systemic administration of tumor cells to mimic primary and/or metastatic cancers. Alternatively, one may induce cancers in animals by providing agents known to be responsible for certain events associated with malignant transformation and/or tumor progression. Finally, transgenic animals (discussed below) that lack a wild-type MORC may be utilized as models for cancer development and treatment.

Treatment of animals with test compounds will involve the administration of the compound, in an appropriate form, to the animal. Administration will be by any route the could be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply and intratumoral injection.

Determining the effectiveness of a compound in vivo may involve a variety of different criteria. Such criteria include, but are not limited to, survival, reduction of tumor burden or mass, arrest or slowing of tumor progression, elimination of tumors, inhibition or prevention of metastasis, increased activity level, improvement in immune effector function and improved food intake.

4.19.3 Rational Drug Design

The goal of rational drug design is to produce structural analogs of biologically active polypeptides or compounds with which they interact (agonists, antagonists, inhibitors, binding partners, etc.). By creating such analogs, it is possible to fashion drugs which are more active or stable than the natural molecules which have different susceptibility to alteration or which may affect the function of various other molecules. In one approach, one would generate a three-dimensional structure for MORC or a fragment thereof. This could be accomplished by x-ray crystallography, computer modeling or by a combination of both approaches. An alternative approach, "alanine scan," involves the random replacement of residues throughout molecule with alanine, and the resulting affect on function determined.

It also is possible to isolate a MORC-specific antibody, selected by a functional assay, and then solve its crystal structure. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

Thus, one may design drugs which have improved MORC activity or which act as stimulators, inhibitors, agonists, antagonists or MORC or molecules affected by MORC function. By virtue of the availability of cloned MORC sequences described herein, sufficient amounts of MORC can be produced to perform crystallographic studies. In addition, knowledge of the polypeptide sequences permits computer employed predictions of structure-function relationships.

4.20 Biological Functional Equivalents

In certain embodiments of the invention, one may desire to mutagenize a MORC polypeptide or polynucleotide to make a modification and/or change in the structure of the MORC proteins or DNA segments which encode them and still obtain a functional molecule that encodes a protein or peptide with desirable characteristics. The following is a discussion based upon changing the amino acids of a protein to create an equivalent, or even an improved, second-generation molecule. The amino acid changes may be achieved by changing the codons of the DNA sequence, according to the codons given in Table 4.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

TABLE 4

| Amino Acids | | | Codons | | | | |
|---|---|---|---|---|---|---|---|
| Alanine | Ala | A | GCA | GCC | GCG | GCU | |
| Cysteine | Cys | C | UGC | UGU | | | |
| Aspartic Acid | Asp | D | GAC | GAU | | | |
| Glutamic Acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG | CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); meth (+1.9); alanine (+1.8); glycine (+0.4); threonine (−0.7); serine (−0.8); tryptophan (−0.9); tyrosin (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids aving a similar hydropathic index or score and still result in a protein with similar biological activity, i.e., still obtain a biological functionally equivalent protein. In making such changes, he substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−4.0); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

4.21 Elisas and Immunoprecipitation

ELISAs may be used in conjunction with the invention. In an ELISA assay, proteins or peptides incorporating MORC polypeptide antigen sequences are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of milk powder. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immmune complex (antigen/antibody) formation. Such conditions preferably include diluting the antisera with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 h, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

Following formation of specific immunocomplexes between the test sample and the bound antigen, and subsequent washing, the occurrence and even amount of immunocomplex formation may be determined by subjecting same to a second antibody having specificity for the first. To provide a detecting means, the second antibody will preferably have an associated enzyme that will generate a color development upon incubating with an appropriate chromogenic substrate. Thus, for example, one will desire to contact and incubate the antisera-bound surface with a urease or peroxidase-conjugated anti-human IgG for a period of time and under conditions which favor the development of immunocomplex formation (e.g., incubation for 2 h at room temperature in a PBS-containing solution such as PBS Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectra spectrophotometer.

The anti-MORC polypeptide antibodies of the present invention are particularly useful for the isolation of other MORC polypeptide antigens by immunoprecipitation. Immunoprecipitation involves the separation of the target antigen component from a complex mixture, and is used to discriminate or isolate minute amounts of protein. For the isolation of membrane proteins cells must be solubilized into detergent micelles. Nonionic salts are preferred, since other agents such as bile salts, precipitate at acid pH or in the presence of bivalent cations.

In an alternative embodiment the antibodies of the present invention are useful for the close juxtaposition of two antigens. This is particularly useful for increasing the localized concentration of antigens, e.g. enzyme-substrate pairs.

4.22 Western Blots

The MORC compositions of the present invention will find great use in immunoblot or western blot analysis. The anti-MORC antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal.

Immunologically-based detection methods for use in conjunction with Western blotting include enzymatically-, radiolabel-, or fluorescently-tagged secondary antibodies against the toxin moiety are considered to be of particular use in this regard.

These various immunoassays can also be used to characterize protein:protein interactions and identify modulators of this interaction. For example, co-immunoprecipitations can be used to identify an interaction, while disruption of this interaction can be monitored such that modulators of the interaction can also be identified.

4.23 Definitions

The following words and phrases have the meanings set forth below: a, an: In keeping with long-standing patent tradition, "a" or "an" used throughout this disclosure is intended to mean "one or more."

Comprising, comprises: In keeping with long-standing patent tradition, "comprising" and "comprises" used throughout this disclosure is intended to mean "including, but not limited to."

Expression: The combination of intracellular processes, including transcription and translation undergone by a coding DNA molecule such as a structural gene to produce a polypeptide.

Promoter: A recognition site on a DNA sequence or group of DNA sequences that provide an expression control element for a structural gene and to which RNA polymerase specifically binds and initiates RNA synthesis (transcription) of that gene.

Structural gene: A gene that is expressed to produce a polypeptide.

Transformation: A process of introducing an exogenous DNA sequence (e.g., a vector, a recombinant DNA molecule) into a cell or protoplast in which that exogenous DNA is incorporated into a chromosome or is capable of autonomous replication.

Transformed cell: A cell whose DNA has been altered by the introduction of an exogenous DNA molecule into that cell.

Transgenic cell: Any cell derived or regenerated from a transformed cell or derived from a transgenic cell.

Vector: A DNA molecule capable of replication in a host cell and/or to which another DNA segment can be operatively linked so as to bring about replication of the attached segment. A plasmid is an exemplary vector.

4.24 Cancer Treatments

The MORC compositions of the present invention will be useful also in the treatment of cancer. The germ cells of a mouse that does not have a wild-type copy of both morc alleles undergo more apoptosis. Moreover, the MORC polypeptide interacts with the 123F2 polypeptide, which is a candidate tumor suppressor gene (Genbank Accession Numbers AF 1 32851 (*Mus musculus*) and AF040703 (*Homo sapiens*), both incorporated herein by reference). Thus, it is contemplated that the present invention has advantages for the treatment of cancer, and this can be combined with other anticancer agents such as those implemented into treatments involving chemotherapy, radiotherapy and immunotherapy.

The term "cancer cell" is used to indicate a cell whose growth is uncontrolled. The present invention covers treatment of tumors and cancers of the brain (glioblastoma, astrocytoma, oligodendroglioma, ependymomas), lung, liver, spleen, kidney, lymph node, pancreas, small intestine, colon, stomach, breast, endometrium, prostate, testicle, ovary, skin, head and neck, esophagus, bone marrow, blood and other tissue. The methods of the present invention are directed to a cancer treatment that confers a therapeutic benefit on the subject with cancer. The term "therapeutic benefit" used throughout this application refers to anything that promotes or enhances the well-being of the subject with respect to the medical treatment of his condition, which includes treatment of cancer. A list of nonexhaustive examples of a "therapeutic benefit" includes extension of the subject's life by any period of time, decrease or delay in the neoplastic development of the disease, decrease in growth or proliferation of cancer cells, reduction in tumor growth, delay or prevention of metastases, reduction in cancer cell or tumor cell proliferation rate, and a decrease in pain to the subject that can be attributed to the subject's condition.

Cancer cell resistance to anticancer agents represents a major problem in clinical oncology. To improve treatment, in the context of the present invention, it is contemplated that therapy with a MORC polypeptide can be used similarly in conjunction with anti-cancer agents, including chemo-, radio-, and immunotherapeutic intervention.

To kill cells, inhibit cell growth, inhibit metastasis, inhibit angiogenesis or otherwise reverse or reduce the malignant phenotype of cancer cells, using the methods and compositions of the present invention, one would generally contact a "target" cell with a MORC polypeptide, or a nucleic acid segment encoding a MORC polypeptide, and at least one other agent. These compositions would be provided in a combined amount effective to kill or inhibit proliferation of the cell. This process may involve contacting the cells with a MORC polypeptide and the agent(s) or factor(s) at the same time. This may be achieved by contacting the cell with a single composition or pharmacological formulation that includes both agents, or by contacting the cell with two distinct compositions or formulations, at the same time, wherein one composition includes the expression construct and the other includes the agent.

Alternatively, the gene therapy treatment may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either a MORC polypeptide (or its cognate nucleic acid segment) or the other agent will be desired. Various combinations may be employed, where the MORC polypeptide is "A" and the other agent is "B", as exemplified below:

A/B/A B/A/B B/B/A A/A/B B/A/A A/B/B B/B/B/A B/B/ A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Other combinations are contemplated. Again, to achieve cell killing, both agents are delivered to a cell in a combined amount effective to kill the cell.

Agents or factors suitable for use in a combined therapy are any chemical compound or treatment method with anticancer activity; therefore, the term "anticancer agent" that is used throughout this application refers to an agent with anticancer activity. These compounds or methods include alkylating agents, topoisomerase I inhibitors, topoisomerase II inhibitors, antitumor antibiotics, RNA/DNA antimetabolites, DNA antimetabolites, mitotic inhibitors, nitrosureas, corticosteroid hormones, as well as DNA damaging agents, which induce DNA damage when applied to a cell, and compounds used in immunotherapy, such as tumor-specific antibodies. Examples of alkylating agents include, inter alia, chloroambucil, cis-platinum, cyclodisone, flurodopan, methyl CCNU, piperazinedione, teroxirone. Topoisomerase I inhibitors encompass compounds such as camptothecin and camptothecin derivatives, as well as morpholinodoxorubicin. Doxorubicin, pyrazoloacridine, mitoxantrone, and rubidazone are illustrations of topoisomerase II inhibitors. RNA/DNA antimetabolites include L-alanosine, 5-fluoraouracil, aminopterin derivatives, methotrexate, and pyrazofurin; while the DNA antimetabolite group encompasses, for example, ara-C, guanozole, hydroxyurea, thiopurine. Typical mitotic inhibitors are colchicine, rhizoxin, taxol, and vinblastine sulfate. Other agents and factors include radiation and waves that induce DNA damage such as, y-irradiation, X-rays, UV-irradiation, microwaves, electronic emissions, and the like. A variety of anti-cancer agents, also described as "chemotherapeutic agents," function to induce DNA damage, all of which are intended to be of use in the combined treatment methods disclosed herein. Chemotherapeutic agents contemplated to be of use, include, e.g., adriamycin, bleomycin, 5-fluorouracil (5FU), etoposide (VP-16), camptothecin, actinomycin-D, mitomycin C, cisplatin (CDDP), podophyllotoxin, verapamil, and even hydrogen peroxide. The invention also encompasses the use of a combination of one or more anticancer agents with a MORC polypeptide.

Agents that directly cross-link nucleic acids, specifically DNA, are envisaged to facilitate DNA damage leading to a synergistic, anti-cancercombination with MORC. Cisplatinumagents such as cisplatin, and other DNA alkylating agents-may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally. Bleomycin and mitomycin C are other anticancer agents that are administered by injection intraveneously, subcutaneously, intratumorally or intraperitoneally. A typical dose of bleomycin is 10 mg/m$^2$, while such a dose for mitomycin C is 20 mg/m$^2$.

Agents that damage DNA also include compounds that interfere with DNA replication, mitosis and chromosomal segregation. Such chemotherapeutic compounds include adriamycin, also known as doxorubicin, etoposide, verapamil, podophyllotoxin,and the like. Widely used in a clinical setting for the treatment of neoplasms, these compounds are administered through bolus injections intravenously at doses ranging from 25–75 mg/m$^2$ at 21 day intervals for adriamycin, to 35–50 mg/m$^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the cancer cells.

The skilled artisan is directed to "Remington's Pharmaceutical Sciences" 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

In addition to combining MORC therapies with chemo- and radiotherapies, it also is contemplated that combination with other gene therapies will be advantageous. For example, implementing wild-type morc in combination with the targeting of p53 or p 16 mutations at the same time may produce an improved anti-cancer treatment. Any other tumor-related gene conceivably can be targeted in this manner, for example, p21, Rb, APC, DCC, NF-1, NF-2, BCRA2, p16, FHIT, WT-1, MEN-I, MEN-II, BRCA1, VHL, FCC, MCC, ras, myc, neu, raf erb, src, fms, jun, trk, ret, gsp, hst, bcl and abl. A therapeutic polynucleotide of the present invention, therefore, encompasses a polynucleotide that provides a medical advantage to the cell when administered. This could include, for example, a wild-type or dominant negative copy of any of the tumor-relatedgenes previously listed. Furthermore,this comprises providing a MORC polypeptide and a 123F2 polypeptide either simultaneously or sequentially in the treatment of cancer. For example, gene therapy to treat cancer could comprise providing a wild-type human morc gene and a wild-type human 123F2 gene to a patient. The combination treatments previously discussed encompass the use of at least one other therapy treatment in addition to treatment with MORC, but they are not limited to only one other treatment.

It also should be pointed out that any of the foregoing therapies may prove useful by themselves. In this regard, reference to chemotherapeutics and gene therapy in combination also should be read as a contemplation that these approaches may be employed separately.

5.0 EXAMPLES

The following examples are included to demonstrate preferred embodiments of the invention. It should be appreciated by those of skill in the art that the techniques disclosed in the examples which follow represent techniques discovered by the inventor to function well in the practice of the invention, and .thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Identification of the MORC (Microrchidm) Mutation

This example describes a new autosomal recessive mouse mutation that arrests germ cell evelopment in early meiotic prophase, prior to the pachytene stage, a critical phase of permatogenesis when events are initiated in preparation for the later segregation of meiotic chromosomes. The morc mutant phenotype is especially interesting since the inventors' results show that morc's biologic effects are restricted to male gametogenesis, in contrast to many other infertility mutations.

The *microrchidia*, or morc, autosomal recessive mutation results in the arrest of spermatogenesis early in prophase I of meiosis. The morc mutation arose spontaneously during the development of a mouse strain transgenic for a tyrosinase cDNA construct. Morc –/– males are infertile and have grossly reduced testicular mass, while –/– females are normal, indicating that the morc gene acts specifically during male gametogenesis. Immunofluorescence to synaptonemal complex antigens demonstrated that –/– male germ cells enter meiosis but arrest prior to the pachytene stage, and fail to progress beyond zygotene or leptotene stage, suggesting that morc may regulate early meiotic prophase events involving chromosome synapsis or recombination. An apoptosis assay revealed massive numbers of cells undergoing apoptosis in testes of –/– mice. No other abnormal phenotype was observed in mutant animals, with the exception of eye pigmentation due to transgene expression in the retina. Spermatogenesis is normal in +/– males, despite significant transgene expression in germ cells. Genomic analysis of –/– animals indicates the presence of a deletion adjacent to the transgene. These data indicate that morc sterility results from a deletion of all or part a gene required for progression of male germ cells through meiosis.

5.1.1 Origin of the Microrchidia Mutation

In order to generate a strain of mice in which coat color could be used to assay for subsequent cre-mediated recombination events, FVB/n fertilized eggs were injected with a mouse polII-loxP-tyrosinase construct that drives tyrosinase expression from an RNA polymerase II promoter.

FVB/n inbred mice were obtained from Harlan Laboratories (Houston, Tex.). The transgene construct included the mouse RNA polymerase II 5' regulatory region (GenBank # M14101, nt 1–712), a loxP recognition site (5'-GGAACCCTTAATATAACTTC GTATAATGTATGC-TATACGAAGTTATTAGGTCCCT CGAC-3'; SEQ ID NO:5) and the mouse tyrosinase coding region (GenBank # D00440 nt 1–1976) cloned into the BamHI site of pBluescript SK⁻. The insert was excised with NotI, purified and injected into male pronuclei using standard transgenesis protocols (Hogan et al., 1994).

In the single line produced, the transgene rescued eye pigmentation in a dosage-dependent fashion (wild-type (+/+)=pink; heterozygous transgenic (+/–)=brown; homozygous transgenic (–/–)=black), but coat color remained white regardless of genotype (FIG. 1A). Thus despite having a "ubiquitous" promoter, the transgene was expressed in a tissue-restricted fashion. The eye color phenotype was used advantageously as an indicator of genotype for crosses.

When F3 transgene-positive animals were mated, it became apparent that –/– males never sired any offspring, despite normal copulatory behavior. Test matings were set up between wild-type and +/– or –/– animals of both sexes. Homozygous or heterozygous transgenic females mated with wild-type FVB males gave birth to normal sized litters with the expected mendelian ratio of genotypes. Heterozygous males were also fertile, indicating that the infertility phenotype was recessive.

5.1.2 Description of the MORC –/– Phenotype

Mice were euthanized with $CO_2$ and weights obtained for total body, testes and epididymides. One-way analysis of variance (ANOVA) was used to test whether the testes weights differed significantly for mice of different genotypes.

At autopsy, testes of homozygous (–/–) males were grossly smaller than testes of wild type (+/+) or heterozygous (+/–) animals (FIG. 1B, FIG. 8). Table 5 shows the adult testes and epididymides (Epi) weights (mean±sd) with ratio to body mass (Bm) for six week old wild type (+/+), heterozygous (+/–), and homozygous (–/–) morc mice, with n representing the number of animals analyzed. On average, –/– testes weighed less than one third as much as those of +/+ FVB mice (Table 5). By contrast, other urogenital structures such as the epididymides were normal (Table 5). Careful necropsy revealed no other gross abnormalities. The mutation was thus named microrchidia, a medical term for abnormally small testes. Testes from older +/– (but not +/+ or –/–) animals displayed a faint brown pigmentation, probably due to tyrosinase expression (FIG. 1B, FIG. 9).

TABLE 5

| Geno-type | Testes weight (mg) | n | Epididymides weight (mg) | n | Body mass (g) | n | Testes/Bm ($10^{-3}$) | n | Epi/Bm ($10^{-3}$) | n |
|---|---|---|---|---|---|---|---|---|---|---|
| +/+ | 163.17 ± 19.35 | 15 | 63.53 ± 18.38 | 14 | 23.40 ± 2.85 | 15 | 6.99 ± 0.61 | 15 | 2.72 ± 0.79 | 14 |
| +/− | 165.15 ± 30.65 | 35 | 69.46 ± 18.45 | 31 | 26.08 ± 3.81 | 31 | 6.36 ± 1.23 | 31 | 2.81 ± 0.55 | 27 |
| −/− | 44.30 ± 4.73 | 29 | 50.59 ± 7.65 | 19 | 23.88 ± 2.53 | 21 | 1.91 ± 0.23 | 21 | 2.16 ± 0.48 | 19 |

Next, histology was performed as follows. Tissues were immediately fixed in 10% buffered formalin or Bouin's fixative for 16 h at 4° C., followed by equilibration in 70% ethanol with standard processing and paraffin embedding. Five μm thick sections were stained with hematoxylin/eosin or periodic-acid Schiff-base for routine histology. For immuno-histochemistry, sections were deparaffinized, preblocked with rabbit serum, and treated with either anti-tyrosinase antibody (rabbit anti-peptide serum PEP7 [Jimenez et al., 1991]) at 1:1,000 dilution, rabbit control serum (1:1,000) or PBS alone (FIG. 10). Bound antibodies were detected with biotinylated goat anti-rabbit antibody (Vector Laboratories, Burlingame, Calif.), then streptavidin HRP (Vector) followed by chromagen development (diamino benzidine, SigmaFast #D-4293) for 5 min with final hematoxylin counterstain. Immunofluorescent detection of synaptonemal complex antigens was as previously described (Cobb et al., 1997), using polyclonal mouse antibodies anti-COR1, recognizing mouse SYCP3, and rabbit anti-SYN1, recognizing mouse SYCP1 (Dobson et al., 1994).

Histologic abnormalities in adult −/− males were striking. Sections from −/− epididymides revealed a complete absence of spermatozoa. In contrast, +/+ and +/− males had epididymides that were filled with spermatozoa. When seminiferous tubules from all three genotypes were examined, −/− males had marked abnormalities (FIG. 2B and FIG. 2D), whereas +/+ and +/− (FIG. 2A and FIG. 2C) males had normal testis histophenotype. Numerous cells in the adluminal compartment of mutants had hyperchromatic, condensed nuclei. These appeared to be pyknotic spermatocytes that had undergone degeneration during early prophase of meiosis I (FIG. 2D). No secondary spermatocytes or spermatids were ever seen in −/− animals. In 6 week old mice, spermatogonia were present in normal numbers and appeared to be actively undergoing mitoses. By age 6 months, the germinal epithelium of mutant mice contained only Sertoli cells, with no mature germ cells. This phenotype is reminiscent of the "Sertoli only" histophenotype seen in some sterile men (del Castillo et al., 1947; Girgis et al., 1969; Wong et al., 1973). The Leydig cells appeared to be increased in number in −/− mice, however, the hyperproliferation was accentuated by loss of germ cells. Comprehensive tissue surveys demonstrated that the sole histologic defect in −/− males was the germ cell maturation arrest. Females of all genotypes had normal ovarian histology.

To ascertain more precisely the stage of spermatogenic breakdown in morc −/− mice, the inventors investigated the assembly of components of the synaptonemal complex (SC), a structure unique to meiotic cells. Numerous cells from testes of −/− mice contained SC antigens, indicating definitively that mutant germ cells enter meiotic prophase. The inventors found mutant cells with characteristics of both the leptotene and zygotene stages of meiotic prophase, but none with the characteristics of the pachytene stage (FIG. 3A, FIG. 3B, FIG. 3C and FIG. 3D). In mutant leptotene spermatocytes the inventors detected focal staining with the COR1 antibody, which recognizes mouse SYCP3, a component of the lateral axes that eventually synapse to form the SC (Dobson et al., 1994). The inventors also found mutant zygotene spermatocytes (FIG. 3C and FIG. 3D) had well developed axes detected by the COR1 antibody, as well as regions of synapsis, detected by the SYN1 antibody which recognizes mouse SYCP1, a protein of the central element of the SC (Dobson et al., 1994). There were occasional late zygotene spermatocytes, but no pachytene spermatocytes with complete synapsis in −/− mice. Pachytene spermatocytes were, however, prevalent in the +/− mice. Thus spermatogenesis does not progress beyond early meiotic prophase, the leptottne and zygotene stages, in −/− mice.

Longitudinal studies comparing mutant versus wild-type testes indicated that −/− mice had histologically normal testes with normal numbers of prospermatogonia at postpartum day (dpp) 5. By dpp 10, −/− mice had produced significant numbers of spermatocytes, but even at this early time point, degeneration of spermatocytes was apparent. By dpp 18, cell death in spermatocytes of −/− mice was marked, and by dpp 24 no morphologically intact spermatocytes were seen (FIG. 11). By contrast, +/+ animals had produced numerous secondary spermatocytes and immature spermatids at dpp 24. Thus, the first wave of spermatogenesis in morc −/− mice is abortive, and −/− germ cells never progress through meiosis to form haploid spermatids.

5.1.3 Apoptosis in MORC−/− Testis

Since apoptosis is an important mechanism by which the testis regulates the number and quality of germ cells, the the manner of germ cell death in the mutant was studied. A modified fluorescent TUNEL assay (Mori et al., 1995) was performed on testis sections from 6 week old mice of all three genotypes. Briefly, biotinylated dCTP (Gibco-BRL, Grand Island, N.Y.) was incorporated using terminal deoxynucleotidyl transferase (TdT, Gibco-BRL), and detected by binding fluorescein isothiocyanate labeled streptavidin (Vector). Proteinase K digestion was 30 min at 37° C., and TdT incubation was 90 min at 37° C. Control tissues included small intestine and thymus.

Normal levels of apoptosis were found in +/+ (FIG. 4A) and +/− testes. However, there was extensive germ cell apoptosis in testes of −/− animals (FIG. 4B). Apoptotic cells coincided with the pyknotic cells seen by light microscopy in the adluminal compartment of the germinal epithelium in −/− mice, and the fluorescent TUNEL assay appeared to enhance the nuclear karyorrhexis typical of apoptosis (FIG. 4B). The increased apoptosis in −/− animals was seen as early as dpp 18. Thus, germ cells that fail to progress through meiosis I in −/− mice appear to be lost through apoptosis.

5.1.4 Tyrosinase Expression

Transgene expression was investigated to identify which cell types might be affected by the *microrchidia* mutation. Cells and tissues were lysed in buffer containing 2% CHAPS, 50 mM HEPES, 200 mM NaCl, pH 7.5, and protease inhibitors. Tyrosinase assays were performed as described (Halaban et al., 1983). One unit of tyrosinase was defined as the amount of enzyme that catalyzed the oxidation of 1 mmol of tyrosine in 1 min. Tyrosinase activity in testes extracts from 6 week old +/− mice was approximately 15% that of cultured mouse melanocytes, whereas no activity was detected in testis extracts of +/+ or −/− mice (FIG. 5). Western blot analysis confirmed the activity results.

Because the lack of tyrosinase activity in −/− mice may reflect expression of the transgene specifically in late primary/secondary spermatocytes, which are absent in these animals, tyrosinase immunohistochemistry was performed on fixed testis sections. Specific staining with PEP7 antiserum (Jimenez et al., 1991) was demonstrated in germinal epithelial cells of both +/− and −/− but not +/+ animals. Wild-type controls (+/+) showed no antibody staining. Intense staining is seen in the germ cell cytoplasm of +/− testes. Faint staining is also present in −/− germ cells. Staining of +/− testes was most prominent in post-mitotic germ cells. The fainter staining of −/− testes could represent tyrosinase levels below the sensitivity of the activity assay or western blotting. A survey of other tissues showed staining only in testis and retina. The abundant expression of tyrosinase in germ cells of histologically normal, fertile +/− males makes it unlikely that the microrchidia phenotype results from cytotoxicity due to ectopic tyrosinase activity.

5.1.5 Linkage of the Transgene to Microrchidia Phenotype

A PAC clone containing the morc transgene integration site was isolated and a 3.9-kb EcoRI fragment containing the insertion site was subcloned and sequenced. A phage library was constructed in vector EMBL3 from a complete BamHI restriction digest of −/− mouse DNA, size selected for 15–20 kb fragments. Screening the library with a polII-loxP chimeric probe yielded 5 clones, 4 of which had identical restriction patterns. A subclone of one of these 4 phage was sequenced to generate a sequence-tagged site (STS). This STS was used to screen a commercial mouse P1 artificial chromosome (PAC) genomic library (GenomeSystems, St. Louis, Mo.), and two clones were obtained. Subcloning of one of the PACs yielded a 3.9-kb EcoRI fragment containing the transgene insertion site.

Standard protocols were used for preparation of genomic DNA from tails or livers, extraction of total RNA from testes, and Southern and northern blotting (Sambrook et al., 1989). Genotyping was performed using STS's specific for either the wild-type locus or the rearranged transgenic locus. The transgenic STS produced a 200 bp PCR™ product using a pol II primer (5'-AGTTAGCCGTTATTAGTGGAGAGG-3'; SEQ ID NO:6) and a primer from morc −/− flanking genomic sequences (5'-AACTTGTAACTCAGGCTACAT-3'; SEQ ID NO:7). The wild-type STS primers (5'-GGTTGGCTTCAAATTCATGGT-3'; SEQ ID NO:8 and 5'-CATGGAGGTGTGAGCTAGGTG-3'; SEQ ID NO:9) were derived from sequences deleted in morc −/− mice and amplified a 93 bp product. PCR™ was performed using standard conditions and products analyzed on 3% agarose gels. The morc (microrchidia) locus name and symbol has been approved and reserved by the International Committee on Standardized Nomenclature for Mice (Maltais et al., 1997). The transgene described is designated TgN(Tyr)1Az and the allele of the morc locus identified by the insertion is designated $morc^{TGN(TYr)1Az}$ in accordance with the committee's rules.

BLAST searches (Altschul et al., 1997; Altschul et al., 1990) of Genbank with this sequence did not identify any known genes or expressed sequence tags (ESTs). Using the 3.9-kb sequence, a PCR™ assay was designed to genotype mice irrespective of eye color. The testicular masses of animals genotyped by this assay were then compared. The testis weights clearly fell into two groups normal and microrchidia phenotypes. None of 15 +/+ and 2 of 35 +/− mice had small testes, while 30 of 30 −/− animals had the morc phenotype of small testes. ANOVA comparing the weights from the three groups demonstrated that −/− mice had significantly smaller testes ($P<8.4\times10^{-36}$). There were no significant differences in mean body mass between the groups. The two +/− mice with small testes were littermates. These could be phenocopies due to an environmental insult or alternatively, morc may be semi-dominant with very low penetrance in heterozygotes.

5.1.6 The MORC Locus Contains a Deletion

A Southern blot probed with a fragment from one end of the 3.9-kb EcoRI subclone containing the transgene insertion site showed the expected wild-type 3.9-kb band in +/+ animals and a rearranged 2.8 kb band in +/− and −/− animals (FIG. 12A and FIG. 12B). DNA from +/+, +/− or −/− animals was digested with EcoRI and hybridized with each end of a 3.9-kb EcoRI fragment containing the transgene insertion site. One end detects an altered fragment (2.8 kb) for the morc chromosome. A probe from the other end of the subclone detected the same 3.9-kb EcoRI fragment in +/+ and +/− animals, but failed to detect any fragment in −/− DNA (FIG. 6B). The opposite end detects the 3.9-kb wild-type fragment with half intensity in +/− animals and no fragment in −/− mice, demonstrating a deletion to one side of the transgene. The inventors concluded that there was a deletion of genomic sequences to one side of the transgene. Failure to PCR™-amplify flanking sequences from DNA of −/− mice confirmed the deletion.

Additional bands were detected in Southern blots probed with a tyrosinase cDNA, suggesting that the transgene integrated into more than one chromosomal site. Further genotyping indicated that the additional transgenes became genetically fixed during the propagation of the morc line. However, these bands segregated independently from either the eye color or testis phenotype, demonstrating that the additional transgene(s) are silent with respect to tyrosinase expression and are unrelated to the morc −/− phenotype.

5.2 Example 2

Cloning, Sequencing and Characterization of the Human and Mouse Morc Genes

Using positional cloning, the a novel mouse gene, Morc, whose disruption by a transgene arrests spermatogenesis in early meiosis, was cloned and sequenced. Morc encodes a 108 kDa nuclear protein expressed specifically in male germ cells. The inventors also cloned the human MORC homolog was also cloned and shown to be testis-specific.

Mammalian spermatogenesis is a complex developmental process that can be divided into three phases: mitotic proliferation and renewal of diploid spermatogonia, meiotic divisions of spermatocytes, and cellular differentiation of haploid spermatids into mature sperm. Prophase of the first meiotic division is protracted: the pachytene stage alone lasts 9 days in mice (Handel, 1987). Attesting to the complexity of early meiotic events, a number of mutations have been found to disrupt the process at this stage. These include targeted inactivation of DNA mismatch repair enzyme Mlhl (Edelmann et al., 1996), the transcription factor A-myb (Toscani et al., 1997), and heat shock protein Hsp 70-2 (Dix et al., 1996).

The previous Example described a recessive mouse mutation, microrchidia (morc), whose phenotype is early meiotic arrest and apoptosis of male germ cells. Isolation of P1 genomic clones containing the Morc locus demonstrated that sequences adjacent to the transgene integration site were deleted in mutant mice. To better define the deletion and identify the coding sequence, a physical map of the region was constructed using one P1 clone (FIG. 6A). Then restriction fragments encompassing 21 kb of genomic sequence surrounding the transgene integration site were subcloned and sequenced. Southern blotting and PCR™ analyses revealed that the deletion spanned approximately 13 kb. Database searches with the sequence data did not identify any candidate genes.

Exon trapping was also performed using the entire P1 clone (FIG. 13). Nine different products were isolated and sequenced. Three were repetitive, and none of the other six single copy sequences showed similarity to any known genes or expressed sequence tags (ESTs) in public databases. However, Northern blot hybridization with one putative exon sequence detected a ~3 kb testis transcript. This 160 bp exon (FIG. 6A, exon 7) was used to screen a mouse testis cDNA library, and a single clone containing a ~900 bp insert was isolated. This clone also contained two other exon trapping products (FIG. 6A, exons 2 and 3).

A mouse multiple-tissue Northern blot probed with this cDNA demonstrated that the ~3kb transcript was unique to testis. Analysis of Morc expression in wild-type and mutant mice was performed. Exon trapping was performed with the vector pSPL3-iv (Nisson et al., 1994) according to the manufacturer's instructions (Gibco BRL) using libraries prepared from size-fractionated BamHI/Bg/II- or PstI-digested P1 DNA and one candidate exon used to isolate a partial mouse cDNA. 5' and 3' RACE using commercial mouse testis cDNA (Clontech Marathon) and Expand High Fidelity PCR™ System (Boehringer Mannheim) was performed with Morc-specific primers ATGGGGAGTACT-TGAAAATGATGGAC (SEQ ID NO:11) (5' RACE) or AGATGCCGGGGCTGTAAGACTCG (SEQ ID NO:12) (3' RACE). Products were cloned, and two independent clones were sequenced for each reaction. The mouse Morc cDNA was used to isolate a cDNA from a human testis library (Clontech) by plaque hybridization. The full-length human cDNA was isolated by 3' RACE using commercial human testis cDNA (Clontech) as described above with Morc-specific primer CTTCTTCGCCAGCGTCTTCTCA (SEQ ID NO:16). RACE products were cloned, and three independent clones were sequenced. Northern blot analysis of Morc expression using the mouse Morc cDNA 3' region probe was performed essentially as described (Cobb et al., 1997). RNA was extracted from enriched germ cells, testes of wild-type mice of various ages, or germ-cell deficient adult testes (at/at, XX,Sxr). β-actin hybridization controlled for loading in Northern blots.

The level of expression was very low compared to a β-actin control (a ten-fold shorter exposure of which is shown). Longer exposures revealed an additional ~2 kb testis transcript.

5' and 3' RACE was used to isolate a full-length Morc cDNA. Alignment of overlapping products gave a 3050 bp cDNA (SEQ ID NO:1), consistent with the ~3 kb transcript seen by Northern blotting. Construction of a physical map of the Morc locus and inspection of genomic sequence data indicated that the P1 clone contains at least the first seven exons but not the 3' end of the Morc gene. The complete gene may span >60 kb. Southern blotting and PCR™ analyses of DNA from morc −/− mice revealed that exons 2–4 (FIG. 6A) are deleted by the morc$^{TgN(TYr)1Az}$ transgenic insertional mutation.

To confirm that this mutation affected Morc expression, the inventors examined Morc transcripts in mutant mice by Northern blotting. Hybridization with a 158 bp cDNA fragment containing only Morc exons 2–4 (FIG. 6B) indicated that the wild-type transcript was absent in −/− testes (exon 2–4 probe). Interestingly, probing with a 1.2 kb fragment from the 3' region of the Morc cDNA (FIG. 6B) revealed a transcript in −/− testis that was similar in size to the wild-type Morc transcript (3' probe).

RT-PCR™ studies were performed to verify these Northern blotting results (FIG. 6B). A primer pair with one member from Morc exon 3 failed to amplify any −/− transcript. By contrast, a primer pair containing sequences 3' to the deleted exons 2–4 gave RT-PCR™ products with testis RNA from mice of all three genotypes. These data confirmed the absence of the wild-type Morc mRNA and the presence of an aberrant transcript in −/− testis. Additional RT-PCR™ studies indicated that the aberrant Morc transcript was not due to splicing of exon 1 to exons 3' of the deletion. The primer pairs were CGTGGGCGTGGGCCAA-CAGTT (SEQ ID NO:10; Morc exon 1) and ATGGGGAG-TACTTGAAAATGATGGAC (SEQ ID NO:11; Morc exon 7) or reverse primer shown in FIG. 6B, 5' primers; AGT-TAGCCGTTATTAGTGGAGAGG (SEQ ID NO:6; transgene RNA polymerase II promoter sequence) and Morc exon 7 primer. The latter primer pair gave several products from +/− testis RNA, the most abundant of which was sequenced. However, the inventors did find RT-PCR™ products containing transgene promoter sequences spliced to Morc exons 5–7. Interestingly, the total amount of Morc transcript appears to be increased in +/− testes, probably reflecting abundant transcription from the strong transgene promoter. The decreased level of the aberrant morc transcript in −/− testes can be explained by the paucity of germ cells, which specifically express the transgene, in these animals, as described above. Whether the aberrant morc transcript is translated remains to be determined.

In order to identify a human Morc homolog, the inventors screened a human testis cDNA library using the 900 bp mouse cDNA as a probe. A 2.8 kb cDNA was isolated and sequenced (SEQ ID NO:3). When used as a probe, this cDNA detected a ~4 kb transcript with expression again limited to testis. A full-length human cDNA was cloned by 3' RACE and sequenced. To confirm that the human cDNA was the mouse Morc homolog, the inventors mapped both mouse and human genes. Mouse Morc mapped to the central part of mouse Chromosome 16 (FIG. 14), while human MORC mapped to the conserved linkage region on 3q13 (FIG. 15). The nucleotide sequence, expression, and comparative mapping data all indicated that the human cDNA was the bona fide Morc homolog.

An alignment was performed of the mouse and human MORC proteins. The primary sequence of the mouse Morc cDNA predicts a protein of 950 amino acids, while the human cDNA encodes a protein of 984 amino acids that is 68% identical to mouse MORC. Two regions of human MORC, residues 669–692 and 955–971, encode insertions of 24 and 17 amino acids respectively relative to mouse MORC. RT-PCR™ studies showed no evidence that these insertions are due to alternative splicing. The similarity between the human and mouse MORC proteins was greatest in the amino-terminal half of the proteins, the region containing the exons deleted in morc$^{TgN(Tyr)1AZ}$ mice.

Database searches using standard BLAST and FASTA algorithms did not reveal similarity to any well-characterized proteins. There were, however, highly significant matches to a proline-rich protein encoded on human chromosome 22, a ubiquitously expressed gene from a human tumor cell line (KIAA0136) (Nagase et al., 1995), and genes from the nematode Caenorhabditis elegans (ZC155.3) and the plant *Arabidopsis thaliana*. Each of these proteins was 30–40% similar overall to mouse or human MORC, with local regions showing much greater similarity to portions of the amino terminal half of MORC.

Conserved motifs were identified by BLOCKMAKER (Smith et al., 1990; Lawrence et al., 1993; Henikoff and Henikoff, 1991) in mouse MORC (mMORC), human MORC (hMORC), human proline-rich protein (PRP), human protein from cell line KG-1 (KIAA0136), C. elegans predicted protein ZC155.3, zebrafish early gastrulation embryo cDNA, *Arabidopsis thaliana* predicted protein [Accession numbers for DNA and protein sequences in this paper are as follows: mouse Morc cDNA (AF084945), human MORC cDNA (AF084946), human proline-rich protein (AC004542), human cDNA KIAA0136 (Q14149), *C. elegans* ZC155.3 (U00064), zebrafish EST (AA605811), Arabidopsis ORF (AL022141), Dictyostelium ZipA (AF019980)].

Additional searching of EST databases indicated that the proline-rich protein is expressed in multiple somatic tissues. Interestingly, a mouse blastocyst EST was identified that is nearly identical to part of the Morc cDNA, suggesting that Morc is also expressed very early in development. The MORC protein also showed low but significant similarity to Dictyostelium discoideum ZipA, a leucine zipper protein that functions in morphogenesis (Loomis and Iranfar, GenBank Accession Number AF019980).

The inventors used a variety of computer algorithms to look for clues to the function of the mouse and human MORC proteins. The Paircoil program (Berger et al., 1995) strongly predicted coiled coil domains at residues 281–311, 320–350, and 885–917 in mouse MORC and at corresponding conserved human residues 280–354 and 900–935. A leucine zipper motif (Landschulz et al., 1988) with four heptad repeats at residues 926–947 overlaps the predicted coiled-coil domain of human MORC. The corresponding mouse sequence is quite similar but is interrupted by a proline at the position of the third leucine. Additional analysis using the PSORT II algorithm (Nakai and Kanehisa, 1992) predicted with high confidence that both human and mouse MORC are nuclear proteins, since both have a putative bipartite nuclear localization signal (residues 256–272 in mouse and residues 257–273 in human). Mouse MORC also has a second putative nuclear localization signal at residues 891–894. Of note, neither a transmembrane domain nor an N-terminal signal sequence was identified.

To test the predicted nuclear localization of MORC protein, the inventors expressed epitope-tagged mouse MORC in COS7 cells and determined its subcellular localization by multi-color immunofluorescence. MORC-expressing cells showed strong nuclear staining, usually in a discrete punctate pattern (FIG. 7A). Occasional cells showed more diffuse nuclear staining, and rare cells showed cytoplasmic staining. MORC proteins tagged with the FLAG epitope at either the N-terminus (FIG. 7A) or the C-terminus gave identical results. The inventors therefore conclude that the PSORT II prediction is accurate and that MORC is a predominantly nuclear protein.

To determine whether Morc is expressed in germ cells, the inventors analyzed fractionated germ cells from wild-type testes by Northern blotting. Morc transcripts were detected in all germ cell fractions except residual bodies, with the highest level in premeiotic spermatogonia and the lowest level in post-meiotic round spermatids. Interestingly, the ~2kb Morc transcript was seen only in pachytene spermatocytes. This expression pattern was confirmed by examining Morc expression in whole testes of increasing developmental age. Morc was expressed in testes from age 7 day through adult wild-type mice, as well as from newborns. The decrease in the level of Morc mRNA during testicular maturation likely reflects the changing ratio of spermatogonia to postmeoitic germ cells.

To test whether Morc is also expressed in testis somatic cells, the inventors examined mice that lacked germ cells due to either the recessive atrichosis (at) mutation (Hummel, 1966) or the sex-reversed XX,Sxr mutation (Cattanach et al., 1971). In neither case were Morc transcripts detected. The inventors also performed RNA in situ hybridization on wild-type mouse testis using a Morc antisense probe to independently confirm these results. The signal was localized to the germinal epithelium layers containing spermatogonia and spermatocytes, with only background over interstitial cells (FIG. 7B and FIG. 7C).

The inventors have defined the molecular basis of the mouse microrchidia mutation, which causes recessive male sterility with an arrest of spermatogenesis in early meiosis. The mutation is due to integration of a transgene into the Morc gene with concomitant deletion of Morc exons 2–4. The recessive phenotype and the morc deletion are consistent with a loss of function mutation. Expression analysis revealed that an aberrant morc transcript is present in mutant mice; however, its translation would result in a protein lacking at least the first 73 residues of MORC, an evolutionarily conserved region. This region is therefore likely critical to MORC's function.

Of note, the inventors found no other genes expressed in testis within the P1 clone containing the transgene integration site, either by exon trapping or by nucleotide sequencing of ~21 kb of flanking sequence, and the transgene and deletion are wholly contained within the Morc transcription unit. Moreover, the microrchidia mutation affects only spermatogenesis, consistent with Morc's exclusive expression in male germ cells. Finally, genetic cosegregation between the transgene insertion/deletion and the Morc phenotype (Watson et al., 1998) provides additional support for the morc mutation as the causal factor for male germ cell arrest.

The Morc transcript is rare: prolonged exposures are necessary to detect Morc by Northern blotting, and only one EST corresponding to Morc is represented in public databases. Although the human and mouse Morc genes are expressed specifically in male germ cells, two related human genes (KIAA0136 and the proline-rich protein) are expressed in multiple tissues. These data suggest that MORC plays a specialized role in germ cells that is related to a more general function of other family members in somatic cells. The presence of related genes in organisms as divergent as humans, nematodes, plants, and slime mold also predicts a critical role for Morc family members in eukaryotic cellular biology.

Morc encodes a nuclear protein. Based on the similar phenotypes of the morc-mutation and several mouse knockouts (Okabe et al., 1998), the inventors suggest that MORC may function in transcriptional or translational regulation, cell cycle control, DNA repair, or meiotic chromosome dynamics. The MORC proteins are predicted to have conserved coiled-coil domains, suggesting that they may form multimers with other proteins. The punctate nuclear localization of transfected MORC indicates that the native protein in germ cells may be part of a large protein complex, such as the DNA 'repairosome' (He and Ingles, 1997). On the other hand, the low abundance of Morc mRNA suggests that MORC may be a regulatory protein. Interestingly, Morc is transcribed in both mitotic and meiotic germ cells, although testes lacking MORC show no histologic defects until meiosis begins (Watson et al., 1998). Perhaps MORC is required for initial assembly of a nuclear complex in spermatogonia to be used later in meiosis. Whether MORC interacts with other proteins that are also required for germ cell development, such as the DAZ/DAZLA putative RNA binding proteins (Ruggiu et al., 1997; Reijo et al., 1995), remains to be studied. Further studies are also needed to determine the precise cellular and subcellular localization of MORC protein in testis.

Thus far the microrchidia mutation has been found to affect only spermatogenesis. Since MORC acts specifically in testis, selective inhibition of human MORC or its biochemical pathway may not have systemic side effects. Thus, the MORC gene product may provide an attractive new target for development of male-specific contraceptives. Conversely, agents that increase MORC activity may palliate certain forms of male infertility.

5.3 Example 3

Polynucleotide Sequence of Murine Morc (SEQ ID NO:1)

```
GCAAGTGAGCCAGGCCGTACGCGTGGACGTAGGCGTGGGCGTGGGCCAACA
GTTTCCGGTCAGACATCCACGTCTTCTGTTGTCCGCAGGTGGTGCCTGAAGACAT
GGACAAATATGCCTTGCTGCAGAGGGCTAAACTGCATCTGGATTTCATCCACGCG
AATTCCACAACACACAGTTTCCTCTTTGGAGCACTGGCTGAGTTGCTGGACAACG
CAAGAGATGCCGGGGCTGTAAGACTCGATGTGTTTTCAGTGGATAATGAAACACT
GCAGGGAGGATTCATGTTGTGTTTCCTGGATGATGGATGTGGCATGAGCCCTGAT
GAAGCTTCAGACGTAATTTACTTTGGAACATCCAAGAAACGCTTGTCGACCTTGA
AGTTCATCGGGCAATATGGTAACGGGCTTAAGAGCGGCTCCATGAGAATCGGCAA
AGACTGTATTCTTTTCACAAAGAAGGAAGAGACCATGACCTGTCTGTTCTTCTCT
CAGACTTTCTGTGAAAAGAAGGTCTCACTGAGGTTGTAGTTCCAATACCTTCAT
GGCTAACGAGAACCAGAGAGAGTATCACAGATGACCCGCAGAAGTTCTTCACAGA
ATTGTCCATCATTTTCAAGTACTCCCCATTTAAGACCGAAGCTGAATTGATGCAG
CAGTTTGATATGATCTACGGGAGATGTGGAACTTTGCTGATTATTTATAACTTGA
AGCTGCTGCTTAGCGGAGAACCAGAGTTGGATGTTACAACCGACAAAGAAGATAT
ACTGATGGCCGAGGCTCCGGAGGAAATTCCAGAGAGACGGTCATTCAGAGCCTAC
ACAGCTGTTCTGTATTTTGAACCCCGGATGAAAATATTTATTCAGGCCAAAAGAG
TTCAAACAAAGCATCTGTGTTATTCCCTCTACAAACCCAGAAAATACCAATATAC
TACATCTTCTTTCAAAGGGAAGTTTAAAACTGAAGTTCAAAAGGCAGAAGAAGCA
GTAAAGAGGGCTGAACTCCTGTTTAAAGAGGTGCAAGCCAAAGTAAACCAGCCGG
ACAGAATTGCTTTGTCTTCTACCCAGGATGCATTACAGAAAGCTCTGCAAGACGT
GGACACAAAGCATAAAAGTCTTCGCCAGAAACAGAGGGCCCTAAGGAAAGCAAGA
ACTCTCTCTCTGTTCTTTGGAGTGAACACAGAAGACCAACACCAAGCTGGAATGT
TCATTTACAGTAATAACCGATTGATCAAAATGTACGAGAAGGTTGGTCCCCAGCT
GAAAATGAAGTCATTACTTGGTGCAGGTATAATTGGAATTGTGAACATACCTTTG
GAGACCATGGAACCATCCCATAATAAACAAGAATTCCTCAATGTCCAAGAATACA
ATCATCTACTAAAAGTCATGGGACAGTACTTGATCCAGTACTGTAAGGACATTGG
GATCAGTAATAGAAACCTAACACTGTTTTGGGACGAATTTAAATATCAGCATAGC
AAAGACACAGACAGCTCTTTGGAATCTCTCCAATGGCGAAGAAGACAAGCCATGG
GTATCCCATTCATCCTACAATGCGATCTTTGTCTCAAATGGAGAGTCCTGCCTTC
CTCTTCCAATTACCAGGAAAAAGGATTACCTGACCTATGGATTTGTGCCAGTAAT
```

-continued

```
CCCAACAACCTGGAAAACAGCTGTAACCAGATAGAGCGCCTGCCTTCTATCCCAC

TGGGCACCGTGAACAGAAGACCACCATCAAAAGATGAGAGAGAGAGGCAACTTCA

AGAGTCAGTCCAGAGATATCAGGACAAGCTGGTGGAAGCGCAGCCGCAGAAGTCT

CAACTTATAGTAACAAGCAAGATCCCCGAGTTCAAGTCCTCCTGCCTTTCCTCAG

CACTCAAGGAAAAATCCAAACTTGGGAGAATCCAGCCTTCAGGGGCAGACCTGAC

TCAGGGCAGTCCCTCATCTGTTAAGCTTTCGTTCATGCAAAGAAGCCAAAAGAGG

AGCACAGAGGATACTCACTCGGACGTGGAGTTCATCTGCATGACGAAGATTCCGA

AGAAGTCTGTGAAGAAGACCGTGAAGTACCTGCAGCCTGGTCACGCTCCAGCTCT

ATTGGAAAACCTCAAACTCGAGGACACAGCCCAGGTTTCTTCACGGGAAATAAAA

AAGCAGCAGAGTGAGAGCCTCGTGCAGGCAGGCAAGGCATCCACTGACGTGGCTA

GCAGCAGAGATCCAACTGTGACCATGGTTTGGGATCAAAGCAGCACCAAGGTCTC

ACTGAAACAAGAAGAAGAGGAGGAAGTTCCCCTCATAAAGCCAGACAAACAAGAG

CTGTGTGATGATACTCCAGTAGTGAAAGGAAATTCTTCAGCGCTTCACTGGAAAA

GCTTGCCCGGGGTGCAAATGGAAGATTTAAGTCCACGTTCTGGACACAAAATCAA

CTCTGTGAGTGGTGACTGTCAGCTGCCGGCTTCACCAATGCCTTCTCAAAGCATG

TCTGTGGAAGAAACAGCAAGAAAACTGCTGTCTAACTTAAGGGAAATTCTTCTAT

ACTTTGTTCCCGAGTTTCAGCTATCATCAGAATTTGAGTGCACATCTGTGGAAGA

ACTCATAACAAATCCTGAGCTGGAGCGATGCCCAGAGAATATAAACGAAAAGCTA

AAAACGTGTTTCAACCAGATCCAGAATATCTACATGGCTCAGTATGAGAAAAGAC

TCAAGAGGAAAATGCAGTCCATTGTCTATGAGGCAAACAGAAGGGGCTTACTCAA

CCAAGTGTTTCTGGGACAGTGTGAACTGAAAAGGAAGAGGACTGAGGAGAAACTC

AGTGACCTTCGTGCAAAGCTGGCCTTGCTGCTGCAGAAACTTCAGCTGGGTGGTC

CAGCAGGAGACCCGCAGCAGATTGATGCTTACTTAGAAGATTTGCTTAAAGAAGA

TCGGCTCCCGACCGCTTTACATGAAAAGTCTCCAGAGTCAGCGTAAGCAAAAGAT

ACAGAACCCTGAGAGGGTATCTCAGAAGTCAGAAAAGATGTTTTTTCTTAAAACC

ACTAATAAAGAAAACTGGAAAATCCTTTTA
```

5.4 Example 4

Polypeptide Sequence of Murine Morc (SEQ ID NO:2)

```
MDKYALLQRAKLHLDFIHANSTTHSFLFGALAELLDNARDAGAVRLDVFSV

DNETLQGGFMLCFLDDGCGMSPDEASDVIYFGTSKKRLSTLKFIGQYGNGLKSGS

MRIGKDCILFTKKEETMTCLFFSQTFCEKEGLTEVVVPIPSWLTRTRESITDDPQ

KFFTELSIIFKYSPFKTEAELMQQFDMIYGRCGTLLIIYNLKLLLSGEPELDVTT

DKEDILMAEAPEEIPERRSFRAYTAVLYFEPRMKIFIQAKRVQTKHLCYSLYKPR

KYQYTTSSFKGKFKTEVQKAEEAVKRAELLFKEVQAKVNQPDRIALSSTQDALQK

ALQDVDTKHKSLRQKQRALRKARTLSLFFGVNTEDQHQAGMFIYSNNRLIKMYEK

VGPQLKMKSLLGAGIIGIVNIPLETMEPSHNKQEFLNVQEYNHLLKVMGQYLIQY

CKDIGISNRNLTLFWDEFKYQHSKDTDSSLESLQWRRRQAMGIPFILQCDLCLKW

RVLPSSSNYQEKGLPDLWICASNPNNLENSCNQIERLPSIPLGTVNRRPPSKDER
```

-continued

ERQLQESVQRYQDKLVEAQPQKSQLIVTSKIPEFKSSCLSSALKEKSKLGRIQPS

GADLTQGSPSSVKLSFMQRSQKRSTEDTHSDVEFICMTKIPKKSVKKTVKYLQPG

HAPALLENLKLEDTAQVSSREIKKQQSESLVQAGKASTDVASSRDPTVTMVWDQS

STKVSLKQEEEEEVPLIKPDKQELCDDTPVVKGNSSALHWKSLPGVQMEDLSPRS

GHKINSVSGDCQLPASPMPSQSMSVEETARKLLSNLREILLYFVPEFQLSSEFEC

TSVEELITNPELERCPENINEKLKTCFNQIQNIYMAQYEKRLKRKMQSIVYEANR

RGLLNQVFLGQCELKRKRTEEKLSDLRAKLALLLQKLQLGGPAGDPQQIDAYLED

LLKEDRLPTALHEKSPESA

5.5 Example 5

Polynucleotide Sequence of Human Morc (SEQ ID NO:3)

GGCGAACGGCTGCCGGTCAGGTGTCCTTGTCCCCTTGAGTTGCGCGGGTCG

TGTTCGAGGGCATGGACGACAGGTACCCTGCGCTTCAGCGGGCCCAGCTGCGTCT

GGATTTCATCCACGCCAACTCCACCACTCACAGTTTCCTTTTTGGAGCACTGGCT

GAATTGCTGGACAATGCAAGAGATGCAGGGGCTGAAAGACTTGATGTCTTTTCAG

TGGATAATGAAAAACTGCAGGGGGATTCATGTTGTGTTTCCTGGATGATGGATG

TGGCATGAGCCCTGAGGAAGCTTCAGACATCATTTACTTTGGACGATCCAAAAAA

CGGCTGTCAACCTTGAAGTTCATAGGGCAATACGGCAATGGTCTTAAAAGTGGGT

CCATGAGAATTGGAAAAGACTTTATTCTTTTTACGAAGAAGGAAGAAACGATGAC

CTGTGTGTTTTTTTCTCAGACATTCTGTGAAGAAGAAAGTCTTAGTGAGGTTGTA

GTTCCAATGCCCTCATGGTTAATAAGAACCAGAGAATCTGTCACAGATGATCCCC

AGAAATTTGCAATGGAATTATCTATAATTTATAAATACTCCCCATTTAAAACTGA

AGCAGAATTGATGCAGCAGTTTGATGTGATCTATGGAAAATGTGGTACTTTGCTG

GTTATTTATAACTTGAAGCTTCTGCTTAATGGAGAACCAGAGTTGGATGTTAAAA

CTGACAAAGAAGATATACTGATGGCTGGAGCTCTGGAGGATTTCCCAGCGAGGTG

GTCATTCAGAGCCTACACATCTGTTCTGTATTTTAACCCATGGATGAGAATATTC

ATTCAAGCCAAGAGAGTTAAAACTAAACATCTTTGCTATTGCCTCTACAGACCCA

GAAAGTATCTTTATGTCACATCTTCTTTTAAAGGAGCATTTAAAGATGAAGTTAA

AAAGGCAGAAGAAGCAGTAAAGATTGCTGAATCCATATTGAAAGAAGCACAAATC

AAAGTAAACCAGTGTGACAGAACCTCTTTATCTTCTGCCAAGGATGTATTACAGA

GAGCTTTGGAAGATGTAGAAGCAAAGCAAAAGAATCTTAAAGAGAAACAAAGAGA

ATTAAAAACAGCAAGAACGCTCTCCCTGTTCTATGGAGTGAACGTAGAAAACCGA

AGCCAAGCTGGAATGTTCATTTACAGTAATAACCGTTTGATCAAAATGCATGAAA

AAGTGGGCTCACAGTTGAAACTGAAGTCCTTACTTGGCGCAGGCGTGGTTGGAAT

TGTTAATATACCCTTGGAGGTCATGGAACCATCCCATAATAAACAGGAATTTCTC

AATGTCCAAGAGTATAATCATCTACTAAAAGTCATGGGACAGTACTTGGTCCAGT

ACTGTAAGGACACCGGCATCAATAATAGAAATTTAACATTGTTTTGCAATGAATT

TGGATACCAGAATGACATCGACGTGGAGAAACCTTTAAATTCTATTCAATATCAA

-continued

```
AGAAGACAAGCCATGGGTATCCCATTCATCATACAATGTGATCTTTGTCTTAAAT
GGAGAGTCTTGCCTTCCTCTACTAATTATCAGGAAAAAGAATTTTTTGACATTTG
GATTTGTGCTAATAATCCCAACCGCTTGGAAAACAGTTGTCATCAGGTAGAATGT
CTACCTTCCATCCCACTGGGCACCATGAGCACAATATCACCATCAAAAAATGAGA
AAGAGAAGCAACTTAGAGAGTCGGTCATAAAGTATCAAAATAGACTGGCAGAACA
GCAGCCACAGCCTCAATTTATACCAGTGGACGAAATCACTGTCACTTCCACCTGC
CTAACTTCAGCACATAAGGAAAATACCAAAACCCAGAAAATCAGGCTTTTGGGCG
ATGACTTGAAGCATGAATCTCTTTCATCCTTTGAGCTTTCAGCGAGCCGTAGAGG
ACAGAAAAGAAACATAGAAGAGACAGACTCTGATGTAGAGTATATTTCAGAAACA
AAAATTATGAAAAGTCTATGGAGGAGAAAATGAACTCTCAACAGCAGAGAATTC
CAGTAGCTCTGCCAGAAAATGTCAAACTAGCTGAGAGATCCCAGAGAAGTCAGAT
TGCTAATATTACCACTGTCTGGAGAGCTCAACCAACTGAAGGGTGCCTGAAGAAT
GCCCAGGCCGCTTCTTGGGAAATGAAAAGGAAGCAGAGTCTCAACTTTGTAGAGG
AATGTAAGGTATTGACTGAAGATGAGAACACGAGTGATTCAGATATAATCCTGGT
TTCAGATAAAAGCAACACTGATGTTTCATTGAAACAAGAAAAAAGGAAATTCCT
CTTTTAAACCAAGAAAAACAGGAGCTGTGCAATGATGTTCTAGCAATGAAAAGAA
GCTCTTCATTACCTAGCTGGAAAAGCTTGCTCAATGTGCCGATGGAAGATGTGAA
TCTAAGTTCTGGACACATAGCCAGAGTTTCTGTGAGTGGCAGTTGTAAAGTTGCT
TCTTCGCCAGCGTCTTCTCAAAGCACACCTGTCAAGGAAACAGTGAGAAAACTGA
AGTCTAAGTTAAGGGAGATTCTTCTGTATTTTTTTCCTGAGTATCAGCTACCATC
AGAATTGGAAGAACCTGCATTAAGTTGTGAGCTGGAGCAGTGCCCAGAGCAGATG
AACAAAAAGCTGAAAATGTGTTTCAACCAGATACAGAATACTTACATGGTCCAAT
ATGAAAAAAAATAAAGAGGAAATTGCAGTCCATTATCTATGATTCAAATACAAG
AGGAATACATAATGAAATCTCTCTGGGGCAATGTGAAAATAAAAGAAAAATCTCT
GAGGATAAGCTGAAGAATCTTCGTATAAAACTGGCACTATTGTTGCAGAAACTCC
AACTGGGTGGTCCAGAAGGTGACCTGGAGCAGACTGACACTTATTTAGAAGCTTT
GCTTAAAGAAGATAATCTTCTCTTCCAGAACAATTTAAATAAAGTAACTATAGAT
GCAAGACATAGACTCCCTTTAGAAAAAAATGAAAAGACTTCGGAAAATTAAGTCA
GAGATGGTATTACCTTTTAAAAAATGCTAATAAGAAAATTGGAAGATTCTTTTAA
AAATTTTTCTTTTTTGTTGTTGTTACTGTAAAGTCTATTCTGTTTAACAATAAGA
AATAAGAAATAATTTTTTTCAAATAAGAAAATTGTGTACTCTAGAAATGGAGACC
GATTTACAATTTATGTATTCCCTAATCCAATTATCTAAATCTTCCTTTTCTTTCA
GAAATATTAATAATATCTAGAGTTCTCTAATTTTCATGTGAGCTACTGAAAAAAA
TGAAAATGTCACTCAAGCTTAACTTTTGTTATTCCTTAAAAGATTGTTATTGTAA
TTTTGTTATTCCTTAAAAACATTTAAAAGCAGATTTTTTCAAATCGATATGTGA
AGGACTACAGAATCACCTCCTCTTGAAGATATTGAAAAGAAAGACATTATGCCC
TTTCTCCACTATAGCCAACACTCAGTCAAGCAGAAAATACAAATCCCCCCAAAAC
TTTGAGACATAGCTTATATAATTTTATTATTTAGTCATAGTAAAAGAATAAATCT
CCTAAGCATAATATGTATACATATTACACATATGTAAAAATTGTTGTTTTACATT
```

-continued

```
TACATATACGTAAAGAAGTATGTTTTTACACTTTTCTTGATAAGTGTTTTTTTT

GTTTAGAAATGTCTGAAACTTTAGACAAAAACAATAAAACATTTAATATTCATTT

GAT
```

5.6 Example 6

Polypeptide Sequence of Human Morc (SEQ ID NO:4)

```
MDDRYPALQRAQLRLDFIHANSTTHSFLFGALAELLDNARDAGAERLDVFS

VDNEKLQGGFMLCFLDDGCGMSPEEASDIIYFGRSKKRLSTLKFIGQYGNGLKSG

SMRIGKDFILFTKKEETMTCVFFSQTFCEEESLSEVVVPMPSWLIRTRESVTDDP

QKFAMELSIIYKYSPFKTEAELMQQFDVIYGKCGTLLVIYNLKLLLNGEPELDVK

TDKEDILMAGALEDFPARWSFRAYTSVLYFNPWMRIFIQAKRVKTKHLCYCLYRP

RKYLYVTSSFKGAFKDEVKKAEEAVKIAESILKEAQIKVNQCDRTSLSSAKDVLQ

RALEDVEAKQKNLKEKQRELKTARTLSLFYGVNVENRSQAGMFIYSNNRLIKMHE

KVGSQLKLKSLLGAGVVGIVNIPLEVMEPSHNKQEFLNVQEYNHLLKVMGQYLVQ

YCKDTGINNRNLTLFCNEFGYQNDIDVEKPLNSIQYQRRQAMGIPFIIQCDLCLK

WRVLPSSTNYQEKEFFDIWICANNPNRLENSCHQVECLPSIPLGTMSTISPSKNE

KEKQLRESVIKYQNRLAEQQPQPQFIPVDEITVTSTCLTSAHKENTKTQKIRLLG

DDLKHESLSSFELSASRRGQKRNIEETDSDVEYISETKIMKKSMEEKMNSQQQRI

PVALPENVKLAERSQRSQIANITTVWRAQPTEGCLKNAQAASWEMKRKQSLNFVE

ECKVLTEDENTSDSDIILVSDKSNTDVSLKQEKKEIPLLNQEKQELCNDVLAMKR

SSSLPSWKSLLNVPMEDVNLSSGHIARVSVSGSCKVASSPASSQSTPVKETVRKL

KSKLREILLYFFPEYQLPSELEEPALSCELEQCPEQMNKKLKMCFNQIQNTYMVQ

YEKKIKRKLQSIIYDSNTRGIHNEISLGQCENKRKISEDKLKNLRIKLALLLQKL

QLGGPEGDLEQTDTYLEALLKEDNLLFQNNLNKVTIDARHRLPLEKNEKTSEN
```

5.7 Example 7

Complementation of the Microrchidia Phenotype in Mice Expressing Ubiquitous and Testes Specific Transgenes The example describes the construction of two types of transgenes that may be prepared using the Morc wild type cDNA. First, a minigene construct that uses the Zfy testes-specific promoter is joined to the Morc cDNA together with Morc 3' untranslated region and polyadenylation signal. The Zfy promoter has been well characterized and is expressed throughout germ cell development (Zambrowicz et al., 1994). The second construct employs the ubiquitous beta-actin promoter to drive Morc expression (Niwa et al., 1991).

Five or more transgenic founder lines are established by microinjections of male pronuclei from wild-type C57BL6/NCr type mice. These founder animals are maintained until expression analyses and crosses to microrchidia mutant mice have been completed. Founders may be genotyped by PCR™ and Southern blotting of tail DNA to detect incorporation of the transgene. Expression of the transgene in positive animals is surveyed by RT-PCRT™ and northern blotting of tissues including testes. Of course, mice may be carefully monitored for unforeseen effects of ectopic transgene expression, which may provide additional clues to Morc's function. Western blot analysis provides parallel confirmation of protein expression in tissues expressing Morc mRNA.

Transgenic lines expressing Morc in testis may be crossed with microrchidia +/− mice. F1 progeny that are both transgene positive and microrchidia +/− may then be back-crossed to +/− mice. The backcross progeny of interest may be those males that are microrchidia −/− and transgene positive. The expected result is that the transgene may at least partially alleviate the block in spermatogenesis, to be determined by testis histology and test breeding with wild type females. Once a successful transgenic rescue has been accomplished, one may create subsequent transgenic lines containing various Morc point mutation or deletion mutants in order to perform structure/function analysis.

5.8 Example 8

Characterization of Meiotic Arrest in Morc −/− MICE

Since the microrchidia −/− phenotype is characterized by the absence of post-meiotic spermatocytes, it is possible that cells normally fated to enter meiosis instead undergo apoptosis. Apoptosis is a normal feature of mammalian germ cell development (Allan et al., 1992; Johnson et al., 1984; Johnson et al., 1987; Roosen-Runge; 1955; Roosen-Runge, 1973; Blanco-Rodriguez and Martinez-Garcia, 1996; Brinkworth et al., 1995; Russell and Clermont, 1977; Oakberg, 1956; Clermont, 1962) and is a response of germ cells and germ cell tumors to diverse agents such as chemotherapy and radiation (Chresta et al., 1996; Riou et al., 1995; Cai et al., 1997; Hasegawa et al., 1997; Ito et al., 1997; Shikone et al., 1994; Troiano et al., 1994). The inventors propose that the absence of the Morc protein in early stages of germ cell development triggers apoptosis via the pathway normally present in these cells.

To test the hypothesis that the absence of MORC protein triggers the endogenous apoptotic cascade in germ cells, one may examine apoptosis in microrchidia −/− testes. Paraffin sections from all three genotypes of adult (40–60 day old) mice may be stained using the TUNEL apoptosis assay. A commercial kit may be used (Boehringer Mannheim Biochemicals, Indianapolis, Ind.). As a second independent method to detect apoptosis, one may use a commercial annexin V assay (Clontech) which detects translocation of phosphotidyl serine across the plasma membrane of apoptosing cells.

If increased levels of apoptosis are found in adult −/− testes, one may examine the temporal pattern of apoptotic activity. Sections from neonatal through juvenile testes may be tested using both assays. Preliminary time points may be 5, 10, 18, and 24 days in order to span germ cell developmental milestones, including entry into meiosis (day 10), appearance of secondary spermatocytes (day 18) through appearance of mature sperm in the lumen of the seminiferous tubule (5–6 wk). Depending on the results, additional time points may be examined to define more precisely the onset of programmed cell death during development.

The histologic appearance of testes in −/− adults is consistent with an arrest in spermatogenesis at or before the transition from primary to secondary spermatocytes (i.e. meiosis). However, the cells that appear to be primary spermatocytes are morphologically abnormally, e.g., condensed. One may test expression of a set of molecular markers for different stages of germ cell differentiation in order to more precisely determine the point at which spermatogenesis arrests in −/− mutants. Unfortunately, antibodies to stage-specific antigens expressed during spermatogenesis are not generally available. However, the temporal pattern of expression of a number of marker genes has been determined at the RNA level. Although the expression profile of most of these markers extends over more than one cell type, multiple markers can be used to define the stage at which spermatogenesis arrests. Similar marker studies were successfully used to characterize the A-myb knockout mouse, in which spermatogenesis arrests at the pachytene primary spermatocyte stage (Toscani et al., 1997).

To perform these studies, one may make northern blots of mRNA from testes of +/+, +/−, and −/− adult mice. These northerns may be hybridized with probes representative of sequential stages of germ cell development. Markers may be Pgk-2 (phosphoglucokinase-2), Hsp70-2 (heat shock 70-2), Krox-20, c-fos, proacrosin binding protein, protamine-1, Ctk, and CREM. A beta actin control probe may be used to control for differences in loading of samples. The probes for the marker genes may be obtained from the American Type Culture Collection or from RT-PCR™ using published sequences.

5.9 Example 9

Cellular and Biochemical Characterization of Morc

The results of transgene expression studies suggest that the Morc gene is expressed specifically in germ cells. However, expression of the tyrosinase transgene might not be the same as the Morc gene, since the transgene carries its own promoter and may also be subject to position effects. It is thus important to determine which testis cells express Morc. If the protein acts cell-autonomously, then it must be present in germ cells, like Dazl (Ruggiu et al., 1997; Seboun et al., 1997; Cooke etal., 1996). Conversely, if Morc is present in the interstitial or Sertoli cells, then it probably acts non-cell-autonomously to regulate spermatogenesis via cell-cell signaling, like desert hedgehog (Bitgood et al., 1996; Hammerschmidt et al., 1997).

One may measure Morc mRNA in mutant mice that lack germ cells. If Morc RNA is present, then it must be expressed in somatic cells. If it is absent, then it likely to be expressed in the germline. This approach has been previously used to characterize the expression pattern of other genes that are thought to be important in spermatogenesis, including Zfyl (Koopman et al., 1989), desert hedgehog (Bitgood et al., 1996) and Dazl (Reijo et al. 1996).

The c-kit (W) mutation, which blocks the migration of primordial germ cells during embryogenesis (Mintz, 1957) may be utilized. This mutation causes dominant spotting. The homozygous null mutation (W) is an early embryonic lethal, but a viable mutation (W$^v$) is also available. Wild-type (+/+), W/+, W$^v$/+, and W/W$^v$ mice can all be readily distinguished by coat color and spotting pattern. Testes of W/W$^v$ mice contain normal somatic cells (Sertoli and interstitial cells) but no germ cells (Mintz and Russell, 1957).

W/+ and W$^v$/+ heterozygotes may be obtained from the Jackson Laboratories and crossed to obtain F1 progeny of various genotypes, distinguishable by coat color. The strains are C57BL/6J (W$^v$) and WB/ReJ (W). Approximately half of the F1 progeny may be male, and the four possible W genotypes may be present in roughly equal proportions. Thus the W/W$^v$ males may comprise 1/8 of the total F1 progeny. One may dissect the testes from the W/W$^v$ males and wild-type or heterozygous littermates, purify mRNA, and assay for Morc expression by northern blotting and RT-PCR™. Samples from W/W$^v$ mice and normal littermates may be compared to determine whether Morc expression is limited to the germ cell compartment of testes.

One may first raise antipeptide sera to predicted immunogenic regions of the Morc protein. One may first make peptides from the N- and C-termini of the predicted Morc protein, as these termini are reasonable hydrophilic and are frequently exposed in native proteins. The peptides may have a Gly-Gly-Cys spacer-linker for conjugation to carrier proteins and for convenient matrix coupling if affinity purification is necessary. The sequences are DKYALLQRAK-LHLDFIHAGGC (SEQ ID NO:17; amino terminus) and CGGKEDRLPTALHEKSPESA (SEQ ID NO:18; carboxyl terminus). These may be conjugated to MDDS-activated keyhole limpet hemocyanin (Pierce, Rockford, Ill.). KLH-coupled peptides may be purified by column chromatography, emulsified with Freund's adjuvant, and injected subcutaneously into New Zealand White rabbits (two rabbits per peptide). Animals may be boosted after 3 wk and test bleeds performed 14 days later. Serum antibody titers may be measured by an ELISA assay using plates coated with peptide and sera with titers >1:1000 may be utilized. Additional antigen boosts may be performed if necessary. Terminal. exanguination may provide up to 100 ml of polyclonal antiserum for westerns, immunohistochemistry, immunoprecipitations and future studies.

Once generated, high titer polyclonal antisera may be used to determine the localization of Morc in mouse tissues.

Based on the northern results (FIG. 8) it is not expected that Morc protein will be expressed in tissues other than male germ cells (FIG. 8).

5.10 Example 10

Bacterial Expression and Subcellular Localization of Morc Protein

As a second approach, one may immunize rabbits with recombinant Morc protein. The use of native protein as an immunogen may complement antipeptide antibodies in that different epitopes may likely be recognized by the different reagents.

One may express and purify Morc protein in bacteria. To produce protein in bacteria, one may use the pET expression plasmid system (Novagen, Madison, Wis.). This system uses a T7 promoter to drive expression from cloned genes on the pET plasmid using an *E. coli* strain {BL21(D3)} that expresses the T7 RNA polymerase under the control of the inducible lacI promoter, allowing for large amounts of inducible protein expression (Leahy et al., 1992). Induction conditions and temperatures may be varied to optimize the yield of soluble protein.

Morc may be expressed with both N and C terminus His-tags using vectors pET16b and pET 29a respectively. Both constructs may be tested in protein minipreps to define the optimal purification conditions. Large scale cultures may then be employed to produce milligram quantities of protein, which may then be purified in a single step by nickel agarose affinity chromatography.

The subcellular localization of Morc may direct subsequent biologic hypotheses regarding its function. For example, if Morc acts as a cell surface receptor, it obviously may be associated with the plasma membrane. It is also possible that Morc shuttles between the nucleus and cytoplasm, like the DAZ gene. If Morc regulates apoptosis, it might be nuclear, cytoplasmic, or associated with mitochondria like Bcl2 (Nguyen et al., 1993; Hockenbery et al., 1993).

One may express an epitope-tagged Morc protein in tissue culture cells and use commercial antibodies to determine its subcellular localization. The eight amino acid FLAG tag has been added to the ends of many proteins without disrupting their localizations or functions (Collins and Uhler, 1997; Simonian et al., 1997; Ziv et al., 1997; Wu and Chiang, 1996; Oster-Granite et al., 1996; Chubet and Brizzard, 1996; Mariani et al., 1996; Stewart et al., 1996; Dent et al., 1995). One may express the full length wild type mouse morc cDNA with the FLAG tag at the N- or C-terminus, using the pMEPy vector containing an SV40 enhancer and chimeric promoter with an SV40 polyadenylation signal. Mammalian cell lines, initially COS7 cells, may then be cotransfected with the expression plasmids, together with a plasmid encoding beta-galactosidase to monitor transfection efficiency. Subcellular localization of the tagged Morc protein may then be performed using commercial anti-FLAG peptide antibodies that are excellent reagents for these studies. Secondary antibodies labeled with fluorescein isothiocyanate be used for fluorescent detection of antibodies. Positive and negative controls may include the PIG-A construct and vector alone. Other cell lines that do not amplify the vector (CHO and HeLa) may also be transfected to ensure reproducibility.

5.11 Example 11

Two Hybrid Analysis

To gain an understanding of Morc's biologic function, it is important to identify interacting proteins. Given the lack of a facile germ cell culture system, one may use the well characterized yeast GAL4 two hybrid system to identify interacting proteins (Bartel and Fields, 1997). This system can detect protein-protein interactions between a "bait" molecule (i.e. Morc) and an interacting "prey" that allow transcription from a reporter gene (e.g., lacZ) and a yeast selectable marker (e.g., HIS3). One may use a commercial yeast two-hybrid product, Clontech's "Matchmaker Two-Hybrid System," together with their mouse testis MATCH-MAKER cDNA library. This system has the advantage of allowing false positives to be readily identified by using a plasmid for bait cloning that contains a cycloheximide sensitizing gene (CYH2). False positive "prey" clones that activate the reporter gene in the absence of the bait are identified by counterselecting with cycloheximide to eliminate the bait plasmid (Bartel and Fields, 1997). Clones that have either no bait, true bait or false bait are then introduced by matings, and only clones that show lacZ expression specifically in the presence of the true bait are selected for further study. Positive clones that pass this test may be sequenced, and any portions of known proteins may be identified by database searches. In the case of novel proteins, one may isolate full length cDNAs by 5' and 3' RACE for further analysis. Subsequent studies using the two hybrid system may include mapping interacting domains. The functional significance of these interactions may be tested in the transgenic rescue system.

Using this system, a polypeptide that interacts with human Morc has been identified from a random human cDNA library transfected into Cos cells. A clone encoding human 123F2 (Genbank Accession number AF040703; murine clone Genbank Accession number AF132851) positively interacted with the human Morc (non-mutated) polypeptide. 123F2 has been characterized as a candidate tumor suppressor gene in humans that has homology to rat Maxp1, a protein that interacts with guanine nucleotide exchange factor Mss4. 123F2 is located in the homozygous deletion region of 3p21.3 in small cell lung cancer. Furthermore, it is expressed in a variety of tissues, including the testis.

5.12 Example 12

Morc Interactions in Cultured Cells

These studies may help demonstrate the in vivo relevance of interactions identified by two-hybrid analysis. In the literature, there are many examples in which coexpression of two proteins in cell lines has demonstrated protein-protein interactions, for example cFos and cJun (Corvello et al., 1995), the TNF receptors TR60 and TR85 (Moosmayer et al., 1994), and the Rag1 and Rag2 proteins. This approach takes advantage of Morc constructs that may be made for subcellular localization. Protein "pull-down" methods are a variant of immunoprecipitation studies and can offer a confirmatory procedure for validating candidate interactions (Weideman et al., 1997; Nocentini et al., 1997; Dombrosky-Ferlan and Corey, 1997).

To test specific candidate genes as Morc partners, one may cotransfect the FLAG-tagged Morc construct and the candidate partner(s) tagged with a second epitope, e.g., 6-His into COS-7 cells. One may then immunoprecipitate the Morc protein using anti-FLAG antibody and analyze the precipitate by SDS PAGE. Western blotting using commercially available monoclonal antibodies to the 6-His epitope (Qiagen) may confirm the presence of the partner in the precipitate. These same studies may be used to evaluate future mutant constructs for mapping interacting domains.

As a western control, one produce Morc protein by in vitro transcription/translation. The constructs shown previously (FIG. 16) may serve as templates for the reactions, using commercial kits ("MegaScript" and "Retic Lysate IVT," Ambion, Austin, Tex.) to generate protein. Nanogram amounts of unlabeled protein produced in this fashion may be sufficient to serve as a positive control for western blotting. $^{35}$S-methionine labeled Morc from in vitro translations may also serve as a test bed for determining whether a specific buffer condition allows quantitative precipitation in a simple system.

Alternatively, in vivo interactions may be studied by differentially tagging MORC and an interacting polypeptide. Fusion constructs were made in which MORC was tagged with one epitope such as FLAG and in which 123F2 was tagged with another epitope. These constructs were then transfected into COS cells, such as COS7 cells, and then exposed to the antibodies of the respective tags. Secondary antibodies suitable for calorimetric analysis, for example fluorescein, that recognize the primary antibodies may be employed. This type of experiment has been done with human MORC and human 123F2, which were tagged with different epitopes and transfected into cells. Under a microscope it was observed that the proteins interact and that the human 123F2 protein causes the human MORC protein to relocate from the nucleus to the cytoskeleton.

5.13 Example 13

Immunoprecipitation From Testis Extracts

Coimmunoprecipitation from testis tissue may provide biochemical proof that a protein interacts with Morc in vivo. These studies may use the high-affinity Morc-antisera that one may generate to immunoprecipitate native protein from testis extracts. Initial attempts to immunoprecipitate BLM protein from cell extracts succeeded in identifying several candidate interaction partners.

Initially, one may focus on optimizing Morc immunoprecipitation conditions using mammalian cell lines transfected with the FLAG-tagged Morc construct. Extracts may be prepared using a standard RIPA buffer (150 mM NaCl, 0.5% DOC, 0.1% SDS, 1.0% NP-40, 50 mM Tris pH 8.0). Morc protein may then be precipitated using anti-peptide Morc polyclonal sera and protein A conjugated beads (Pierce) as a starting point. Complexes may be analyzed by SDS PAGE. Extracts from pellets and supernatants may be probed with anti-FLAG antibody to confirm that FLAG-tagged Morc protein is quantitatively precipitated.

Once conditions for immunoprecipitating FLAG-tagged Morc using the Morc antisera have been optimized, one may attempt to immunoprecipitate native Morc along with its putative partner(s) from testis extracts under the same conditions. Precipitates may be analyzed by SDS PAGE for the presence of a band whose electrophoretic mobility corresponds to that of Morc. The identity of the band may be confirmed two ways. First, if two different Morc antisera are available (i.e. if immunization with both amino and carboxy terminal peptides or with native protein result in high titer antibody), the second polyclonal antibody may be used for confirmatory western blotting. Alternatively, competitor peptide may be used to block immunoprecipitation. Preimmune sera may be used as a negative control.

6.0 REFERENCES

The following references, to the extent that they provide exemplary procedural or other details supplementary to those set forth herein, are specifically incorporated herein by reference.

U.S. Pat. No. 4,196,265, issued Apr. 1, 1980.
U.S. Pat. No. 4,216,209, issued Aug. 5, 1980.
U.S. Pat. No. 4,237,224, issued Dec. 2, 1980.
U.S. Pat. No. 4,292,404, issued Sep. 29, 1981.
U.S. Pat. No. 4,329,332, issued May 11, 1982.
U.S. Pat. No. 4,335,041, issued Jun. 15, 1982.
U.S. Pat. No. 4,358,535, issued Nov. 9, 1982.
U.S. Pat. No. 4,407,944, issued Oct. 4, 1983.
U.S. Pat. No. 4,489,055, issued Dec. 18, 1984.
U.S. Pat. No. 4,554,101, issued Nov. 19, 1985.
U.S. Pat. No. 4,683,195, issued Jul. 28, 1987.
U.S. Pat. No. 4,683,202, issued Jul. 28, 1987.
U.S. Pat. No. 4,800,159, issued Jan. 24, 1989.
U.S. Pat. No. 4,873,191, issued Oct. 10, 1989.
U.S. Pat. No. 4,883,750, issued Nov. 28, 1989.
U.S. Pat. No. 4,913,908, issued Apr. 3, 1990.
U.S. Pat. No. 4,965,188, issued Oct. 23, 1990.
U.S. Pat. No. 4,987,071, issued Jan. 22, 1991.
U.S. Pat. No. 5,098,887, issued Mar. 24, 1992.
U.S. Pat. No. 5,145,684, issued Sep. 8, 1992.
U.S. Pat. No. 5,145,864, issued Sep. 8, 1992.
U.S. Pat. No. 5,176,995, issued Jan. 5, 1993.
U.S. Pat. No. 5,225,341, issued Jul. 6, 1993.
U.S. Pat. No. 5,238,921, issued Aug. 24, 1993.
U.S. Pat. No. 5,276,269, issued Jan. 4, 1994.
U.S. Pat. No. 5,279,721, issued Jan. 18, 1994.
U.S. Pat. No. 5,334,711, issued Aug. 2, 1994.
U.S. Pat. No. 5,348,978, issued Sep. 20, 1994.
U.S. Pat. No. 5,354,855, issued Oct. 11, 1994.
U.S. Pat. No. 5,359,045, issued Oct. 25, 1994.
U.S. Pat. No. 5,384,253, issued Jan. 24, 1995.
U.S. Pat. No. 5,399,346, issued Mar. 21, 1995.
U.S. Pat. No. 5,399,363, issued Mar. 21, 1995.
U.S. Pat. No. 5,449,661, issued Sep. 12, 1995.
U.S. Pat. No. 5,451,410, issued Sep. 19, 1995.
U.S. Pat. No. 5,466,468, issued Nov. 14, 1995.
U.S. Pat. No. 5,480,793, issued Jan. 2, 1996.
U.S. Pat. No. 5,482,852, issued Jan. 9, 1996.
U.S. Pat. No. 5,500,224, issued Mar. 19, 1996.
U.S. Pat. No. 5,508,468, issued Apr. 16, 1996.
U.S. Pat. No. 5,543,158, issued Apr. 6, 1996.
U.S. Pat. No. 5,550,318, issued Aug. 27, 1996.
U.S. Pat. No. 5,552,157, issued Sep. 3, 1996.
U.S. Pat. No. 5,552,397, issued Sep. 3, 1996.
U.S. Pat. No. 5,556,617, issued Sep. 17, 1996.
U.S. Pat. No. 5,565,213, issued Oct. 15, 1996.
U.S. Pat. No. 5,567,434, issued Oct. 22, 1996.
U.S. Pat. No. 5,580,579, issued Dec. 3, 1996.
U.S. Pat. No. 5,591,317, issued Jan. 7, 1997.
U.S. Pat. No. 5,602,306 issued Feb. 11, 1997
U.S. Pat. No. 5,610,288, issued Mar. 11, 1997.
U.S. Pat. No. 5,620,708, issued Apr. 15, 1997.
U.S. Pat. No. 5,631,359, issued May 20, 1997.
U.S. Pat. No. 5,639,940 issued Jun. 17, 1997
U.S. Pat. No. 5,641,515, issued Jun. 24, 1997.
U.S. Pat. No. 5,641,515, issued Jun. 24, 1997.

U.S. Pat. No. 5,656,016, issued Aug. 12, 1997.
U.S. Pat. No. 5,663,188, issued Sep. 2, 1997.
U.S. Pat. No. 5,697,899, issued Dec. 16, 1997.
U.S. Pat. No. 5,698,515, issued Dec. 16, 1997.
U.S. Pat. No. 5,710,134, issued Jan. 20, 1998.
U.S. Pat. No. 5,718,709, issued Feb. 17, 1998.
U.S. Pat. No. 5,720,936 issued Feb. 24, 1998
U.S. Pat. No. 5,723,307, issued Mar. 3, 1998.
U.S. Pat. No. 5,725,871, issued Mar. 10, 1998.
U.S. Pat. No. 5,738,868, issued Apr. 14, 1998.
U.S. Pat. No. 5,739,119, issued Apr. 14, 1998.
U.S. Pat. No. 5,741,516, issued Apr. 21, 1998.
U.S. Pat. No. 5,744,496, issued Apr. 28, 1998.
U.S. Pat. No. 5,747,470, issued May 5, 1998.
U.S. Pat. No. 5,756,353, issued May 26, 1998.
U.S. Pat. No. 5,759,829, issued Jun. 2, 1998.
U.S. Pat. No. 5,770,219, issued Jun. 23, 1998.
U.S. Pat. No. 5,779,708, issued Jul. 14, 1998.
U.S. Pat. No. 5,780,045, issued Jul. 14, 1998.
U.S. Pat. No. 5,783,208, issued Jul. 21, 1998.
U.S. Pat. No. 5,783,683, issued Jul. 21, 1998.
U.S. Pat. No. 5,789,573, issued Aug. 4, 1998.
U.S. Pat. No. 5,789,655 issued Aug. 4, 1998
U.S. Pat. No. 5,792,451, issued Aug. 11, 1998.
U.S. Pat. No. 5,795,587, issued Aug. 18, 1998.
U.S. Pat. No. 5,797,898, issued Aug. 25, 1998.
U.S. Pat. No. 5,800,990, issued Sep. 1, 1998.
U.S. Pat. No. 5,801,040, issued Sep. 1, 1998.
U.S. Pat. No. 5,801,154, issued Sep. 1, 1998
U.S. Pat. No. 5,804,212, issued Sep. 8, 1998.
Int. Pat. Appl. Publ. No. PCT/US87/00880.
Int. Pat. Appl. Publ. No. PCT/US89/01025.
Int. Pat. Appl. Publ. No. WO 84/03564.
Int. Pat. Appl. Publ. No. WO 88/10315.
Int. Pat. Appl. Publ. No. WO 88/10315.
Int. Pat. Appl. Publ. No. WO 89/06700.
Int. Pat. Appl. Publ. No. WO 89/06700.
Int. Pat. Appl. Publ. No. WO 90/03435.
Int. Pat. Appl. Publ. No. WO 91/03162.
Int. Pat. Appl. Publ. No. WO 92/07065.
Int. Pat. Appl. Publ. No. WO 93/15187.
Int. Pat. Appl. Publ. No. WO 93/23569.
Int. Pat. Appl. Publ. No. WO 94/02595.
Int. Pat. Appl. Publ. No. WO 94/13688.
Eur. Pat. Appl. Publ. No. EP 0273085.
Eur. Pat. Appl. Publ. No. EP 0360257.
Eur. Pat. Appl. Publ. No. EP 92110298.4.
Eur. Pat. Appl. Publ. No. EP 320,308.
Eur. Pat. Appl. Publ. No. EP 329,822.
Great Britain Pat. Appl. Publ. No. GB 2,202,328.
"Modem Applied Statistics With S-Plus," Venables W. N., Ripley, B. D. Springer-Verlag. New York, 1994.
"Remington's Pharmaceutical Sciences," 15th ed., pp. 1035–1038 and 1570–1580.
Adams et al., *J. Am. Chem. Soc.*, 105:661, 1983.
Agarwal and Riftina, "Synthesis and enzymatic properties of deoxyribooligonucleotides containing methyl and phenylphosphonates linkages," *Nucl. Acids Res.*, 6(9):3009–3023, 1979.

Agodoa, "African American study of kidney disease and hypertension (AASK)—clinical trial update," *Ethn. Dis.*, 8(2):249–253, 1998.

Albanese et al., "Transforming $p21^{ras}$ mutants and c-Ets-2 activate the cyclin D1 promoter through distinguishable regions," *J. Biol. Chem.*, 270:23589–23597, 1995.

Alderman, Madhavan, Ooi, Cohen, Sealey, Laragh, "Association of the renin-sodium profile with the risk of myocardial infarction in patients with hypertension," *New Eng. J. Med.*, 324(16):1098–1104, 1991.

Allan, Harmon, Kerr, In: Perspectives on mammalian cell death, Potten, C. S. ed., Oxford University Press, London, pp. 229–258, 1987.

Allan, Harmon, Roberts, "Spermatogonial apoptosis has three morphologically recognizable phases and shows no circadian rhythm during normal spermatogenesis in the rat," *Cell Prolif.*, 25(3):241–50, 1992.

Allen and Choun, "Large unilamellar liposomes with low uptake into the reticuloendothelial system," *FEBS Lett.*, 223:42–46, 1987.

Alphey et al., "twine, a cdc25 homolog that functions in the male and female germline of Drosophila," *Cell*, 69(6):977–88, 1992.

Altschul, Gish, Miller, Myers, Lipman, "Basic local alignment search tool," *J. Mol. Biol.*, 215(3):403–410, 1990.

Altschul, Madden, Schaffer, Zhang, Zhang, Miller, Lipman, "Gapped BLAST and PSI-BLAST: a new generation of protein database search programs," *Nucl. Acids Res.*, 25(17):3389–3402, 1997.

Armitage, Koch, Frydenlund, Orum, Batz, Schuster, "Peptide nucleic acid-anthraquinone conjugates: strand invasion and photoinduced cleavage of duplex DNA," *Nucl. Acids Res.*, 25(22):4674–4678, 1997.

Armitage, Ly, Koch, Frydenlund, Orum, Batz, Schuster, "Peptide nucleic acid-DNA duplexes: long range hole migration from an internally linked anthraquinone," *Proc. Natl. Acad Sci. USA*, 94(23):12320–12325, 1997.

Arnheim and Shibata, "DNA mismatch repair in mammals: role in disease and meiosis," *Curr. Opin. Genet. Dev.*, 7(3):364–70, 1997.

Arshady, "In vivo targeting of colloidal carriers by novel graft copolymers," *J. Mol. Recognit.*, 9(5–6):536–542, 1996.

Asseline and Thuong, *Tetrahedron Lett.*, 30(19):2521–2524, 1989.

Baichwal and Sugden, "Vectors for gene transfer derived from animal DNA viruses: Transient and stable expression of transferred genes," In: *Gene transfer*, Kucherlapati R, ed., New York: Plenum Press, pp. 117–148, 1986.

Baker, Bronner, Zhang, Plug, Robatzek, Warren, Elliott, Yu, Ashley, Arnheim et al., "Male mice defective in the DNA mismatch repair gene PMS2 exhibit abnormal chromosome synapsis in meiosis," *Cell*, 82(2):309–319, 1995.

Balazsovits et al., "Analysis of the effect of liposome encapsulation on the vesicant properties, acute and cardiac toxicities, and antitumor efficacy of doxorubicin," *Cancer Chemother. Pharmacol.*, 23:81–86, 1989.

Barany and Merrifield, "A chromatographic method for the quantitative analysis of the deprotection of dithiasuccinoyl (Dts) amino acids," *Ana. Biochem.*, 95(1):160–170, 1979.

Barlow, Hirotsune, Paylor, Liyanage, Eckhaus, Collins, Shiloh, Crawley, Ried, Tagle, Wynshaw-Boris, "Atm-deficient mice: a paradigm of ataxia telangiectasia," *Cell*, 86(1):159–171, 1996.

Barlow, Liyanage, Moens, Deng, Ried, Wynshaw-Boris, "Partial rescue of the prophase I, defects of Atm-deficient mice by p53 and p21 null alleles," *Nat. Genet.*, 17(4):462–466, 1997.

Bartel and Fields, "The yeast two-hybrid system," Oxford, England: Oxford University Press, 1997.

Baselga and Mendelsohn, "Receptor blockade with monoclonal antibodies as anti-cancer therapy," *Pharmacology & Therapeutics*, 64(1): 127–54, 1994.

Baselga, Norton, Masui, Pandiella, Coplan, Miller, Mendelsohn, "Antitumor effects of doxorubicin in combination with anti-epidermal growth factor receptor monoclonal antibodies," *J. Nat. Cancer Inst.*, 85(16):1327–33, 1993.

Bast, Feeney, Lazarus, Nadler, Colvin, Knapp, "Reactivity of a monoclonal antibody with human ovarian carcinoma," *J. Clin. Invest.*, 68:1331–1337, 1981.

Bast, Jacobs, Berchuck, "Editorial: Malignant transformation of ovarian epithelium," *J. Natl. Cancer Inst.*, 84:556–558, 1992.

Bast, Klug, St. John, Jenison, Niloff, Lazarus, Berkowitz, Leavitt, Griffiths, Parker, Zurawski, Knapp, "A radioimmunoassay using a monoclonal antibody to monitor the course of epithelial ovarian cancer," *New Engl. J. Med.*, 309:883–887, 1983.

Beamer et al., "Juvenile spermatogonial depletion Osd): a genetic defect of germ cell proliferation of male mice," *Biology of Reproduction*, 38(4):899–908, 1988.

Bedell, Jenkins, Copeland, "Mouse models of human disease. Part I: techniques and resources for genetic analysis in mice," *Genes Dev.*, 11(1):1–10, 1997.

Benes et al., "Direct primer walking on P1 plasmid DNA," *Biotechniques*, 23(1):98–100, 1997.

Benvenisty and Reshef, "Direct introduction of genes into rats and expression of the genes," *Proc. Natl. Acad Sci. USA.*; 83(24): 9551–9555, 1986.

Berchuck, Kamel, Whitaker, Kems, Olt, Kinney, Soper, Dodge, Clarke-Pearson, Marks, McKenzie, Yin, Bast, "Overexpression of HER-2/neu is associated with poor survival in advanced epithelial ovarian cancer," *Cancer Res.*, 50:4087–4091, 1990.

Berchuck, Kohler, Marks, Wiseman, Boyd, Bast, "The p53 tumor suppressor gene frequently is altered in gynecologic cancers," *Am. J. Obstet. Gynecol.*, 170:246–252, 1994.

Berchuck, Rodriguez, Kamel, Dodge, Soper, Clarke-Pearson, Bast, "Epidermal growth factor receptor expression in normal ovarian epithelium and ovarian cancer. I. Correlation of receptor expression with prognostic factors in patients with ovarian cancer," *Am. J Obstet. Gynecol.*, 164:669–674, 1991.

Berchuck, Rodriguez, Olt, Whitaker, Boente, Arrick, Clarke-Pearson, Bast, "Regulation of growth of normal ovarian epithelial cells and ovarian cancer cell lines by transforming growth factor-β," *Am. J. Obstet. Gynecol.*, 166:676–684, 1992.

Berenbaum, "Synergy, additivism and antagonism in immunosuppression. A critical review," *Clin. Exp. Immunol.*, 28:1–18, 1977.

Berger, Wilson, Wolf, Tonchev, Milla, Kim, "Predicting coiled coils by use of pairwise residue correlations," *Proc. Natl. Acad Sci. USA*, 92(18):8259–8263, 1995.

Besmer, Manova, Duttlinger, Huang, Packer, Gyssler, Bachvarova, "The kit-ligand (steel factor) and its receptor c-kit/W: pleiotropic roles in gametogenesis and melanogenes is," In: *Development—Supplement*, Sloan-Kettering Institute, p. 125–37, 1993.

Beumer, Roepers-Gajadien, Gademan, Rutgers, de Rooij, "P21 (Cip1/WAF1) expression in the mouse testis before and after X irradiation," *Mol. Repro. Dev.*, 47(3):240–247, 1997.

Biagini, G., Zoli, M., Torri, C., Boschi, S. Vantaggiato, G., Ballestri, M., Baraldi, A., Agnati, L. F. Protective effects of delapril, indapamide and their combination chronically administered to stroke-prone spontaneously hypertensive rats fed a high-sodium diet. *Clin. Sci.* (Colch) 93(5):401–411, 1997.

Bishop, "The information content of phase-known matings for ordering genetic loci [published erratum appears in *Genet Epidemiol.*, 4(2):159, 1987]," *Genet Epidemiol*, 2(4):349–61, 1985.

Bitgood, Shen, McMahon, "Sertoli cell signaling by Desert hedgehog regulates the male germline," *Curr. Biol.*, 6(3):298–304, 1996.

Blanco-Rodriguez and Martinez-Garcia, "Spontaneous germ cell death in the testis of the adult rat takes the form of apoptosis: re-evaluation of cell types that exhibit the ability to die during spermatogenesis," *Cell Prolif.*, 29(1):13–31, 1996.

Blendy, Kaestner, Weinbauer, Nieschlag, Schutz, "Severe impairment of spermatogenesis in mice lacking the CREM gene," *Nature*, 380(6570):162–165, 1996.

Boffa, "Thrombomodulin in human brain microvasculature," *Lupus*, 4(2): 165–166, 1995.

Boffa, Berard, Sugi, McIntyre, "Antiphosphatidylethanolamine antibodies as the only antiphospholipid antibodies detected by ELISA.II. Kininogen reactivity," *J. Rheumatol.*, 23(8):1375–1379, 1996.

Bonham, Brown, Boyd, Brown, Bruckenstein, Hanvey, Thomson, Pipe, Hassman, Bisi, et al., "An assessment of the antisense properties of Rnase H-competent and steric-blocking oligomers," *Nucl. Acids Res.*, 23(7):1197–1203, 1995.

Bourlais, Acar, Zia, Sado, Needham, Leverge, "Ophthalmic drug delivery systems—recent advances," *Prog. Retin Eye Res.*, 17(1):33–58, 1998.

Bourne, Sanders, McCormick,. "The GTPase superfamily: conserved structure and molecular mechanism," *Nature*, 349:117–127, 1991.

Boysen, Simon, Hood, "Fluorescence-Based Sequencing Directly From Bacterial and P1-Derived Artificial Chromosomes," *Biotechniques*, 23(6):978 ff, 1997.

Braun, "Every sperm is sacred—or is it?" *Nat. Genet.*, 18(3):202–204, 1998.

Brink, "Protein synthesis during spermatogenesis in *Drosophila melanogaster*," *Mutat. Res.*, 5(1):1924, 1968.

Brinkworth et al., "Identification of male germ cells undergoing apoptosis in adult rats," *J. Reprod. Fertil.*, 105(1):25–33, 1995.

Brinster et al., "Factors affecting the efficiency of introducing foreign DNA into mice by microinjecting eggs," *Proc. Natl. Acad. Sci. USA*, 82(13):4438–4442, 1985.

Broido et al., Biochem. *Biophys. Res. Commun.*, 119:663, 1984.

Brown, "Some properties of the Spearmann estimator in bioassay," *Biometrika*, 48:293–302, 1961.

Brown-Shiner, Johnson, Hill, Bruskin, "Effect of protein tyrosine phosphatase 1B expression on transformation by the human neu oncogene," *Cancer Res.*, 52:478–482, 1992.

Cai, Hales, Robaire, "Induction of apoptosis in the germ cells of adult male rats after exposure to cyclophosphamide," *Biol. Reprod.*, 56(6):1490–7, 1997.

Caldovic and Hackett Jr., "Development of position-independent expression vectors and their transfer into transgenic fish," *Mol. Mar. Biol. Biotechnol.*, 4(1):51–61, 1995.

Calvo, Vila-Jato, Alonso, "Effect of lysozyme on the stability of polyester nanocapsules and nanoparticles: stabilization approaches," *Biomaterials*, 18(19):1305–1310, 1997.

Calvo, Vila-Jato, Alonso, "Improved ocular bioavailability of indomethacin by novel ocular drug carriers," *J. Pharm. Pharmacol.*, 48(11):1147–1152, 1996.

Campa, Cnang, Vedia, Reep, Lapetina, "Inhibition of Ras-induced germinal vesicle breakdown in Xenopus oocytes by Rap-1B," *Biochem. Biophys. Res. Commun.*, 174:1–5, 1991.

Campbell, "Monoclonal Antibody Technology, Laboratory Techniques in Biochemistry and Molecular Biology," Vol. 13, Burden and Von Knippenberg, Eds. pp. 75–83, Elsevier, Amsterdam, 1984.

Capaldi et al., "Changes in order of migration of polypeptides in complex III and cytochrome C oxidase under different conditions of SDS polyacrylamide gel electrophoresis," *Biochem. Biophys. Res. Commun.*, 74(2):425–433, 1977.

Capaldi et al., "Isolation of a major hydrophobic protein of the mitrochondrial inner membrane," *Biochem. Biophys. Res. Commun.*, 55(3):655–659,1973.

Capaldi, "Identification of the major enzymic activities of the mitochondrial inner membrane in terms of their migration in sodium dodecyl sulfate polyacrylamide gel electrophoresis," *Aech. Biochem. Biophys.*, 163(1):99–105, 1974.

Capecchi, "High efficiency transformation by direct microinjection of DNA into cultured mammalian cells," *Cell*, 22(2):479–488, 1980.

Carlsson, Sandler, Jansson, "Influence of the neurotoxin capsaicin on rat pancreatic islets in culture, and on the pancreatic islet blood flow of rats," *Eur. J. Pharmacol.*, 312(1):75–81, 1996.

Caruthers et al., In: *Genetic Engineering*, Settlow: and Hollander (Eds.), Plenum Press, New York, 1982.

Carver, Dalrymple, Wright, Cottom, Reeves, Gibson, Keenan, Barrass, Scott, Colman, et al., "Transgenic livestock as bioreactors: stable expression of human alpha-1-antitrypsin by a flock of sheep," *Biotechnology NY*, 11(1 1):1263–1270, 1993.

Castrillon, Gonczy, Alexander, Rawson, Eberhart, Viswanathan, DiNardo, Wasserman, "Toward a molecular genetic analysis of spermatogenesis in *Drosophila melanogaster*: characterization of male-sterile mutants generated by single P element mutagenesis," *Genetics*, 135:489–505, 1993.

Cattanach, Pollard, Hawker, "Sex-reversed mice: XX and XO males," *Cytogenetics*, 10(5):318–337, 1971.

Cech et al., "In vitro splicing of the ribosomal RNA precursor of Tetrahymena: involvement of a guanosine nucleotide in the excision of the intervening sequence," *Cell*, 27(3 Pt 2):487–496, 1981.

Chamorro, Vila, Ascaso, Elices, Schonewille, Blanc, "Blood pressure and functional recovery in acute ischemic stroke," *Stroke*, 29(9):1850–1853, 1998.

Chandran, Roy, Mishra, "Recent trends in drug delivery systems: liposomal drug delivery system—preparation and characterisation," *Indian J. Exp. Biol.*, 35(8):801–809, 1997.

Chang et al., "Foreign gene delivery and expression in hepatocytes using a hepatitis B virus vector," *Hepatology*, 14:134A, 1991.

Chen and Okayama, "High-efficiency transformation of mammalian cells by plasmid DNA," *Mol. Cell. Biol.*, 7:2745–2752, 1987.

Chen et al., *Nucl. Acids Res.*, 20:4581–4589, 1992.

Chowrira and Burke, *Nuc. Acids Res.*, 20:2835–2840, 1992.

Chresta, Masters, Hickman, "Hypersensitivity of human testicular tumors to etoposide-induced apoptosis is associated with functional p53 and a high Bax:Bcl-2 ratio," *Cancer Res.*, 56(8):1834–41, 1996.

Christensen, Fitzpatrick, Gildea, Petersen, Hansen, Koch, Egholm, Burchardt, Nielsen, Coull et al., "Solid-phase synthesis of peptide nucleic acids," *J. Pept. Sci.*, 1(3):175–183, 1995a.

Christensen, Johansen, Marker, Thomsen, "Circulating intracellular adhesion molecule-1 (ICAM-1) as an early and sensitive marker for virus-induced T cell activation," *Clin. Exp. Immunol.*, 102(2):268–273, 1995b.

Chubb, "Genetically defined mouse models of male infertility," *J. Andrology*, 10(2):77–88, 1989.

Chubet and Brizzard, "Vectors for expression and secretion of FLAG epitope-tagged proteins in mammalian cells," *Biotechniques*, 20(1):136–41, 1996.

Clayman, Liu, Overholt, Mobley, Wang, Janot, Goepfert, "Gene therapy for head and neck cancer: comparing the tumor suppressor gene p53 and a cell cycle regulator WAF1/CIP1 (p21)," *Arch. Otolaryngol.*, 122(5):489–93, 1996.

Clermont, "Quantitative analysis of spematogenesis of the rat: a revised model for the renewal of spermatogonia," *Am. J. Anat.*, 111:111–129, 1962.

Cobb, Reddy, Park, Handel, "Analysis of expression and function of topoisomerase I and II during meiosis in male mice," *Mol. Reprod. Dev.*, 46(4):489–498, 1997.

Coffin, "Retroviridae and their replication," In: *Virology*, Fields B N, Knipe D M, ed,. New York: Raven Press, pp. 1437–1500, 1990.

Cohen, "Designing antisense oligonucleotides as pharmaceutical agents," *Trends Pharmacol. Sci.*, 10(11):435–437, 1989.

Collins and Olive, "Reaction conditions and kinetics of self-cleavage of a ribozyme derived from Neurospora VS RNA," *Biochem.*, 32(11):2795–2799, 1993.

Collins and Uhler, "Characterization of PKIgamma, a novel isoform of the protein kinase inhibitor of cAMP-dependent protein kinase," *J. Biol. Chem.*, 272(29):18169–78, 1997.

Connor, Bertwistle, Mee, Ross, Swift, Grigorieva, Tybulewicz, Ashworth, "Tumorigenesis and a DNA repair defect in mice with a truncating Brca2 mutation," *Nat. Genet.*, 17(4):423–430, 1997.

Connor, Bertwistle, Mee, Ross, Swift, Grigorieva, Tybulewicz, Ashworth, "Tumorigenesis and a DNA repair defect in mice with a truncating Brca2 mutation," *Nat. Genet.*, 17(4):423–430, 1997.

Cook, Rubinfield, Albert, McCormick, "RapV12 antagonizes Ras-dependent activation of ERK1 and ERK2 by LPA and EGF in Rat-1 fibroblasts," *EMBO J.*, 12:3475–3485, 1993.

Cooke et al., "A murine homologue of the human DAZ gene is autosomal and expressed only in male and female gonads," *Hum. Mol. Genet.*, 5(4):513–6, 1996.

Corey, "Peptide nucleic acids: expanding the scope of nucleic acid recognition," *Trends Biotechnol.*, 15(6):224–229, 1997.

Corvello et al., "Expression and characterization of mouse cFos protein using the baculovirus expression system: ability to form ftmctional AP-1 complex with coexpressed cJun protein.," *Cell. Mol. Biol. Res.*, 41(6):527–35, 1995.

Couch et al., "Immunization with types 4 and 7 adenovirus by selective infection of the intestinal tract," *Am. Rev. Resp. Dis.*, 88:394–403, 1963.

Coune, "Liposomes as drug delivery system in the treatment of infectious diseases: potential applications and clinical experience," *Infection*, 16(3):141–147, 1988.

Coupar et al., "A general method for the construction of recombinant vaccinia virus expressing multiple foreign genes," *Gene*, 68:1–10, 1988.

Courtot et al., "The Drosophila cdc25 homolog twine is required for meiosis," *Development*, 116(2):405–16, 1992.

Couvreur et al., "Nanocapsules, a new lysosomotropic carrier," *FEBS Lett.*, 84:323–326, 1977.

Couvreur et al., "Tissue distribution of antitumor drugs associated with polyalkylcyanoacrylate nanoparticles," *J. Pharm. Sci.*, 69(2):199–202, 1980.

Couvreur, "Polyalkyleyanoacrylates as colloidal drug carriers," *Crit. Rev. Ther. Drug Carrier Syst.*, 5:1–20, 1988.

Cox, "Regression Models and Life Tables" *J. Royal Statistical Society*, B, 34:187–220, 1972.

Cozzi, Tucker, Langford, Pino-Chavez, Wright, O'Connell, Young, Lancaster, McLanghlin, Hunt, Bordin, White, "Characterization of pigs transgenic for human decay-accelerating factor," *Transplantation*, 64(10):1383–1392, 1997.

Culver et al., "In vivo gene transfer with retroviral vector-producer cells for treatment of experimental brain tumors," *Science*, 256:1550–1552, 1992.

Curiel, Agarwal, Wagner, Cotten, "Adenovirus enhancement of transferrin-polylysine-mediated gene delivery," *Proc. Natl. Acad. Sci. USA*, 88(19):8850–8854, 1991.

Cusack, Spitz, Nguyen, Zhang, Cristiano, Roth, "High levels of gene transduction in human lung tumors following intralesional injection of recombinant adenovirus," *Cancer Gene Therapy*, 3(4):245–249, 1996.

Cushman and Ondetti, "Inhibitors of ACE for treatment of hypertension," *Biochem. Pharmacol.*, 19:1871, 1980.

Damge, Vonderscher, Marback, Pinget, "Poly(alkyl cyanoacrylate) nanocapsules as a delivery system in the rate for octreotide, a long-acting somatostatin analogue," *J. Pharm. Pharmacol.*, 49(10):949–954, 1997.

De Mesmaeker et al., "Antisense oligonucleotides," *Acc. Chem. Res.*, 28:366–374, 1995.

Deira, Corbacho, Bondia, Lerma, Gascon, Martin, Garcia, Tabernero, "Captopril hepatotoxicity in a case of renal crisis due to-systemic sclerosis," *Nephrol. Dial. Transplant*, 12(8):1717–1718, 1997.

del Castillo, Trabucco, De la Balze, *J. Clin. Endocrinol.*, 7:493–500, 1947.

Dent et al., "Regulation of Raf-1 and Raf-1 mutants by Ras-dependent and Ras-independent mechanisms in vitro [published erratum appears in *Mol. Cell. Biol.*, Sep; 15(9):5203, 1995], *Mol. Cell. Biol.*, 15(8): 4125–35, 1995.

Dix, Allen, Collins, Mori, Nakamura, Poormanallen, Goulding, Eddy, "Targeted gene disruption of Hsp70-2 results in failed meiosis, germ cell apoptosis, and male infertility," *Proc. Natl. Acad. Sci. USA*, 93(8):3264–3268, 1996.

Dobson, Pearlman, Karaiskakis, Spyropoulos, Moens, "Synaptonemal complex proteins: occurrence, epitope mapping and chromosome disjunction," *J. Cell Sci.*, 107(Pt 10):2749–27606 1994.

Dombrosky-Ferlan and Corey, "Yeast two-hybrid in vivo association of the Src kinase Lyn with the proto-oncogene product Cbl but not with the p85 subunit of PI 3-kinase," *Oncogene*, 14(17):2019–24, 1997.

Donehower, Harvey, Slagle, McArthur, Montgomery Jr., Butel, Bradley, "Mice deficient for p53 are developmentally normal but suceptible to spontaneous tumours," *Nature*, 356(6366):215–221, 1992.

Dorsch, Hock, Kunzendorf, Diamantstein, Blankenstein, "Macrophage colony-stimulating factor gene transfer into tumor cells induces macrophage infiltration but not tumor suppression," *Eur. J. Immunol.*, 23(1):186–90, 1993.

Douglas, Davis, Illum, "Nanoparticles in drug delivery," *Crit. Rev. Ther. Drug Carrier Syst.*, 3(3):233–261, 1987.

Dropulic, Lin, Martin, Jeang, "Functional characterization of a U5 ribozyme: intracellular suppression of human immunodeficiency virus type I expression," *J. Virol.*, 66(3): 1432–41, 1992.

Dubensky et al., "Direct transfection of viral and plasmid DNA into the liver or spleen of mice," *Proc. Nat. Acad. Sci. USA*, 81:7529–7533, 1984.

Dueholm, Motawia, Pedersen, Nielsen, Lundt, "Synthesis of 3'-alkylthio-2',3'-dideoxy nucleosides with potential anti-HIV activity from 2-deoxy-D-ribose, using a phosphorus pentoxide reagent," *Arch. Pharm.* (Weinheim), 325(9):597–601, 1992.

Dzau, "Vascular renin-angiotensin system and vascular protection," *J. Cardiovasc. Pharmacol.*, 22(Suppl.) 5:S1–S9, 1993.

Eberhart and Wasserman, "The pelota locus encodes a protein required for meiotic cell division: an analysis of G2/M arrest in Drosophila spermatogenesis," *Development*, 121(10):3477–86, 1995.

Eberhart, Maines, Wasserman, "Meiotic cell cycle requirement for a fly homologue of human Deleted in Azoospermia," *Nature*, 381(6585):783–5, 1996.

Ebert, Selgrath, DiTullio, Denman, Smith, Memon, Schindler, Monastersky, Vitale, Gordon, "Transgenic production of a variant of human tissue-type plasminogen activator in goat milk: generation of transgenic goats and analysis of expression," *Biotechnology NY*, 9(9):835–838, 1991.

Edelmann, Cohen, Kane, Lau, Morrow, Bennett, Umar, Kunkel, Cattoretti, Chaganti, Pollard, Kolodner, Kucherlapati, "Meiotic pachytene arrest in MLH1-deficient mice," *Cell*, 85(7):1125–1134, 1996.

Edwards and Bishop, "On the origin and frequency of Y chromosome deletions responsible for severe male infertility," *Mol. Hum. Reprod.*, 3(7):549–54, 1997.

Egholm, Buchardt, Christensen, Behrens, Freier, Driver, Berg, Kim, Norden, Nielsen, "PNA hybridizes to complementary oligonucleotides obeying the Watson-Crick hydrogen-bonding rules," *Nature*, 365(6446):566–568, 1993.

Egli, Usman, Rich, "Conformational influence of the ribose 2'-hydroxyl group: crystal structures of DNA-RNA chimeric duplexes," *Biochem.*, 32(13):3221–3237, 1993.

Eglitis and Anderson, "Retroviral vectors for introduction of genes into mammalian cells," *Biotechniques* 6(7):608–614, 1988.

Eglitis, Kantoff, Kohn, Karson, Moen, Lothrop, Blaese, Anderson, "Retroviral-mediated gene transfer into hemopoietic cells," *Avd. Exp. Med. Biol.*, 241:19–27, 1988.

El-Deiry et al., "WAF1, a potential mediator of p53 tumor suppression," *Cell*, 75:817–825, 1993.

Ellis et al., "The Bloom's syndrome gene product is homologous to RecQ helicases," *Cell*, 83(4):655–66, 1995.

Elroy-Stein and Moss, "Cytoplasmic expression system based on constitutive synthesis of bacteriophage T7 RNA polymerase in mammalian cells," *Proc. Natl. Acad. Sci. USA*, 87:6743–7, 1990.

Elson, Wang, Daugherty, Morton, Zhou, Campos-Torres, Leder, "Pleiotropic defects in ataxia-telangietasia protein-deficient mice," *Proc. Natl. Acad. Sci. USA*, 93(23):13084–13089, 1996.

Eppig and Nadeau, "Comparative maps: the mammalian jigsaw puzzle," *Curr. Opin. Genet. Dev.*, 5(6):709–16, 1995.

Erickson, "Mouse models of human genetic disease: which mouse is more like a man?" *Bioessays*, 18(12):993–8, 1996.

Faller and Baltimore, "Liposome encapsulation of retrovirus allows efficient super infection of resistant cell lines," *J. Virol.*, 49(1):269–272, 1984.

Fan, Baselga, Masui, Mendelsohn, "Antitumor effect of anti-epidermal growth factor receptor monoclonal antibodies plus cis-diamminedichloroplatinum on well established A431 cell xenografts," *Cancer Res.*, 53(19):4637–42, 1993.

Fearon et al., "Karyoplasmic interaction selection strategy: a general strategy to detect protein-protein interactions in mammalian cells," *Proc. Natl. Acad. Sci. USA*, 89(17):7958–62, 1992.

Fechheimer et al., "Transfection of mammalian cells with plasmid DNA by scrape loading and sonication loading," *Proc. Natl. Acad. Sci. USA*, 84:8463–8467, 1987.

Feig, Bast, Knapp, Cooper, "Somatic activation of RasK gene in a human ovarian carcinoma," *Science*, 223:698–700, 1984.

Ferkol, Lindberg, Chen, Perales, Crawford, Ratnoff, Hanson, "Regulation of the phosphoenolpyruvate carboxykinase/human factor IX gene introduced into the livers of adult rats by receptor-mediated gene transfer," *FASEB J.*, 7(11):1081–1091, 1993.

Ferrari, Fornasiero, Isetta, "MTT calorimetric assay for testing macrophage cytotoxic activity in vitro," *J. Immunol. Methods*, 131:165–172, 1990.

Finney, "Statistical Methods in Biologic assays," Third Edition. New York Macmillan, 374–401, 1978.

Fodor et al., "Light-directed, spatially addressable parallel chemical synthesis," *Science*, 251(4995):767–773, 1991.

Footer, Egholm, Kron, Coull, Matsudaira, "Biochemical evidence that a D-loop is part of a four-stranded PNA-DNA bundle. Nickel-mediated cleavage of duplex DNA by a Gly-Gly-His bis-PNA," *Biochemistry*, 35(33):10673–10679, 1996.

Forster and Symons, "Self-cleavage of plus and minus RNAs of a virusoid and a structural model for the active sites," *Cell*, 49:211–220, 1987.

Fraley et al., "Entrapment of a bacterial plasmid in phospholipid vesicles: Potential for gene transfer," *Proc. Natl. Acad. Sci. USA*, 76:3348–3352, 1979.

Frankel and Mills, "Peptide and lipid growth factors decrease cisplatin-induced cell death in human ovarian cancer cells," *Clin. Cancer Res.*, 2:1307–1313, 1996.

Franz, Mueller, Haartong, Frey, Katus, "Transgenic animal models: new avenues in cardiovascular physiology," *J. Mol. Med.*, 75(2):115–119, 1997.

Freifelder et al., "Dialysis of small samples in agarose gels," *Anal. Biochem.*, 123(1):83–85, 1982.

Freifelder et al., "Studies on *Escherichia coli* sex factors. I. Specific labeling of F'Lac DNA," *J. Mol. Biol.*, 32(1):15–23, 1968a.

Fresat and Puglisi, "Application of liposomes as potential cutaneous drug delivery systems. In vitro and in vivo investigation with radioactively labelled vesicles," *J. Drug Target*, 4(2):95–101, 1996.

Freshner, "Animal Cell Culture: a Practical Approach", Second Edition, Oxford/New York, IRL Press, Oxford University Press, 1992.

Frohlich, *Hypertension*, 4(Suppl.):S15–S19, 1986.

Frohman, Downs, Kashio, Brinster, "Tissue distribution and molecular heterogeneity of human growth hormone-releasing factor in the transgenic mouse," *Endocrinology*, 127(5):2149–2156, 1990.

Frohman, In: PCR™ *Protocols: A Guide to Methods and Applications*, Academic Press, New York, 1990.

Fromm, Taylor, Walbot, "Expression of genes transferred into monocot and dicot plant-cells by electroporation," *Proc. Natl. Acad. Sci. USA*, 82(17):5824–5828, 1985.

Frommer, McDonald, Millar, Collis, Watt, Grigg, Molloy, Paul, "A genomic sequencing protocol that yields a positive display of 5-methylcytosine residues in individual DNA strands," *Proc. Natl. Acad. Sci. USA* , 89(5):1827–1831, 1992.

Gabizon and Papahadjopoulos, "Liposomes formulations With prolonged circulation time in blood and enhanced uptake by tumors," *Proc. Natl. Acad. Sci. USA*, 85:6949–6953, 1988.

Gambacorti-Passerini, Mologni, Bertazzoli, le Coutre, Marchesi, Grignani, Nielsen, "In vitro transcription and translation inhibition by anti-promyelocytic leukemia (PML)/retinoic acid receptor alpha and anti-PML peptide nucleic acid," *Blood*, 88(4):1411–1417, 1996.

Gao and Huang, "Cytoplasmic expression of a reporter gene by co-delivery of T7 RNA polymerase and T7 promoter sequence with cationic liposomes," *Nucl. Acids Res.*, 21:2867–2872, 1993.

Gefter et al., *Somatic Cell Genet.* 3:231–236, 1977.

Gerlach et al., "Construction of a plant disease resistance gene from the satellite RNA of tobacco rinspot virus," *Nature* (London), 328:802–805, 1987.

Ghosh and Bachhawat, "Targeting of liposomes to hepatocytes," In: *Liver diseases, targeted diagnosis and therapy using specific receptors and ligands*, Wu G, Wu C ed., New York:
Marcel Dekker, pp. 87–104, 1991.

Ghosh-Choudhury, Haj-Ahmad, Graham, "Protein IX, a minor component of the human adenovirus capsid, is essential for the packaging of full-length genomes," *EMBO J.*, 6:1733–1739, 1987.

Gibson, Leung, Squire, Hill, Arima, Goss, Hogg, Mills, "Identification, cloning and characterization of a novel human T cell specific tyrosine kinase located at the hematopoietin complex on chromosome 5q," *Blood*, 82:1561–1572, 1993.

Gill, Hamel, Zhe, Zachsenhaus, Gallie, Phillips, "Characterization of the human RB1 promoter and of elements involved in transcriptional regulation," *Cell Growth and Differentiation*, 5(5):467–474, 1994.

Girardi, Mielnik, Schlegel, "Submicroscopic deletions in the Y chromosome of infertile men," *Hum. Reprod.*, 12(8):1635–41, 1997.

Girgis, Etriby, Ibrahim, Kahil, "Testicular biopsy in azoospermia. A review of the last ten years' experiences of over 800 cases," *Fertil. Steril.*, 20(3):467–477, 1969.

Goding, "Monoclonal Antibodies: Principles and Practice," pp. 60–74. 2nd Edition, Academic Press, Orlando, Fla., 1986.

Goldstein and Doi, "Prokaryotic promoters in biotechnology," Biotechnol. *Annu. Rev.*, 1:105–128, 1995.

Gomez-Foix, Coats, Baque, Alam, Gerard, Newgard, "Adenovirus-mediated transfer of the muscle glycogen phosphorylase gene into hepatocytes confers altered regulation of glycogen," *J. Biol. Chem.* 267:25129–25134, 1992.

Good and Nielsen, "Progress in developing PNA as a gene-targeted drug," *Antisense Nucl. Acid Drug Dev.*, 7(4):431–437, 1997.

Gopal, "Gene transfer method for transient gene expression, stable transfection, and cotransfection of suspension cell cultures," *Mol. Cell Biol.*, 5:1188–1190, 1985.

Gordon et al., "Analysis of the hotfoot (ho) locus by creation of an insertional mutation in a transgenic mouse," *Developmental Biology*, 137(2):349–58, 1990.

Gossen and Bujard, "Tight control of gene expression in mammalian cells by tetracycline responsive promoters," *Proc. Natl. Acad. Sci. USA*, 89:5547–5551, 1992.

Graff, Herman, Lapidus, Chopra, Xu, Jarrard, Isaacs, Pitha, Davidson, Baylin, "E-cadherin expression is silenced by DNA hypermethylation in human breast and prostate carcinomas," *Cancer Res.*, 55(22):5195–5199, 1995.

Graham and Prevec, "Adenovirus-based expression vectors and recombinant vaccines," *Biotechnology*, 20:363–390, 1992.

Graham and Prevec, "Manipulation of adenovirus vector," In: *Methods in Molecular Biology: Gene Transfer and Expression Protocol*, E. J. Murray (ed.), Clifton, N.J.: Humana Press, 7:109–128, 1991.

Graham and van der Eb, "Transformation of rat cells by DNA of human adenovirus 5," *Virology*, 54(2):536–539, 1973.

Graham et al., "Characteristics of a human cell line transformed by DNA from human adenovirus type 5", *J. Gen. Virol.*, 36:59–72, 1977.

Grambsch and Therneau, "Proportional Hazards Tests and Diagnostics Based On Weighted Residuals," *Biometrika*, 81:5515–5526, 1994.

Green, "Linkage, recombination and mapping," In: *Probability in Animal Breeding Experiments*, E. L. Green, ed., MacMillian: New York. p. 77–113, 1981.

Gribskov and Burgess, *Nucl. Acids Res.* 14:6745, 1986, as described by Schwartz and Dayhoff, eds., In: *Atlas of Protein Sequence and Structure*, National Biomedical Research Foundation, pp. 353–358, 1979.

Grunhaus and Horwitz, "Adenovirus as cloning vector," *Seminar in Virology*, 3:237–252, 1992.

Guerrier-Takada, Gardiner, Marsh, pace, Altman, "The RNA moiety of ribonuclease P is the catalytic subunit of the enzyme," *Cell*, 35:849, 1983.

Gum, Lengyel, Juarez, Chen, Sato, Seiki, Boyd, "Stimulation of 92-kDa gelatinase B promoter activity by ras is mitogen-activated protein kinase 1-independent and requires multiple transcription factor binding sites including closely spaced PEA3/ets and AP-1 sequences," *J. Biol. Chem.*, 271(18):10672–10680, 1996.

Gyurko, Tran, Phillips, "Time course of inhibition of hypertension by antisense oligonucleotides targeted to $AT_1$ angiotensin receptor mRNA in spontaneously hypertensive rats," *Am. J. Hypertens.*, 10:565–625, 1997.

Gyurko, Wielbo, Phillips, "Antisense inhibition of $AT_1$ receptor mRNA and angiotensinogen mRNA in the brain of spontaneously hypertensive rats reduces hypertension of neurogenic origin," *Reg. Pep.*, 49(2):167–174, 1993.

Haaima, Hansen, Christensen, Daho, Nielsen, "Increased DNA binding and sequence discrimination of PNA oligomers containing 2,6-diaminopurine," *Nucl. Acids Res.*, 25(22):4639–4643, 1997.

Hacia et al., "Detection of heterozygous mutations in BRCA1 using high density oligonucleotide arrays and two-colour fluorescence analysis," *Na. Genet.*, 14(4):441–7, 1996.

Hagopian, Mills, Khokhar, Bast, Siddik, "Studies of cisplatin (CDDP) resistance with 1R,2R-diaminocyclohexane (DACH)-diacetato-dichloro-Pt (IV) (acetato-Pt) in ovarian cancer cell lines," *Proc. Amer. Assoc. Cancer Res.*, 37:402(A#1399), 1996.

Halaban, Pomerantz, Marshall, Lambert, Lerner, "Regulation of tyrosinase in human melanocytes grown in culture," *J. Cell Biol.*, 97(2):480–488, 1983.

Hammerschmidt, Brook, McMahon, "The world according to hedgehog," *Trends Genet.*, 13(1):14–21, 1997.

Hampel and Tritz, "RNA catalytic properties of the minimum (-)s TRSV sequence," *Biochem.*, 28:4929, 1989.

Hampel, Tritz, Hicks, Cruz, "'Hairpin' catalytic RNA model: evidence for helices and sequence requirement for substrate RNA," *Nucl. Acids Res.*, 18:299, 1990.

Handel, "Genetic Control of Spermatogenesis in Mice," In: *Spermatogenesis Genetic Aspects*, W. Henning, ed., Springer-Verlag: Berlin, p. 1–52, 1987.

Handel, In: *Spermatogenesis Genetic Aspects*, Vol 15, Henning, W. (Ed.), Springer-Verlag, Berlin, pp 1–52, 1987.

Hanvey, Peffer, Bisi, Thomson, Cadilla, Josey; Ricca, Hassman, Bonham, Au, et al., "Antisense and antigene properties of peptide nucleic acids," *Science*, 258 (5087):1481–1485, 1992.

Harland and Weintraub, "Translation of mammalian mRNA injected into Xenopus oocytes is specifically inhibited by antisense RNA," *J. Cell Biol.*, 101:1094–1099, 1985.

Harlow and Lane, "Antibodies: A Laboratory Manual;" Cold Spring Harbor Laboratory, Cold Spring Harbor, N.Y., 1988.

Harrington and Fleming, "Counting Processes and Survival Analysis," John Wiley and Sons, New York, 1991.

Hasegawa et al., "Radiation-induced cell death in the mouse testis": relationship to apoptbsis," *Radiat. Res.*, 147(4):457–67, 1997.

Haskell and Bowen, "Efficient production of transgenic cattle by retroviral infection of early embryos," *Mol. Reprod. Dev.*, 40(3):386–390, 1995.

Hata, Kaibuchi, Kawamura, Hiroyoshi, Shirataki, Takai, "Enhancement of the actions of smg p21 GDP/GTP exchange protein by the protein kinase A-catalyzed phosphorylation of smg p21, " *J. Biol. Chem.*, 166:6571–6577, 1991.

Havrilesky, Hurteau, Whitaker, Elbendary, Wu, Rodriguez, Bast, Berchuck, "Regulation of apoptosis in normal and malignant ovarian epithelial cells by transforming growth factor-β" *Cancer Res.*, 55:944–948, 1995.

Hawley and Friend, "Strange bedfellows in even stranger places: the role of ATM in meiotic cells, lymphocytes, tumors, and its functional links to p53, " *Genes Dev.*, 10(19):2383–8, 1996.

He and Ingles, "Isolation of human complexes proficient in nucleotide excision repair," *Nucl. Acids Res.*, 25(6):1136–1141, 1997.

Hearing and Tsukamoto, "Enzymatic control of pigmentation in mammals," *Faseb J.*, 5(14):2902–9, 1991.

Heath and Martin, "The development and application of protein-liposome conjugation techniques," *Chem. Phys. Lipids*, 40:347–358, 1986.

Heath et al., "Liposome-mediated delivery of pteridine antifolates to cells: in vitro potency of methotrexate and its alpha and gamma substituents," *Biochim. Biophys. Acta*, 862:72–80, 1986.

Henikoff and Henikoff, "Automated assembly of protein blocks for database searching," *Nucl. Acids Res.*, 19(23):6565–6572, 1991.

Henry-Michelland et al., "Attachment of antibiotics to nanoparticles; Preparation, drug-release and antimicrobial activity in vitro," *Int. J. Pharm.*, 35:121–127, 1987.

Herman, Jen, Merlo, Baylin, "Hypermethylation-associated inactivation indicates a tumor suppressor role for p15INK4B," *Cancer Res.*, 56(4):722–727, 1996.

Herman, Latif, Weng, Lerman, Zbar, Liu, Samid, Duan, Gnarra, Linehan et al., "Silencing of the VHL tumor-suppressor gene by DNA methylation in renal carcinoma," *Proc. Natl. Acad. Sci. USA*, 91(21):9700–9704, 1994.

Hermonat and Muzycska, "Use of adenoassociated virus as a mammalian DNA cloning vector: Transduction of neomycin resistance into mammalian tissue culture cells," *Proc. Natl. Acad. Sci. USA*, 81:6466–6470, 1984.

Hersdorffer et al., "Efficient gene transfer in live mice using a unique retroviral packaging line," *DNA Cell Biol.*, 9:713–723, 1990.

Hertel, Pardi, Uhlenbeck, Koizumi, Ohtsuka, Uesugi, Cedergren, Eckstein, Gerlach, Hodgson et al., "Numbering system for the hammerhead," Nucl. Acids Res., 20(12):3252, 1992.

Herz and Gerard, "Adenovirus-mediated transfer of low density lipoprotein receptor gene acutely accelerates cholesterol clearance in normal mice," *Proc. Natl. Acad Sci. USA*, 90:2812–2816, 1993.

Hilsenbeck. and Clark, "Practical p-Value Adjustment for Optimally Selected Cutpoints," *Statistics in Medicine*, 15:103–112, 1996.

Hockenbery et al., "Bcl-2 functions in an antioxidant pathway to prevent apoptosis," *Cell*, 75(2):241–51, 1993.

Hogan, Beddington, Constantini, Lacy, In: *Manipulating the Mouse Embryo: A Laboratory Manual*, Cold Spring Harbor Laboratory Press, Plainview, N.Y., 1994.

Hoggard, Brintnell, Howell, Weissenbach, Varley, "Allelic imbalance on chromosome 1 in human breast cancer. II. Microsatellite repeat analysis," *Genes, Chromosomes Cancer*, 12:24–31, 1995.

Hoover et al., (Eds.), "Remington's Pharmaceutical Sciences," 15th Edition, Mack Publishing Co., Easton, Pa., 1975.

Horwich et al., "Synthesis of hepadnavirus particles that contain replication-defective duck hepatitis B virus genomes in cultured HuH7 cells," *J. Virol.*, 64:642–650, 1990.

Hummel, *Mouse News Letter*, 34:31, 1966.

Hurteau, Rodriguez, Whitaker, Shah, Mills, Bast, Berchuck, "Transforming growth factor-β inhibits proliferation of human ovarian cancer cells obtained from ascites," *Cancer*, 74:93–99, 1994.

Hwang, Park, Park, "Gastric retentive drug-delivery systems," *Crit. Rev. Ther. Drug Carrier Syst.*, 15(3):243–284, 1998.

Hyrup and Nielsen, "Peptide nucleic acids (PNA): synthesis, properties and potential applications," *Bioorg. Med. Chem.*, 4(1):5–23, 1996.

Imaizumi et al., "Liposome-entrapped superoxide dismutase ameliorates infarct volume in focal cerebral ischemia," *Acta. Neurochirurgica Suppl.*, 51:236–238, 1990b.

Imaizumi et al., "Liposome-entrapped superoxide dismutase reduces cerebral infarction in cerebral ischemia in rats," *Stroke*, 21(9):1312–1317, 1990a.

Inada, Y., Ojima, M., Itoh, K., Shino, A., Nishikawa, K. Effects of delapril on stroke, kidney dysfunction and cardiac hypertrophy in stroke-prone spontaneously hypertensive rats. *Drugs Exp. Clin. Res.* 21(2):41–49, 1995.

Innis et al., "DNA sequencing with Thermus aquaticus DNA polymerase and direct sequencing of polymerase chain reaction-amplified DNA," *Proc. Natl. Acad. Sci. USA*, 85(24):9436–9440, 1988.

Ito et al., "Apoptosis-like cell death in experimentally-induced cryptorchidism in adult mice," *J. Vet. Med. Sci.*, 59(5):353–9, 1997.

Iyer et al., "Interactions involving the human RNA polymerase II transcription/nucleotide excision repair complex TFIIH, the nucleotide excision repair protein XPG, and Cockayne syndrome group B (CSB) protein," Biochemistry, 35(7):2157–67, 1996.

Jacobs, Kohler, Wiseman, Marks, Whitaker, Kerns, Humphrey, Berchuck, Ponder, Bast, "Clonal origin of epithelial ovarian cancer: Analysis by loss of heterozygosity, p53 mutation and X chromosome inactivation," *J. Natl. Cancer Inst.*, 84:1793–1798, 1992.

Jacobs, Smith, Wiseman, Futreal, Harrington, Osborne, Leach, Molyneaux, Berchuck, Ponder, Bast, "A deletion. unit on chromosome 17q in epithelial ovarian tumors distal to the familial breast/ovarian cancer locus," *Cancer Res.*, 53:1218–1221, 1993.

Jaeger, Turner, Zuker, "Improved predictions of secondary structures for RNA," *Proc. Natl. Acad. Sci. USA*, 86(20):7706–7710, 1989.

Jahnke, Van de Stolpe, Caldenhoven, Johnson, "Constitutive expression of human intercellular adhesion molecule-1 (ICAM-1) is regulated by differentially active enhancing and silencing elements, *Eur. J. Biochem*, 228(2):439–446, 1995.

Jameson and Wolf, "The antigenic index: a novel algorithm for predicting antigenic determinants," *Compu. Appl. Biosci.*, 4(1):181–186, 1988.

Jaskulski, deRiel, Mercer, Calabretta, Baserga, "Inhibition of cellular proliferation by antisense oligodeoxynucleotides to PCNA cyclin," *Science*, 240(4858):1544–1546, 1988.

Jelinek and Hassell, "Reversion of middle T antigen-transformed Rat-2 cells by Krev-1: implications for the role of p21 c-Ras in polyomavirus-mediated transformation," *Oncogene*, 7:1687–1698, 1992.

Jensen and Pedersen, "Nocturnal blood pressure and relation to vasoactive hormones and renal function in hypertension and chronic renal failure," *Blood Press.*, 6(6):332–342, 1997.

Jimenez, Tsukamoto, Hearing, "Tyrosinases from two different loci are expressed by normal and by transformed melanocytes," *J. Biol. Chem.*, 266(2):1147–1156, 1991.

Johnson et al., "Germ cell degeneration during post-prophase of meiosis and serum concentrations of gonadotropins in young adult and older adult men," *Biol. Reprod.*, 31(4):779–84, 1984.

Johnson et al., "Quantification of human spermatogenesis: germ cell degeneration during spermatocytogenesis and meiosis in testes from younger and older adult men," *Biol. Reprod.*, 37(3):739–47, 1987.

Jones and Shenk, "Isolation of deletion and substitution mutants of adenovirus type 5," *Cell*, 13:181–188, 1978.

Joyce, "RNA evolution and the origins of life," *Nature*, 338:217–244, 1989.

Justice, Jenkins, Copeland, "Recombinant inbred mouse strains: models for disease study," *Trends Biotechnol.*, 10(4): 120–6, 1992.

Kacinski, "CSF-1 and its receptor in ovarian, endometrial and breast cancer," *Ann. Med*, 27(1):79–85, 1995.

Kacinski, Mayer, King et al., "Neu protein overexpression in benign, borderline, and malignant ovarian neoplasms," *Gynecol. Oncol.*, 44:245–253, 1992.

Kaneda et al., "Increased expression of DNA cointroduced with nuclear protein in adult rat liver," *Science*, 243:375–378, 1989.

Kaneda, Iwai, Uchida, "Introduction and expression of the human insulin gene in adult rat liver," *J. Biol. Chem.*, 264(21):12126–12129, 1989.

Kang, Cho, Kole, "Up-regulation of luciferase gene expression with antisense oligonucleotides: implications and applications in ftimctional assay development," *Biochemistry*, 37(18):6235–6239, 1998.

Karlan, Baldwin, Cirisano, Mamula, Jones, Lagasse, "Secreted ovarian stromal substance inhibits ovarian epithelial cell proliferation," *Gyn. Onc*, 59(1):67–74, 1995.

Karlsson, Van Doren, Schweiger, Nienhuis, Gluzman, "Stable gene transfer and tissue-specific expression of a human globin gene using adenoviral vectors," *EMBO J.*, 5(9):2377–2385, 1986.

Kashani-Saber et al., *Antisense Res. Dev.*, 2:3–15, 1992.

Kato et al., "Expression of hepatitis B virus surface antigen in adult rat liver," *J. Biol. Chem.*, 266:3361–3364, 1991.

Keegan, Holtzman, Plug, Christenson, Brainerd, Flaggs, Bentley, Taylor, Meyn, Moss, Carr, Ashley, Hoekstra, "The Atr and Atm protein kinases associate with different sites along meiotically pairing chromosomes," *Genes Dev.*, 10(19):2423–2437, 1996.

Kettel, Murphy, Morales, Ulmann, Baulieu, Yen, "Treatment of endometriosis with the antiprogesterone mifepristone," *Fertil. Steril.*; 65(1):23–28, 1996.

Kitayama, Sugimoto, Matsuzaki, Ikawa, Noda, "A Ras-related gene with transformation suppressor activity," *Cell*, 56:77–84, 1989.

Kleckner, "Meiosis: how could it work?" *Proc. Natl. Acad. Sci. USA*, 93(16):8167–74, 1996.

Kleene, "Patterns of translational regulation in the mammalian testis," *Mol. Reprod. Dev.*, 43(2):268–81, 1996.

Klein et al., *Proc. Natl. Acad. Sci. USA* , 85:8502–8505, 1988.

Klein, Wolf, Wu, Sanford, "High-velocity microprojectiles for delivering nucleic acids into living cells," *Nature*, 327:70–73, 1987.

Knudson et al., "Bax-deficient mice with lymphoid hyperplasia and male germ cell death," *Science*, 270(5233):96–9, 1995.

Kohler and Milstein, "Continuous cultures of fused cells secreting antibody of predefined specificity," *Nature*, 256(5517):495–497, 1975.

Kohler and Milstein, "Derivation of specific antibody-producing tissue culture and tumor lines by cell fusion," *Eur. J. Immunol.*, 6(7):511–519, 1976.

Kohler, Marks, Wiseman, Jacobs, Davidoff, Clarke-Pearson, Soper, Bast, Berchuck, "Spectrum of mutation and frequency of allelic deletion of the p53 gene in ovarian cancer," *J. Natl. Cancer Inst.*, 85:1513–1519, 1993.

Koike, Krieger, Jacob, Mukoyama, Pratt, Dzau, "Angiotensin converting enzyme and genetic hypertension: cloning of rat cDNAs and characterization of the enzyme," *Biochem. Biophys. Res. Commun.*, 198(1):380–386, 1994.

Kolodner, "Mismatch repair: mechanisms and relationship to cancer susceptibility," *Trends in Biochemical Sciences*, 20(1 0):397–401, 1995.

Koopman et al., "Zfy gene expression patterns are not compatible with a primary role in mouse sex determination," *Nature*, 342(6252):940–2, 1989.

Koppelhus, Zachar, Nielsen, Liu, Eugen-Olsen, Ebbesen, "Efficient in vitro inhibition of HIV-1 gag reverse transcription by peptide nucleic acid (PNA) at minimal ratios of PNA/RNA," *Nucl. Acids Res.*, 25(11):2167–2173, 1997.

Korn and Simon, "Measures of explained variation for survival data," *Statistics in Medicine*, 9:487–503, 1990.

Kornblau, Thall, Yang, Estey, Andreeff, "Analysis of CD7 Expression in acute myelogenous leukemia: Martingale residual plots combined with 'optimal' cutpoint analysis reveals absence of prognostic significance," *Leukemia*, 9:1735–1741, 1995.

Kremsky, Wooters, Dougherty, Meyers, Collins, Brown, "Immobilization of DNA via oligonucleotides containing an aldehyde or carboxylic acid group at the 5' terminus," *Nucl. Acids Res.*, 15(7):2891–2909, 1987.

Kroning, Jones, Hom, Chuang, Sanga, Los, Howell, Christen, "Enhancement of drug sensitivity of human malignancies by epidermal growth factor," *Brit. J. Cancer*, 72(3):615–619, 1995.

Kruk, Maines-Bandiera, Auersperg, "A simplified method to culture human ovarian surface epithelium," *Lab. Invest.*, 63(1):132–136, 1990.

Kuby, Fleming, Alber, Richardson, Takenaka, Hamada, "Studies on yeast nucleoside triphosphate-nucleoside diphosphate transphosphorylase (nucleoside diphosphokinase). IV. Steady-state kinetic properties with thymidine nucleotides (including 3'-azido-3'-deoxythymidine analogues)," *Enzyme*, 45(1–2):1–13, 1991.

Kuby, In: *Immunology*, 2nd Edition, W.H. Freeman & Company, New York, 1994.

Kunkel, Roberts, Zakour, "Rapid and efficient site-specific mutagenesis without phenotypic selection," *Methods Enzymol.*, 154:367–382, 1987.

Kuro-o, Matsumura, Aizawa, Kawaguchi, Suga, Utsugi, Ohyama, Kurabayashi, Kaname, Kume, Iwasaki, Iida, Shiraki-Iida, Nishikawa, Nagai, Nabeshima, "Mutation of the mouse klotho gene leads to a syndrome resembling ageing," *Nature*, 390(6655):45–51, 1997.

Kwoh, Davis, Whitfield, Chappelle, DiMichele, Gingeras, "Transcription-based amplification system and detection of amplified human immunodeficiency virus type 1 with a bead-based sandwich hybridization format," *Proc. Natl. Acad. Sci. USA*, 86(4):1173–1177, 1989.

Kwon et al., "Isolation, chromosomal mapping, and expression of the mouse tyrosinase gene," *J. Invest. Dermatol.*, 93(5):589–94, 1989.

Kyte and Doolittle, "A simple method for displaying the hydropathic character of a protein," *J. Mol. Biol.*, 157(1):105–132, 1982.

L'Huillier, David, Bellamy, "Cytoplasmic delivery of ribozymes leads to efficient reduction in alpha-lactalbumin mRNA levels in C127I mouse cells," *EMBO J.*, 11(12):4411–4418, 1992.

Lahn and Page, "Functional coherence of the human Y chromosome," *Science*, 278(5338):675–680, 1997.

Landschulz, Johnson, McKnight, "The leucine zipper: a hypothetical structure. common to a new class of DNA binding proteins," *Science*, 240(4860):1759–1764, 1988.

Lansdorp, Verwoerd, van de Rijke, Dragowska, Little, Dirks, Raap, Tanke,. "Heterogeneity in telomere length of human chromosomes," *Hum. Mol. Genet.*, 5(5):585–591, 1996.

Larsen and Nielsen, "Transcription-mediated binding of peptide nucleic acid (PNA) to double-stranded DNA: sequence-specific suicide transcription," *Nucl. Acids Res.*, 24(3):458–463, 1996.

Lasic, "Novel applications of liposomes," *Trends Biotechnol.*, 16(7):307–321, 1998.

Lawrence, Altschul, Boguski, Liu, Neuwald, Wootton, *Science*, 262(5131):208–214, 1993.

Le Gal La Salle, Robert, Berrard, Ridoux, Stratford-Perricaudet, Perricaudet, Mallet, "An adenovirus vector for gene transfer into neurons and glia in the brain," *Science*, 259:988–990, 1993.

Leahy et al., "Structure of a fibronectin type III domain from tenascin phased by MAD analysis of the selenomethionyl protein," *Science*, 258(5084):987–91, 1992.

Lee et al., "Human retinoblastoma susceptibility gene: cloning, identification, and sequence," *Science*, 235:1394–1399, 1987.

Lee, Wang, Smeda, "Effects of perindopril on hypertension and stroke prevention in experimental animals," *Can. J. Cardiol.* 10 (Suppl D):33D–36D, 1994.

Levrero, Barban, Manteca, Ballay, Balsamo, Avantaggiati, Natoli, Skellekens, Tiollais, Perricaudet, "Defective and nondefective adenovirus vectors for expressing foreign genes in vitro and in vivo," *Gene*, 101: 195–202, 1991.

Lewis, "A consideration of the advantages and potential difficulties of the use of transgenic mice for the study of germinal mutations," *Mutation Research*, 307(2):509–15, 1994.

Li, Han, Resnik, Carcangiu, Schwartz, Yang-Feng, "Advanced ovarian carcinoma: molecular evidence of unifocal origin," *Gyn. Onc.*, 51(1):21–5, 1993.

Liang and Pardee, "Differential display of eukaryotic messenger RNA by means of the polymerase chain reaction," *Science*, 257:967–971, 1992.

Lidor, Shpall, Peters, Bast, "Synergistic cytotoxicity of different alkylating agents for epithelial ovarian cancer," *Int. J. Cancer*, 49(5):704–710, 1991.

Lidor, Xu, Martinez-Maza, Olt, Marks, Berchuck, Ramakrishnan, Berek, Bast, "Constitutive production of macrophage colony stimulating factor and interleukin-6 by human ovarian surface epithelial cells," *Exp. Cell Res.*, 207:332–339, 1993.

Lieber, Sandig, Sommer, Bahring, Strauss, "Stable high-level gene expression in manunalian cells by T7 phage RNA polymerase," *Methods Enzymol.*, 217:47–66, 1993.

Lin et al., "Coordinate developmental control of the meiotic cell cycle and spermatid differentiation in Drosophila males," *Development*, 122(4):1331–41, 1996.

Lin, "Goodness-of-fit analysis for the Cox regression model based on a class of parameter estimators," *J. American Statistical Association*, 86:725–728, 1991.

Lindsley and Tokuyasu, "Spermatogenesis," In: *The Genetics and Development of Drosophila*, M. Ashburner and T. R. F. Wright, eds.; Academic Press: London. p. 25–294, 1980.

Linz, Jessen, Becker, Scholkens, Wiemer, "Long-term ACE inhibition doubles lifespan of hypertensive rats," *Circulation* 96(9):3164–3172,1997.

Lisziewicz et al., *Proc. Natl. Acad. Sci. USA*, 90:8000–8004, 1993.

Loomis and Iranfar, GenBank Acccession Number AF 019980.

Lopez-Berestein et al., "Liposomal amphotericin B for the treatment of systemic fungal infections in patients with cancer: a preliminary study" *J. Infect. Dis.*, 2151:704, 1985a.

Lopez-Berestein et al., "Protective effect of liposomal-amphotericin B against *C. albicans* infection in mice," *Cancer Drug Delivery*, 2:183, 1985b.

Lounis et al., "Primary cultures of normal and tumoral human ovarian epithelium: a powerful tool for basic molecular studies," *Exp. Cell Res.*, 215:303–309, 1994.

Loupart, Armour, Walker, Adams, Brammar, Varley, "Allelic imbalance on chromosome 1 in human breast cancer. I. Ministellite and RFLP analysis," *Genes Chromosomes Cancer*, 12:16–23, 1995.

Lowe and Temple, "Calcitonin and insulin in isobutylcyanoacrylate nanocapsules: protection against proteases and effect on intestinal absorption in rats," 46(7):547–552, 1994.

Lu, Xiao, Clapp, Li, Broxmeyer, "High efficiency retroviral mediated gene transducion into single isolated immature and replatable CD34(3+) hematopoietic stem/progenitor cells from human umbilical cord blood," *J. Exp. Med.*, 178(6):2089–2096, 1993.

Lynch, Smyrk, Lynch, "Overview of natural history, pathology, molecular genetics and management of HNPCC (Lynch Syndrome)," *Int. J. Cancer*, 69(1):38–43, 1996.

Lyon, "Transmission ratio distortion in mouse t-haplotypes is due to multiple distorter genes acting on a responder locus," *Cell*, 37(2):621–8, 1984.

Macejak and Sarnow, "Internal initiation of translation mediated by the 5' leader of a cellular mRNA," *Nature*, 353:90–94, 1991.

MacGregor et al., "Symplastic spermatids (sys): a recessive insertional mutation in mice causing a defect in spermatogenesis," *Proceedings of the National Academy of Sciences of the United States of America*, 87(13):5016–20, 1990.

Magram and Bishop, "Dominant male sterility in mice caused by insertion of a transgene," *Proceedings of the National Academy of Sciences of the United States of America*, 88(22):10327–31, 1991.

Maines and Wasserman, "Regulation and execution of meiosis in Drosophila males," *Current Topics in Developmental Biology*, 37:301–332, 1998.

Malkin, Li, Strong et al., "Germ line p53 mutations in a familial syndrome of breast cancer, sarcomas, and other neoplasms," *Science*, 250:1233–1238, 1990.

Maloy et al., In: *Microbial Genetics*, 2nd Edition, Jones and Barlett Publishers, Boston, Mass., 1994.

Maltais, Blake, Eppig, Davisson, "Rules and guidelines for mouse gene nomenclature: a condensed version. International Committee on Standardized Genetic Nomenclature for Mice," *Genomics*, 45(2):471–476, 1997.

Maltais, Blake, Eppig, Davisson, "Rules and guidelines for mouse gene nomenclature: a condensed version. International Committee on Standardized Genetic Nomenclature for Mice," *Genomics*, 45(2):471–476, 1997.

Mangues et al., "Tumorigenesis and male sterility in transgenic mice expressing a MMTV/N-ras oncogene," *Oncogene*, 5(10):1491–7, 1990.

Maniatis et al., "Molecular Cloning: a Laboratory Manual," Cold Spring Harbor Laboratory, Cold Spring Harbor, N.Y., 1982.

Mann et al., "Construction of a retrovirus packaging mutant and its use to produce helper-free defective retrovirus," *Cell*, 33:153–159, 1983.

Margalit, "Liposome-mediated drug targeting in topical and regional therapies," *Crit. Rev. Ther. Drug Carrier Syst.*, 12(2–3):233–261, 1995.

Mariani et al., "Expression of biologically active mouse and human CD95/APO-1/Fas ligand in the baculovirus system," *J. Immunol. Methods*, 193(1):63–70, 1996.

Markowitz et al., "A safe packaging line for gene transfer: Separating viral genes on two different plasmids," *J. Virol.*, 62:1120–1124, 1988.

Mathiowitz, Jacob, Jong, Carino, Chickering, Chaturvedi, Santos, Vijayaraghavan, Montgomery, Bassett, Morrell, "Biologically erodable microspheres as potential oral drug delivery systems," *Nature*, 386(6623):410–414, 1997.

Matzuk et al., "Alpha-inhibin is a tumour-suppressor gene with gonadal specificity in mice," *Nature*, 360(6402):313–9, 1992.

McKee, "Meiotic recombination: a mechanism for tracking and eliminating mutations?"*Bioessays*, 18(5):411–9, 1996.

Menefee, Chesson, Wall, "Stress urinary incontinence due to prescription medications: alpha-blockers and angiotensin converting enzyme inhibitors," *Obstet. Gynecol.*, 91(5 Pt 2):853–854, 1998.

Meng, Wielbo, Gyurko, Phillips, "$AT_1$ receptor mRNA antisense oligonucleotide inhibits central angiotensin induced thirst and vasopressin," *Reg. Pep.*, 54:543–551, 1994.

Merrifield B., "Solid phase synthesis," *Science*, 232 (4748):341–347, 1986.

Michael, *Biotechniques*, 16:410–412, 1994.

Michel and Westhof, "Modeling of the three-dimensional architecture of group I catalytic introns based on comparative sequence analysis," *J. Mol. Biol.*, 216:585–610, 1990.

Michieli et al., "Induction of WAF1/CIP1 by a p53-independent pathway," *Cancer Res.*, 54:3391–3395, 1994.

Miki, Swensen, Shattuck-Eidens et al., "A strong candidate for the breast and ovarian cancer susceptibility gene BRCA1," *Science*, 266:66–71, 1994.

Mintz and Russell, "Gene-induced embryological modifications of primordial germ cells," *J. Exp. Zool.*, 134:207–237, 1957.

Mintz, "Embryological development of primordial germ cells in the mouse: Influence of a new mutation," *W. Exp. Morphol.*, 5:396–403, 1957a.

Miura, Kaibuchi, Itoh, Corbin, Francis, Takai, "Phosphorylation of smg p21B/Rap1B p21 by cyclic GMP-dependent protein kinase," FEB. Lett., 297:171–174, 1992.

Modrich and Lahue, "Mismatch repair in replication fidelity, genetic recombination, and cancer biology," Annu. Rev. Biochem., 65:101–133, 1996.

Mok, Tsao, Knapp, Fishbaugh, Lau, "Unifocal origin of advanced human epithelial ovarian cancers," Cancer Res., 52:5119–5122, 1992.

Mollegaard, Buchardt, Egholm, Nielsen, "Peptide nucleic acid.DNA strand displacement loops as artificial transcription promoters," Proc. Natl. Acad. Sci. USA; 91(9):3892–3895, 1994.

Moosmayer et al., "Coexpression of the human TNF receptors TR60 and TR80 in insect cells: analysis of receptor complex formation," Lymphokine Cytokine Res, 13(5):295–301, 1994.

Mori and Fukatsu, "Anticonvulsant effect of DN-1417 a derivative of thyrotropin-releasing hormone and liposome-entrapped DN-1417 on amygdaloid-kindled rats," Epilepsia, 33(6):994–1000, 1992.

Mori, Nakamura, Kimura, Irie, Takigawa, Shiota, "Programmed cell death in the interdigital tissue of the fetal mouse limb is apoptosis with DNA fragmentation," Anat. Rec., 242(1), 103–110, 1995.

Morishige, Kurachi, Amemiya, Adachi, Inoue, Miyake, Tanizawa, Sakoyama, "Involvement of transforming growth factor alpha/epidermal growth factor receptor autocrine growth mechanism in an ovarian cancer cell line in vitro," Cancer Res., 51(21):5951–5955, 1991.

Morris et al., "A new peptide vector for effcient delivery of oligonucleotides into mamalain cell," Nucleic Acids Res., 25(14):2730–2736, 1997

Moser, "Why are physicians not prescribing diuretics more frequently in the management of hypertension?," JAMA, 279(22):1813–1816, 1998.

Moser, Young, Rodriguez, Pizzo, Bast, Stack, "Secretion of extracellular matrix-degrading proteinases is increased in epithelial ovarian carcinomas," Int J. Cancer, 56:552–559, 1994.

Mujoo, Maneval, Anderson, Gutterman, "Adenoviral-mediated p53 tumor suppressor gene therapy of human ovarian carcinoma," Oncogene, 12(8): 1617–1623, 1996.

Mullen, Eicher, Sidman, "Purkinje cell degeneration, a new neurological mutation in the mouse," Proc. Natl. Acad. Sci. USA, 73(1):208–12, 1976.

Muller et al., "Efficient transfection and expression of heterologous genes in PC12 cells," Cell, Biol., 9(3):221–229, 1990.

Mulligan, "The Basic Science of Gene Therapy," Science, 260:926–932, 1993.

Muzyczka and McLaughlin, "Use of adeno-associated virus as a mamalian transduction vector," In: Current Communications in Molecular Biology: Viral Vectors, Glzman and Hughes, eds., Cold Spring Harbor Laboratory Press, Cold Spring Harbor, N.Y., 1988:39–44.

Muzyczka, "Use of adeno-associated virus as a general transduction vector for mammalian cells," In: Current Topics in Microbiology and Immunology, Springer-Verlag, Berlin, 158:97–129, 1992.

Nagai, Negrini, Carter, Gillum, Rosenberg, Schwartz, Croce, "Detection and cloning of a common region of loss of heterozygosity at chromosome 1p in breast cancer," Cancer Res., 55:1752–1757, 1995.

Nagase, Seki, Tanaka, Ishikawa, Nomura, "Predication of the coding sequences of unidentified human genes. IV. The coding sequences of 40 new genes (KIAA0121–KIAA0160) deduced by analysis of cDNA clones from human cell line KG-1," DNA Res., 2(4):167–174, 1995.

Nakai and Kanehisa, "A knowledge base for predicting protein localization sites in eukaryotic cells," Genomics, 14(4):897–911, 1992.

Nantel, Monaco, Foulkes, Masquilier, LeMeur, Henriksen, Dierich, Parvinen, Sassone-Corsi, "Spermiogenesis deficiency and germ-cell apoptosis in CREM-mutant mice," Nature, 380(6570):159–162, 1996.

Needleman and Wunsch, J. Mol. Biol., 48:443, 1970, as revised by Smiih and Waterman, Adv. Appl. Math. 2:482, 1981.

Neels et al., "Sensitive colorimetric assay for angiotensin converting enzyme. in serum," Clin. Chem., 29(7):1399–1403, 1983.

Nerurkar, Rose, Stobaugh, Borchardt, "Selective fluorogenic derivatization of a peptide nucleic acid trimer with naphthalene-2,3-dicarboxaldehyde," J. Pharm. Biomed. Anal., 15(7):945–950, 1997.

Nguyen et al., "Targeting of Bcl-2 to the mitochondrial outer membrane by a COOH-terminal signal anchor sequence," J. Biol. Chem., 268(34):25265–8, 1993.

Nicholls, Richards, Agarwal, "The importance of the renin-angiotensin system in cardiovascular disease," J. Hum. Hypertens, 12(5):295–299, 1998.

Nicolas and Rubenstein, "Retroviral vectors," In: Vectors: A survey of molecular cloning vectors and their uses, Rodriguez R L, Denhardt D T, ed., Stoneham: Butterworth, pp. 493–513, 1988.

Nicolau and Gersonde, "Incorporation of inositol hexaphosphate into intact red blood cells,. I. fusion of effector-containing lipid vesicles with erythrocytes," Naturwissenschaften (Germany), 66(11):563–566, 1979.

Nicolau and Sene, "Liposome-mediated DNA transfer in eukaryotic cells," Biochim. Biophys. Acta, 721:185–190, 1982.

Nicolau et al., "Liposomes as carriers for in vivo gene transfer and expression," Methods Enzymol., 149:157–176, 1987.

Nielsen, DiGiovanni, Christensen, Knepper, Harris, "Cellular and subcellular immunolocalization of vasopressin-regulated water channel in rat kidney," Proc. Natl. Acad. Sci. USA, 90(24):11663–11667, 1993.

Nielsen, Egholm, Berg, Buchardt, "Sequence-selective recognition of DNA by strand displacement with a thymine-substituted polyamide," Science, 254(5037):1497–1500, 1991.

Nisson, Watkins, Krizman, In: Current protocols in human genetics, N. Dracopoli et al., (eds.), John Wiley & Sons, Inc., 1:6.1.1–6.1.27, 1994.

Niwa, Yamamura, Miyazaki, "Efficient selection for high-expression transfectants with a novel eukaryotic vector," Gene, 108(2):193–9, 1991.

Nocentini et al., "DNA damage recognition by XPA protein promotes efficient recruitment of transcription factor II H," J. Biol. Chem., 272(37):22991–4, 1997.

Norton, Piatyszek, Wright, Shay, Corey,"Inhibition of human telomerase activity by peptide nucleic acids," *Nat. Biotechnol.*, 14(5):615–619, 1996.

Norton, Waggenspack, Varnum, Corey, "Targeting peptide nucleic acid-protein conjugates to structural features within duplex DNA," *Bioorg. Med. Chem.*, 3(4):437–445, 1995.

O'Brien, "Mammalian genome mapping: lessons and prospects," *Curr. Opin. Genet. Dev.*, 1(1):105–11, 1991.

Oakberg, "A description of spermiogenesis in the mouse and its use in analysis of the cycle of the seminiferous germ cell renewal," *Am. J. Anat.*, 99:391–413, 1956.

Odorisio, Rodriguez, Evans, Clarke, Burgoyne, "The meiotic checkpoint monitoring synapsis eliminates spermatocytes via p53-independent apoptosis," *Nat. Genet.*, 18(3):257–261, 1998.

Ohara, Dorit, Gilbert, "Direct genomic sequencing of bacterial DNA: the pyruvate kinase I gene of *Escherichia coli,*" *Proc. Natl. Acad. Sci. USA*, 86(18):6883–6887, 1989.

Ohara, Dort, Gilbert, "One-sided polymerase chain reaction: the amplification of cDNA," *Proc. Natl. Acad Sci. USA*, 86(15):5673–5677, 1989.

Ohishi et al., "Structure and chromosomal localization of the GPI-anchor synthesis gene PIGF and its pseudogene psi PIGF," *Genomics*, 29(3):804–7, 1995.

Ohkawa, Yuyama, Taira, "Activities of HIV-RNA targeted ribozymes transcribed from a 'shot-gun' type ribozyme-trimming plasmid," *Nucl. Acids Symp. Ser.*, 27:15–6, 1992.

Ohtani-Fujita, ujita, Aoike, Osifchin, Robbins, Sakai, "CpG methylation inactivates the promoter activity of the human retinoblastoma tumor-suppressor gene," Oncogene, 8(4):1063–1067, 1993

Ojwang, Hampel, Looney, Wong-Staal, Rappaport, "Inhibition of human immunodeficiency virus type 1 expression by a hairpin ribozyme," *Proc. Natl. Acad. Sci. USA.*, 89(22):10802–10806, 1992.

Okabe, Ikawa, Ashkenas, "Male infertility and the genetics of spermatogenesis," *Am. J. Hum. Genet.*, 62(6):1274–1281, 1998.

Ono, Hirose, Miyazaki, Yamamoto, Matsumoto, "Transgenic medaka fish bearing the mouse tyrosinase gene: expression and transmission of the transgene following electroporation of the orange-colored variant," *Pigment Cell Res.*, 10(3): 168–175, 1997.

Orum, Nielsen, Egholm, Berg, Buchardt, Stanley, "Single base pair mutation analysis by PNA directed PCR™ clamping," *Nucl. Acids Res.*, 21(23):5332–5336, 1993.

Orum, Nielsen, Jorgensen, Larrson, Stanley, Koch, "Sequence-specific purification of nucleic acids by PNA-controlled hybrid selection," *Biotechniques*, 19(3):472–480, 1995.

Oster-Granite et al., "Age-dependent neuronal and synaptic degeneration in mice transgenic for the C terminus of the amyloid precursor protein," *J. Neurosci.*, 16(21):6732–41, 1996.

Pardridge, Boado, Kang, "Vector-mediated delivery of a polyamide ("peptide") nucleic acid analogue through the blood-brain barrier in vivo," *Proc. Natl. Acad. Sci. USA*, 92(12):5592–5596, 1995.

Paskind et al., "Dependence of moloney murine leukemia virus production on cell growth," *Virology*, 67:242–248, 1975.

Patton, Jameson, Martin, Altschuler, Bast, Ostrowski, "Activated ras signaling and uPA expression in ovarian carcinoma," Fifth Meeting on the Molecular Basis of Cancer, Hood College, Frederick, Md., 1994.

Pease et al., Light-generated oligonucleotide arrays for rapid DNA sequence analysis," *Proc. Natl. Acad. Sci. USA*, 91(11):5022–5026, 1994.

Pellas, Ramachandran, Duncan, Pan, Marone, Chada, "Germ-cell deficient(gcd), an insertional mutation manifested as infertility in transgenic mice," *Proc. Natl. Acad. Sci. USA*, 88(19):8787–8791, 1991.

Pelletier and Sonenberg, "Internal initiation of translation of eukaryotic mRNA directed by a sequence derived from poliovirus RNA," *Nature*, 334(6180):320–325, 1988.

Perales, Ferkol, Beegen, Ratnoff, Hanson, "Gene transfer in vivo: sustained expression and regulation of genes introduced into the liver by receptor-targeted uptake," *Proc. Natl. Acad. USA*, 91(9):4086–4090, 1994.

Peris, Jung, Resnick, Walker, Malakhova, Bokrand, Wielbo, "Antisense inhibition of striatal GABAA receptor proteins decreases GABA-stimulated chloride uptake and increases cocaine sensitivity in rats," *Mol. Brain Res.*, 57:310–312, 1998.

Perreault, Wu, Cousinequ, Ogilvie, Cedergren, "Mixed deoxyribo- and ribo-oligonucleotides with catalytic activity," *Nature*, 344(6266):565, 1990.

Perrotta and Been, "Cleavage of oligoribonucleotides by a ribozyme derived from the hepatitis delta virus RNA sequence," *Biochem.*, 31(1):16, 1992.

Perry-O'Keefe, Yao, Coull, Fuchs, Egholm, "Peptide nucleic acid pre-gel hybridization: an alternative to southern hybridization," *Proc. Natl. Acad. Sci. USA*, 93(25):14670–14675, 1996.

Phillips and Gyurko, "Antisense oligonucleotides: New tools for physiology," *News Physiol. Sci.*, 12:99–105, 1997.

Phillips, "Antisense inhibition and adeno-associated viral vector delivery for reducing hypertension," *Hypertension*, 29(2):177–187, 1997.

Phillips, Wielbo, Gyurko, "Anitsense inhibiiton of hypertension: a new strategy for renin-angiotensin candidate genes," *Kidney International*, 46:1554–1556, 1994.

Pieken, Olsen, Benseler, Aurup, Eckstein, "Kinetic characterization of ribonuclease-resistant 2'-modified hammerhead ribozymes," *Science*, 253(5017):314, 1991.

Pignon et al., "Exhaustive analysis of the P53 gene coding sequence by denaturing gradient gel electrophoresis: application to the detection of point mutations in acute leukemias," *Hum. Mutat.*, 3(2):126–132, 1994.

Pikul et al., "In vitro killing of melanoma by liposome-delivered intracellular irradiation, *Arch. Surg.*, 122(12):1417–1420, 1987.

Pinto-Alphandary, Balland, Couvreur, "A new method to isolate polyalkylcyanoacrylate nanoparticle preparations," *J. Drug Target*, 3(2):167–169, 1995.

Pinto-Sietsma and Paul, "Transgenic rats as models for hypertension," *J. Hum. Hypertens.*, 11(9):577–581, 1997.

Pizon, Chardin, Lerosey, Olofsson, Tavitian, "Human cDNAs Rap1 and Rap2 homologous to the Drosophila gene DRas3 encode proteins closely related to Ras in the 'effector' region," *Oncogene*, 3:210–204, 1988.

Potter et al., "Enhancer-dependent expression of human k immunoglobulin genes introduced into mouse pre-B lymphocytes by electroporation," *Proc. Nat. Acad. Sci. USA*, 81:7161–7165, 1984.

Powell, Clozel, Muller, Kuhn, Hefti, Hosang, Baumgartner, "Inhibitors of angiotensin converting-enzyme prevent myointimal proliferation after vascular injury," *Science*, 245:186–188, 1989.

Pregibon, "Resistant fits for some commonly used logistic models with medical applications," *Biometrics*, 38:485–498, 1982.

Prokop and Bajpai, "Recombinant DNA Technology I," Conference on Progress in Recombinant DNA Technology Applications, Potosi, M I, Jun. 3–8, 1990, *Ann. N.Y. Acad. Sci.*, 646:1–383, 1991.

Quilliam, Mueller, Bohl, Prossnitz, Sklar, Der, Bokoch, "Rap1A is a substrate for cyclic AMP-dependent protein kinase in human neutrophils," *J. Immunol.*, 147:1628–1635, 1991.

Quintanar-Guerrero, Allemann, Doelker, Fessi, "Preparation and characterization of nanocapsules from preformed polymers by a new process based on emulsification-diffusion techinque," *Phamr. Res.*, 15(7):1056–1062, 1998.

Racher et al., *Biotechnology Techniques*, 9:169–174, 1995.

Ragot, Vincent, Chafey, Vigne, Gilgenkrantz, Couton, Cartaud, Briand, Kaplan, Perricaudet, Kahn, "Efficient adenovirus-mediated transfer of a human minidystrophin gene to skeletal muscle of mdx mice," *Nature* 361:647–650, 1993.

Rassoulzadegan et al., "Transmeiotic differentiation of male germ cells in culture," *Cell*, 75(5):997–1006, 1993.

Reijo et al., "Mouse autosomal homolog of DAZ, a candidate male sterility gene in humans, is expressed in male germ cells before and after puberty," *Genomics*, 35(2):346–52, 1996.

Reijo et al., "Severe oligozoospermia resulting from deletions of azoospermia factor gene on Y chromosome," *Lancet*, 347(9011):1290–3, 1996.

Reijo, Lee, Salo, Alagappan, Brown, Rosenberg, Rozen, Jaffe, Straus, Hovatta et al., "Diverse spermatogenic defects in humans caused by Y chromosome deletions encompassing a novel RNA-binding protein gene," *Nat. Genet.*, 10(4):383–393, 1995.

Reinhold-Hurek and Shub, "Self-splicing introns in tRNA genes of widely divergent bacteria," *Nature*, 357:173–176, 1992.

Renan, "Cancer genes: current status, future prospects, and applicants in radiotherapy/oncology," *Radiother. Oncol.*, 19:197–218, 1990.

Renneisen et al, "Inhibition of expression of human immunodeficiency virus-1 in vitro by antibody-targeted liposomes containing antisense RNA to the env.region," *J. Biol. Chem.*, 265(27):16337–16342, 1990.

Rich et al., "Development and analysis of recombinant adenoviruses for gene therapy of cystic fibrosis," *Hum. Gene Ther.*, 4(4):461–476, 1993.

Ridgeway, "Marmmalian expression vectors," in: *Vectors: A survey of molecular cloning vectors and their uses*, Rodriguez R L, Denhardt D T, ed., Stoneham: Butterworth, pp. 467–492, 1988.

Riou et al., "The p53 and mdm-2 genes in human testicular germ-cell tumors," *Mol. Carcinog*, 12(3):124–31, 1995.

Rippe et al., "DNA-mediated gene transfer into adult rat hepatocytes in primary culture," *Mol. Cell Biol.*, 10:689–695, 1990.

Rodgers, "Combination drug therapy in hypertension: a rational approach for the pharmacist," *J. Am. Pharm. Assoc.*, 38(4):469–479, 1998.

Rodriguez, Berchuck, Whitaker, Schlossman, Clarke-Pearson, Bast, "Epidermal growth factor receptor expression in normal ovarian epithelium and ovarian cancer. II. Relationship between receptor expression and response to epidermal growth factor" *Am. J. Obstet. Gynecol.*, 164:745–750, 1991.

Roeder, "Meiotic chromosomes: it takes two to tango," *Genes Dev.*, 11 (20):2600–21, 1997.

Roosen-Runge, "Germinal-cell loss in normal metazoan spermatogenesis," *J. Reprod. Fertil.*, 35(2):339–348, 1973.

Roosen-Runge, "Untersuchungen uber die degeneration samenbildender zellen in der normalen spermatogenese der ratte," *Z. Zellforsch. Mikrosk. Anat.*, 41:221–235, 1955.

Rose and Holm, "Meiosis-specific arrest revealed in DNA topoisomerase II mutants," *Mol. Cell Biol.*, 13(6):3445–55, 1993.

Rose, "Characterization of antisense binding properties of peptide nucleic acids by capillary gel electrophoresis," *Anal. Chem.*, 65(24):3545–3549, 1993.

Rosenfeld et al., "In vivo transfer of the human cystic fibrosis transmembrane conductance regulator gene to the airway epithelium," *Cell*, 68:143–155, 1992.

Rosenfeld, Siegfried, Yoshimura, Yoneyama, Fukayama, Stier, Paakko, Gilardi, Stratford-Perricaudet, Perricaudet, Jallat, Pavirani, Lecocq, Crystal, "Adenovirus-mediated transfer of a recombinant ∀1-antitrypsin gene to the lung epithelium in vivo, "*Science*, 252:431–434, 1991.

Rosenfeld, Yoshimura, Trapnell, Yoneyama, Rosenthal, Dalemans, Fukayama, Bargon, Stier, Stratford-Perricaudet, Perricaudet, Guggino, Pavirani, Lecocq, Crystal, "In vivo transfer of the human cystic fibrosis transmembrane conductance regulator gene to the airway epithelium," *Cell*, 68:143–155, 1992.

Rosenthal, "Drug therapy of renovascular hypertension," *Drugs*, 45(6):895–909, 1993.

Ross, Waymire, Moss, Parlow, Skinner, Russell, MacGregor, "Testicular degeneration in Bclw-deficient mice," *Nat. Genet.*, 18(3):251–256, 1998.

Rossi, Elkins, Zaia, Sullivan, "Ribozymes as anti-HIV-1 therapeutic agents: principles, applications, and problems," *AIDS Res. Hum. Retrovir.*, 8(2):183, 1992.

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses," *Proc. Natl. Acad. Sci. USA*, 86:9079–9083, 1989.

Rubin, Finstad, Wong et al., "Prognostic significance of HER-2/neu expression in advanced ovarian cancer," *Am. J. Obstet. Gynecol.*, 168:162–169, 1993.

Ruggiu, Speed, Taggart, McKay, Kilanowski, Saunders, Dorin, Cooke, "The mouse Dazla gene encodes a cytoplasmic protein essential for gametogenesis," *Nature*, 389(6646):73–77, 1997.

Rusckowski, Qu, Chang, Hnatowich, "Pretargeting using peptide nucleic acid," *Cancer*, 80(12 Suppl):2699–2705, 1997.

Russell and Clermont, "Degeneration of germ cells in normal, hypophysectomized and hormone treated hypophysectomized rats," *Anat. Rec.*, 187(3):347–66, 1977.

Sadeck, Fernandes, Silva, Trindade, Chia, Ramos, Leone, "Captopril use in pregnancy and its effects on the fetus and the newborn: case report," (Article in Portugese), *Rev. Hosp. Clin. Fac. Med. Sao Paulo*, 52(6):328–332, 1997.

Sahyoun, McDonald, Farrell, Lapetina, "Phosphorylation of a Ras-related GTP-binding protein, Rap-1b, by a neuronal Ca2+/calmodulin-dependent protein kinase, CaM kinase Gr," *Proc. Natl. Acad. Sci. USA*, 88:2643–2647, 1991.

Sakoda, Kaibuchi, Kishi, Kishida, Doi, Hoshino, Hattori, Takai, "smg/Rap1/Krev-1 p12s inhibit the signal pathway to the c-fos promoter/enhancer from c-Ki-Ras p21 but not from c-raf-1 kinase in NIH3T3 cells," *Oncogene*, 7:1705–1711, 1992.

Sambrook, Fritsch, Maniatis, In: *Molecular Cloning: A Laboratory Manual*, Cold Spring Harbor Laboratory Press, Plainview, N.Y., 1989.

Sarver, Cantin, Chang, Zaia, Ladne, Stephens, Rossi, "Ribozymes as a potential anti-HIV-1 therapeutic agents," *Science*, 247(4947):1222–1225, 1990.

Sassone-Corsi, "Transcriptional checkpoints determining the fate of male germ cells," *Cell*, 88(2):163–166, 1997.

Saville and Collins, "A site-specific self-cleavage reaction performed by a novel RNA in Neurospora mitochondria," *Cell*, 61(4):685–696, 1990.

Saville and Collins, "RNA-mediated ligation of self-cleavage products of a Neurospora mitochondrial plasmid transcript," *Proc. Natl. Acad. Sci. USA*, 88(19):8826–8830, 1991.

Scanlon, Jiao, Funato, Wang, Tone, Rossi, Kashani-Sabet, "Ribozyme-mediated cleavage of c-fos mRNA reduces gene expression of DNA synthesis enzymes and metallothionein,", *Proc. Natl. Acad. Sci. USA*, 88(23):10591–10595, 1991.

Scaringe, Francklyn, Usman, "Chemical synthesis of biologically active oligoribonucleotides using beta-cyanoethyl protected ribonucleoside phosphoramidites," *Nuc. Acids Res.*, 18(18):5433–5441, 1990.

Schemper and Stare, "Explained Variation in Survival Analysis," *Statistics in Medicine*, 15:1999–2012, 1996.

Schwab, Chavany, Duroux, Goubin, Lebeau, Helene, Saison-Behmoaras, "Antisense oligonucleotides adsorbed to polyalkylcyanoacrylate nanoparticles specifically inhibit mutated Ha-ras-mediated cell proliferation and tumorigenicity in nude mice," *Proc. Natl. Acad. Sci. USA*, 91(22):10460–10464, 1994.

Sculier et al., "Pilot study of amphotericin B entrapped in sonicated liposomes in cancer patients with flngal infections," *J. Cancer Clin. Oncol.*, 24(3):527–538, 1988.

Seboun et al., "Gene sequence, localization, and evolutionary conservation of DAZLA, a candidate male sterility gene," *Genomics*, 41(2):227–35, 1997.

Seeger, Batz, Orum, "PNA-mediated purification of PCR™ amplifiable human genomic DNA from whole blood," *Biotechniques*, 23(3):512–517, 1997.

Segal, "Biochemical Calculations" 2nd Edition. John Wiley & Sons, New York, 1976.

Shan et al., "A SPGY copy homologous to the mouse gene Dazla and the Drosophila gene boule is autosomal and expressed only in the human male gonad," *Hum. Mol. Genet.*, 5(12):2005–11, 1996.

Shikone, Billig, Hsueh, "Experimentally induced cryptorchidism increases apoptosis in rat testis," *Biol. Reprod.*, 51(5):865–72, 1994.

Shultz, Schwaitzer, Rajan, Yi, Ihle, Mathews, Thomas, Beier, "Mutations at the murine motheaten locus are within the hematopoietic cell protein-tyrosine phosphatase (Hcph) gene," *Cell*, 73(7):1445–54, 1993.

Silver, "Genetic organization of the mouse t complex," *Cell*, 27(2 Pt 1):239–40, 1981.

Simoni et al., "Screening for deletions of the Y chromosome involving the DAZ (Deleted in AZoospermia) gene in azoospermia and severe oligozoospermia," *Fertil. Steril.*, 67(3):542–7,.1997.

Simoni, "Transgenic animals in male reproduction research," *Experimental and Clinical Endocrinology*, 102(6):419–33, 1994.

Simonian, Grillot, Nunez, "Bcl-2 and Bcl-XL can differentially block chemotherapy-induced cell death," *Blood*, 90(3):1208–16, 1997.

Smith, Annau, Chandrasegaran, "Finding sequence motifs in groups of functionally related proteins," *Proc. Natl. Acad. Sci. USA*, 87(2):826–830, 1990.

Stahl, "Meiotic recombination in yeast: coronation of the double-strand-break repair model," *Cell*, 87(6):965–8, 1996.

Stallworth and Waldron, "Cortical blindness. as a complication of acute glomerulonephritis," *J.S.C. Med. Assoc.*, 93(3):99–101, 1997.

Stampfer, "Isolation and growth of human mammary epithelial cells," *J. Tissue Culture Methods*, 9:107–115, 1985.

Stec et al., *J. Am. Chem. Soc.*, 106:6077–6079, 1984.

Steel and Peckham, "Exploitable mechanisms in combined ratiotherapy-chemotherapy: The concept of additivity," *Int. J. Radiation Oncol. Biol. Phys.*, 5:85–91, 1979.

Stein et al., *Gene*, 72:333–341, 1988.

Stetsenko, Perchnko, Ivchenki, Kit, Petrova, Bahlikova, "The use of microwave resonance therapy in the health-resort treatment of peptic ulcer," *Lik Sprava*, 1–2:119–120, 1996.

Stewart et al., "Immunochemical studies on tobacco mosaic virus protein. IV. The automated solid-phase synthesis of a decapeptide of tobacco mosaic virus protein and its reaction with antibodies to the whole protein," *Biochemistry*, 5(11):3396–3400, 1966.

Stewart et al., "Studies of the expression of the Wiskott-Aldrich syndrome protein," *J. Clin. Invest.*, 97(11):2627–34, 1996.

Stratford-Perricaudet and Perricaudet," Gene transfer into animals: the promise of adenovirus," p. 51–61, In: *Human Gene Transfer*, Eds, O. Cohen-Haguenauer and M. Boiron, Editions John Libbey Eurotext, France, 1991.

Stratford-Perricaudet et al., "Evaluation of the transfer and expression in mice of an enzyme-encoding gene using a human adenovirus vector," *Hum. Gene Ther.*, 1:241–256, 1990.

Stromberg, Collins, Gordon, Jackson, Johnson, "Transforming growth factor-alpha acts as an autocrine growth factor in ovarian carcinoma cell lines," *Cancer Res.*, 52(2):341–347, 1992.

Suzuki, Shin, Fjuikura, Matsuzaki, Takata, "Direct gene transfer into rat liver cells by in vivo electroporation," *FEBS Lett.*, 425(3):436–440, 1998.

Svejstrup et al., "Different forms of TFIIH for transcription and DNA repair: holo-TFIIH and a nucleotide excision repairosome," *Cell*, 80(1):21–8, 1995.

Symmans, Liu, Knowles, Inghirami, "Breast cancer heterogeneity: evaluation of clonality in primary and metastatic lesions," *Hum. Path.*, 26:210–216, 1995.

Taira, Nakagawa, Nishikawa, Furukawa, "Construction of a novel RNA-transcript-trimming plasmid which can be used both in vitro in place of run-off and (G)-free transcriptions and in vivo as multi-sequences transcription vectors," *Nucl. Acids Res.*, 19(19):5125–5130, 1991.

Takakura, "Drug delivery systems in gene therapy," *Nippon Rinsho*, 56(3):691–695, 1998.

Takenaga, Serizawa, Azechi, Ochiai, Kosaka, Igarashi, Mizushima, "Microparticle resins as a potential nasal drug delivery system for insulin," *J. Controller Release*, 52(1–2):81–87, 1998.

Temin, "Retrovirus vectors for gene transfer: Efficient integration into and expression of exogenous DNA in vertebrate cell genome," In: *Gene Transfer*, Kucherlapati (Ed.), Plenum Press, New York, pp. 149–188, 1986.

Therneau, "A Package for Survival Analysis in S," *Mayo Foundation*, 1994.

Themeau, Grambsch, Fleming, "Martingale-based Residuals for Survival Models," *Biometrika*, 77:147–160, 1990.

Thiede, Bayerdorffer, Blasczyk, Wittig, Neubauer, "Simple and sensitive detection of mutations in the ras proto-oncogenes using PNA-mediated PCR™ clamping," *Nuc. Acids Res.*, 24(5):983–984, 1996.

Tomic, Sunjevaric, Savtchenko, Blumenberg, "A rapid and simple method for introducing specific mutations into any position of DNA leaving all other positions unaltered," *Nuc. Acids Res.*, 18(6):1656, 1990.

Top et al., "Immunization with live types 7 and 4 adenovirus vaccines. II. Antibody response and protective effect against acute respiratory disease due to adenovirus type 7," *J. Infect. Dis.*, 124:155–160, 1971.

Tomaletti and Pfeifer, "Complete and tissue-independent methylation of CpG sites in the p53 gene: implications for mutations in human cancers," *Oncogene* 10(85:1493–1499, 1995.

Toscani, Mettus, Coupland, Simpkins, Litvin, Orth, Hatton, Reddy, "Arrest of spermatogenesis and defective breast development in mice lacking A-myb," *Nature*, 386(6626):713–717, 1997.

Troiano et al., "Apoptosis and spermatogenesis: evidence from an in vivo model of testosterone withdrawal in the adult rat," *Biochem. Biophys. Res. Commun.*, 202(3):1315–21, 1994.

Truong-Le, August, Leong, "Controlled gene delivery by DNA-gelatin nanopspheres,." *Hum. Gene Ther.*, 9(12):1709–1717, 1998.

Tsai and Reed, "Using a Eukaryotic Gst Fusion Vector For Proteins Difficult to Express In *E. coli*," *Biotechniques*, 23(5):794 ff, 1997.

Tur-Kaspa et al., "Use of electroporation to introduce biologically active foreign genes into primary rat hepatocytes," *Mol. Cell Biol.*, 6:716–718, 1986.

Underhill et al., "Detection Of Numerous Y Chromosome Biallelic Polymorphisms By Denaturing High-Performance Liquid Chromatography," *Genome Research*, 7(10):996–1005, 1997. "Manipulating the Mouse Embryo: A Laboratory Manual," 2nd edition (eds., Hogan, Beddington, Costantimi and Long, Cold Spring Harbor Laboratory Press, 1994.

Upender, Raj, Weir, "Megaprimer method for in vitro mutagenesis using parallel templates," *Biotechniques*, 18:29–31, 1995.

Usman and Cedergren, "Exploiting the chemical synthesis of RNA," *Trends in Biochem. Sci.*, 17(9):334, 1992.

Usman et al., *J. Am. Chem. Soc.*, 109:7845–7854, 1987.

Van Cott, Lubon, Russell, Butler, Gwazdauskas, Knight, Drohan, Velander, "Phenotypic and genotypic stability of multiple lines of transgenic pigs expressing recombinant human protein C," *Transgenic Res.*, 6(3):203–212, 1997.

Vanbever, Fouchard, Jadoul, De Morre, Preat, Marty, "In vivo noninvasive evaluation of hairless rat skin after high-voltage pulse exposure," *Skin Parmacol. Appl. Skin Physiol.*, 11(1):23–34, 1998.

Varmus et al., "Retroviruses as mutagens: Insertion and excision of a nontransforming provirus alter the expression of a resident transforming provirus," *Cell*, 25:23–36, 1981.

Varnum, "Blind-sterile: a new mutation on chromosome 2 of the house mouse," *J. Heredity*, 74(3):206–7, 1983.

Vasanthakumar and Ahmed, "Modulation of drug resistance in a daunorubicin resistant subline with oligonucleoside methylphosphonates," *Cancer Commun.*, 1(4):225–232, 1989.

Venables, Ripley, Springer-Verlag, "Modem Applied Statistics With S-Plus," New York, 1994.

Ventura, Wang, Ragot, Perricaudet, Saragosti, *Nucl. Acids Res.*, 21(14):3249–3255, 1993.

Veselkov, Demidov, Frank-Kamenetskii, Nielsen, "PNA as a rare genome-cutter," *Nature*, 379(6562):214, 1996.

Vickers, Griffith, Ramasamy, Risen, Freier, "Inhibition of NF-kappa B specific transcriptional activation by PNA strand invasion," *Nucl. Acids Res.*, 23(15):3003–3008, 1995.

Vogelweid, Verina, Norton, Harruff, Ghetti, "Hypospermatogenesis-is the cause of infertility in the male weaver mutant mouse," *J. Neurogenet.*, 9(2):89–104, 1993.

Vogt, "Human Y chromosome deletions in Yq11 and male fertility," *Adv. Exp. Med. Biol.*, 424:17–30, 1997.

Voss et al., "Synthesis of the protected tridecapeptide (56–68) of the VH domain of mouse, myeloma immunoglobulin M603 and its reattachment to resin supports," *Int J. Pept. Protein Res.*, 22(2):204–213, 1983.

Wagner, Matteucci, Lewis, Gutierrez, Moulds, Froehler, "Antisense gene inhibition by oligonucleotides containing C-5 propyne pyrimidines," *Science*, 260(5113):1510–1513, 1993.

Wagner, Zatloukal, Cotten, Kirlappos, Mechtler, Curiel, Bimstiel, "Coupling of adenovirus to transferrin-polylysine/DNA complexes greatly enhances receptor-mediated gene delivery and expression of transfected genes," *Proc. Natl. Acad. Sci. USA*, 89(13):6099–6103, 1992.

Wagner, Zenke, Cotten, Beug, Birmstiel, "Transferrin-polycation conjugates as carriers for DNA uptake into cells," *Proc. Natl. Acad. Sci. USA*, 87:3410–3414, 1990.

Walker, Little, Nadeau, Shank, "Isothermal in vitro amplification of DNA by a restriction enzyme/DNA polymerase system," *Proc. Natl. Acad. Sci. USA*, 89(1):392–396, 1992.

Wang et al., "The RAD7, RAD 16, and RAD23 genes of *Saccharomyces cerevisiae*: requirement for transcription-independent nucleotide excision repair in vitro and interactions between the gene products," *Mol. Cell. Biol.*, 17(2):635–43, 1997.

Wang, Nielsen, Jiang, Cai, Fernandes, Grant, Ozsoz, Beglieter, Mowat, "Mismatch-sensitive hybridization detection by peptide nucleic acids immobilized on a quartz crystal microbalance," *Anal. Chem.*, 69(24):5200–5202, 1997.

Wardbailey et al., "A New Mouse Mutation Causing Male Sterility and Histoincompatibility," *Mammalian Genome*, 7(11):793–797, 1996.

Watanabe et al., "Functional equivalence of human X- and Y-encoded isoforms of ribosomal protein S4 consistent with a role in Turner syndrome," *Nature Genetics*, 4(3):268–71, 1993.

Watson et al, "A linkage map of mouse chromosome 1 using an interspecific cross segregating for the gld autoimmunity mutation," *Mamm. Genome*, 2(3):158–71, 1992.

Watson, "Fluid and electrolyte disorders in cardiovascular patients," *Nurs. Clin. North Am.*, 22(4):797–803, 1987.

Watson, et al., *Molecular Biology of the Gene*, 4th Ed., W. A. Benjamin, Inc., Menlo Park, Calif., 1987.

Webb, Toth, Poehlman, "Influence of physiological factors on the age-related increase in blood pressure in healthy men," *Exp. Gerontol.*, 31(3):341–350, 1996.

Weerasinghe, Liem, Asad, Read, Joshi, "Resistance to human immunodeficiency virus type 1 (HIV-1) infection in human CD4+ lymphocyte-derived cell lines conferred by using retroviral vectors expression an HIV-1 RNA-specific ribozyme," *J. Virol.*, 65(10):5531–5534, 1991.

Weideman et al., "Dynamic interplay of TFIIA, TBP and TATA DNA," *J. Mol Biol.*, 271(1):61–75, 1997.

Weinberg, "Positive and negative controls on cell growth," *Biochemistry*, 28:8263–8269, 1989.

White-Cooper, Alphey, Glover, "The cdc25 homologue twine is required for only some aspects of the entry into meiosis in Drosophila," *J. Cell Sci.*, 106(Pt 4):1035–44, 1993.

Wielbo, Shi, Semia, "Antisense inhibition of angiotensinogen in hepatoma cell culture is enhanced by cationic liposome delivery," *Biochem. Biophy. Research Comm.*, 232:794–799, 1997.

Wielbo, Sernia, Gyurko, Phillips, "Antisense inhibition of hypertension in the spontaneously hypertensive rat," *Hypertension*, 25(3):314–319, 1994.

Wielbo, Simon, Phillips, Toffolo, "Inhibition of hypertension by peripheral administration of antisense oligodeoxynucleotides," *Hypertension*, 28(1):147–151, 1995.

Wiener, Hurteau, Kerns, Whitaker, Conaway, Wu, Berchuck, Bast, "Overexpression of the tyrosine phosphatase PTPIB is associated with human ovarian carcinomas," *Am. J. Obstet. Gynecol.*, 170:1177–1183, 1994.

Wiener, Kassim, Yu, Mills, Bast, "Transfection of human ovarian cancer cells with the HER-2/neu receptor tyrosine kinase induces a selective increase in PTP-H1, PTP-1B, and PTP-expression," *Gynecol. Oncol.*, 61:223–240, 1996.

Williamson and Lehmann, "Germ cell development in Drosophila," *Ann. Rev. Cell Dev. Biol.*, 12:365–91, 1996.

Wilmut, Hooper, Simons, "Genetic manipulation of mammals and its application in reproductive biology," *J. Reproduction and Fertility*, 92(2):245–79, 1991.

Wolf et al., "An Integrated Family of Amino Acid Sequence Analysis Programs," *Compu. Appl. Biosci.*, 4(1):187–191, 1988.

Wolf, Bazelle, Mills, Bast, Roth, Gershenson, "Growth inhibition of human ovarian cancer cells by transfection with adenovirus-mediated p53 is independent of endogenous p53 status," *Proc. Amer. Assoc. Cancer Res.*, 37:205(A#1399), 1996.

Wong and Neumann, "Electric field mediated gene transfer," *Biochim. Biophys. Res. Commun.*, 107(2):584–587, 1982.

Wong et al., "Appearance of P-lactamase activity in animal cells upon liposome mediated gene transfer," *Gene*, 10:87–94, 1980.

Wong, Straus, Warner, "Testicular biopsy in the study of male infertility," *Arch. Pathol.*, 95(3):151–159, 1973.

Woolf, Melton, Jennings, *Proc. Natl. Acad. Sci. USA*, 89(16):7305–7309, 1992.

Wooster, Neuhausen, Mangion et al., "Localization of a breast cancer susceptibility gene, BRCA2, to chromosome 13q12–13," *Science*, 265:2088–2090, 1994.

Worsley, Ponder, Davies, "Overexpression of cyclin D1 in epithelial ovarian cancers," *Gynecol. Oncol.*, 64:189–195, 1997.

Woychik, Maas, Zeller, Vogt, Leder, "° Formins: proteins deduced from the alternative transcripts of the limb deformity gene," *Nature*, 346(6287):850–853, 1990.

Woychik, Stewart, Davis, D'Eustachio, Leder, "An inherited limb deformity created by insertional mutagenesis in a transgenic mouse," *Nature*, 318(6041):336–340, 1985.

Wu and Chiang, "Establishment of stable cell lines expressing potentially toxic proteins by tetracycline-regulated and epitope-tagging methods," *Biotechniques*, 21(4):718–22, 724–5, 1996.

Wu and Dean, "Functional significance of loops in the receptor binding domain of *Bacillus thuringiensis* CryIIIA delta-endotoxin," *J. Mol. Biol.*, 255(4):628–640, 1996.

Wu and Wang, "Sequence-selective DNA binding to the regulatory subunit of cAMP-dependent protein kinase," *J. Biol. Chem.*, 264(17):9989–9993, 1989.

Wu and Wu, "Evidence for targeted gene delivery to HepG2 hepatoma cells in vitro," *Biochemistry*, 27:887–892, 1988.

Wu and Wu, "Receptor-mediated in vitro gene transfections by a soluble DNA carrier system," *J. Biol. Chem.*, 262:4429–4432, 1987.

Wu and Wu, *Adv. Drug Delivery Rev.*, 12:159–167, 1993.

Wu et al., "Correction of accelerated autoimmune disease by early replacement of the mutated 1pr gene with the normal Fas apoptosis gene in the T cells of transgenic MRL-1pr/1pr mice," *Proc. Natl. Acad. Sci. USA*, 91(6):2344–8, 1994.

Wu, Rodabaugh, Martinez-Maza, Watson, Silberstein, Boyer, Peters, Weinberg, Berek, Bast, "Stimulation of ovarian tumor cell proliferation with monocyte products including interleukin-1, interleukin-6, and tumor necrosis factor-alpha," *Am. J. Obstet. Gynecol.*, 166:997–1007, 1992.

Xiong et al., "p21 is a universal inhibitor of cyclin kinases," *Nature*, 366:701–704, 1993.

Xu et al., "Development of two new monoclonal antibodies reactive to a surface antigen present on human ovarian epithelial cancer cells," *Cancer Res.*, 51:4012–4019, 1991.

Xu, Ashley, Brainerd, Bronson, Meyn, Baltimore, "Targeted disruption of ATM leads to growth retardation, chromosomal fragmentation during meiosis, immune defects, and thymic lymphoma," *Genes Dev.*, 10(19):2411–2422, 1996.Vogt, "Human Y chromosome deletions in Yq11 and male fertility," *Adv. Exp. Med. Biol.*, 424:17–30, 1997.

Xu, Ashley, Brainerd, Bronson, Meyn, Baltimore, "Targeted disruption of ATM leads to growth retardation, chromosomal fragmentation during meiosis, immune defects, and thymic lymphoma," *Genes Dev.*, 10(19):2411–2422, 1996.

Xu, Fang, Gaudette, Holub, Casey, Mills, "Lysophospholipids activate ovarian and breast cancer cells," *Biochem. J.*, 309:933–940. 1995.

Xu, Ramakrishnan, Daly, Soper, Berchuck, Clarke-Pearson, Bast, "Increased serum levels of macrophage colony-stimulating factor in ovarian cancer," *Am. J. Obstet. Gynecol.*, 165:1356–1362, 1991.

Xu, Rodriguez, Bae, Whitaker, Boyer, Mills, Yu, Bast, "Heregulin and anti-p185c-erb$^{B-2}$ antibodies inhibit proliferation, increase invasiveness and enhance tyrosine autophosphorylation of breast cancer cells that overexpress p185c-erb$^{B-2}$," *Proc. Amer. Assoc. Cancer Res.*, 35:38(A#225), 1994.

Xu, Yu, Boyer, Walch, Khan, Mills, Bast, "Stimulation or inhibition of ovarian cancer cell proliferation by heregulin is dependent on the ratio of HER2 to HER3 or HER4 expression," *Proc. Amer. Assoc. Cancer Res.*, 37:191(A#1305), 1996.

Yang et al., "In vivo and in vitro gene transfer to mammalian somatic cells by particle bombardment," *Proc. Nat. Acad. Sci. USA*, 87:9568–9572, 1990.

Yang, "Myocardial angiotensin II receptor expression and ischemia reperfusion injury," *Circ. Res.*, 1998.

Yang, Zhang, Davey, Mulligan, Cocking, *Plant Cell Rep*, 7:421–425, 1988.

Yatani, Quilliam, Brown, Bokoch, "Rap1A antagonizes the ability of Ras and Ras-Gap to inhibit muscarinic K+ channels," *J. Biol. Chem.*, 266:22222–22226, 1991.

Young, Rodriguez, Moser, Bast, Pizzo, Stack, "Coordinate expression of urinary-type plasminogen activator and its receptor accompanies malignant transformation of the ovarian surface epithelium," *Am. J. Obstet. Gynecol.*, 170:1285–1296, 1994.

Young, Rodriguez, Rinehart, Bast, Pizzo, Stack, "Characterization of gelatinases linked to extracellular matrix invasion in ovarian adenocarcinoma: purification of matrix metalloproteinase 2," *Gyn. Oncol.*, 62:89–99, 1996.

Yu and Chang, "Submicron polymer membrane hemoglobin nanocapsules as potential blood substitutes: preparation and characterization," *Artif. Cells Blood Substit. Immobil. Biotechnol.*, 24(3):169–183, 1996.

Yu, Henry, Xu, Harnilton, "Expression of a murine cytomegalovirus early and late protein in latently infected mice," *J. Infectious Diseases*, 172:371–379, 1995a.

Yu, Matin, Xia, Sorgi, Huang, Hung, "Liposome-mediated in vivo E1A gene transfer suppressed dissemination of ovarian cancer cells that overexpress HER-2/neu," *Oncogene*, 11(7):1383–1388, 1995b.

Yu, Ojwang, Yamada, Hampel, Rapapport, Looney, Wong-Staal, "A hairpin ribozyme inhibits expression of diverse strains of human immunodeficiency virus type 1," *Proc. Natl. Acad. Sci. USA*, 90:6340–6344, 1993.

Zambaux, Bonneaux, Gref, Maincent, Dellacherie, Alonso, Labrude, Vigneron, "Influence of experimental paparmneters on the characteristics of poly(lactic acid) nanoparticles prepared by a double emulsion method," *J. Controlled Release*, 50(1–3):31–40, 1998.

Zambrowicz et al., "Expression of a mouse Zfy-1/lacZ transgene in the somatic cells of the embryonic gonad and gern cells of the adult testis," *Development*, 120(6):1549–59, 1994.

Zelenin et al., "High-velocity mechanical DNA transfer of the chloramphenicol acetyltransferase gene into rodent liver, kidney and mammary gland cells in organ explants and in vivo," *FEBS Lett.*, 280:94–96, 1991.

Zhang, Calaf, Russo, "Allele loss and point mutation in codons 12 and 61 of the c-Ha-ras oncogene in carcinogen-transformed human breast epithelial cells," *Mol. Carcin.*, 9:46–56, 1994.

Zhou, Giordano, Durbin, McAllister, *Mol. Cell Biol.*, 10(9):4529–4537, 1990.

Ziv et al., "Recombinant ATM protein complements the cellular A-T phenotype," *Oncogene*, 15(2):159–67, 1997.

zur Muhlen, Schwarz, Mehnert, "Solid lipid nanoparticles (SLN) for controlled drug delivery—drug release and release mechanism," *Eur. J. Pharm. Biopharm.*, 45(2):149–155, 1998.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An isolated nucleic acid segment comprising a nucleic acid sequence comprising position 105 to position 2954 of SEQ ID NO:1, or the complete complement thereof.

2. An isolated nucleic acid segment comprising the sequence of SEQ ID NO: 1, or the complete complement thereof.

* * * * *

SEQUENCE LISTING

<160> NUMBER OF SEQ ID NOS: 18

<210> SEQ ID NO 1
<211> LENGTH: 3051
<212> TYPE: DNA
<213> ORGANISM: Mus musculus
<220> FEATURE:
<221> NAME/KEY: CDS
<222> LOCATION: (105)..(2954)

<400> SEQUENCE: 1

```
gcaagtgagc caggccgtac gcgtggacgt aggcgtgggc gtgggccaac agtttccggt      60
cagacatcca cgtcttctgt tgtccgcagg tggtgcctga agac atg gac aaa tat     116
                                              Met Asp Lys Tyr
                                               1 gcc ttg ctg cag agg gct aaa ctg cat ctg gat ttc atc cac gcg aat      164
Ala Leu Leu Gln Arg Ala Lys Leu His Leu Asp Phe Ile His Ala Asn
 5              10                  15                  20 tcc aca aca cac agt ttc ctc ttt gga gca ctg gct gag ttg ctg gac      212
Ser Thr Thr His Ser Phe Leu Phe Gly Ala Leu Ala Glu Leu Leu Asp
             25                  30                  35 aac gca aga gat gcc ggg gct gta aga ctc gat gtg ttt tca gtg gat      260
Asn Ala Arg Asp Ala Gly Ala Val Arg Leu Asp Val Phe Ser Val Asp
         40                  45                  50 aat gaa aca ctg cag gga gga ttc atg ttg tgt ttc ctg gat gat gga      308
Asn Glu Thr Leu Gln Gly Gly Phe Met Leu Cys Phe Leu Asp Asp Gly
     55                  60                  65 tgt ggc atg agc cct gat gaa gct tca gac gta att tac ttt gga aca      356
Cys Gly Met Ser Pro Asp Glu Ala Ser Asp Val Ile Tyr Phe Gly Thr
 70                  75                  80 tcc aag aaa cgc ttg tcg acc ttg aag ttc atc ggg caa tat ggt aac      404
Ser Lys Lys Arg Leu Ser Thr Leu Lys Phe Ile Gly Gln Tyr Gly Asn
             85                  90                  95                 100 ggg ctt aag agc ggc tcc atg aga atc ggc aaa gac tgt att ctt ttc      452
Gly Leu Lys Ser Gly Ser Met Arg Ile Gly Lys Asp Cys Ile Leu Phe
                105                 110                 115 aca aag aag gaa gag acc atg acc tgt ctg ttc ttc tct cag act ttc      500
Thr Lys Lys Glu Glu Thr Met Thr Cys Leu Phe Phe Ser Gln Thr Phe
            120                 125                 130 tgt gaa aaa gaa ggt ctc act gag gtt gta gtt cca ata cct tca tgg      548
Cys Glu Lys Glu Gly Leu Thr Glu Val Val Val Pro Ile Pro Ser Trp
        135                 140                 145 cta acg aga acc aga gag agt atc aca gat gac ccg cag aag ttc ttc      596
Leu Thr Arg Thr Arg Glu Ser Ile Thr Asp Asp Pro Gln Lys Phe Phe
    150                 155                 160 aca gaa ttg tcc atc att ttc aag tac tcc cca ttt aag acc gaa gct      644
Thr Glu Leu Ser Ile Ile Phe Lys Tyr Ser Pro Phe Lys Thr Glu Ala
165                 170                 175                 180 gaa ttg atg cag cag ttt gat atg atc tac ggg aga tgt gga act ttg      692
Glu Leu Met Gln Gln Phe Asp Met Ile Tyr Gly Arg Cys Gly Thr Leu
                185                 190                 195 ctg att att tat aac ttg aag ctg ctt agc gga gaa cca gag ttg          740
Leu Ile Ile Tyr Asn Leu Lys Leu Leu Leu Ser Gly Glu Pro Glu Leu
            200                 205                 210 gat gtt aca acc gac aaa gaa gat ata ctg atg gcc gag gct ccg gag      788
Asp Val Thr Thr Asp Lys Glu Asp Ile Leu Met Ala Glu Ala Pro Glu
        215                 220                 225 gaa att cca gag aga cgg tca ttc aga gcc tac aca gct gtt ctg tat      836
Glu Ile Pro Glu Arg Arg Ser Phe Arg Ala Tyr Thr Ala Val Leu Tyr
```

```
                 230                   235                   240
ttt gaa ccc cgg atg aaa ata ttt att cag gcc aaa aga gtt caa aca        884
Phe Glu Pro Arg Met Lys Ile Phe Ile Gln Ala Lys Arg Val Gln Thr
245                 250                 255                 260 aag cat ctg tgt tat tcc ctc tac aaa ccc aga aaa tac caa tat act        932
Lys His Leu Cys Tyr Ser Leu Tyr Lys Pro Arg Lys Tyr Gln Tyr Thr
                265                 270                 275 aca tct tct ttc aaa ggg aag ttt aaa act gaa gtt caa aag gca gaa        980
Thr Ser Ser Phe Lys Gly Lys Phe Lys Thr Glu Val Gln Lys Ala Glu
            280                 285                 290 gaa gca gta aag agg gct gaa ctc ctg ttt aaa gag gtg caa gcc aaa       1028
Glu Ala Val Lys Arg Ala Glu Leu Leu Phe Lys Glu Val Gln Ala Lys
        295                 300                 305 gta aac cag ccg gac aga att gct ttg tct tct acc cag gat gca tta       1076
Val Asn Gln Pro Asp Arg Ile Ala Leu Ser Ser Thr Gln Asp Ala Leu
    310                 315                 320 cag aaa gct ctg caa gac gtg gac aca aag cat aaa agt ctt cgc cag       1124
Gln Lys Ala Leu Gln Asp Val Asp Thr Lys His Lys Ser Leu Arg Gln
325                 330                 335                 340 aaa cag agg gcc cta agg aaa gca aga act ctc tct ctg ttc ttt gga       1172
Lys Gln Arg Ala Leu Arg Lys Ala Arg Thr Leu Ser Leu Phe Phe Gly
                345                 350                 355 gtg aac aca gaa gac caa cac caa gct gga atg ttc att tac agt aat       1220
Val Asn Thr Glu Asp Gln His Gln Ala Gly Met Phe Ile Tyr Ser Asn
            360                 365                 370 aac cga ttg atc aaa atg tac gag aag gtt ggt ccc cag ctg aaa atg       1268
Asn Arg Leu Ile Lys Met Tyr Glu Lys Val Gly Pro Gln Leu Lys Met
        375                 380                 385 aag tca tta ctt ggt gca ggt ata att gga att gtg aac ata cct ttg       1316
Lys Ser Leu Leu Gly Ala Gly Ile Ile Gly Ile Val Asn Ile Pro Leu
    390                 395                 400 gag acc atg gaa cca tcc cat aat aaa caa gaa ttc ctc aat gtc caa       1364
Glu Thr Met Glu Pro Ser His Asn Lys Gln Glu Phe Leu Asn Val Gln
405                 410                 415                 420 gaa tac aat cat cta cta aaa gtc atg gga cag tac ttg atc cag tac       1412
Glu Tyr Asn His Leu Leu Lys Val Met Gly Gln Tyr Leu Ile Gln Tyr
                425                 430                 435 tgt aag gac att ggg atc agt aat aga aac cta aca ctg ttt tgg gac       1460
Cys Lys Asp Ile Gly Ile Ser Asn Arg Asn Leu Thr Leu Phe Trp Asp
            440                 445                 450 gaa ttt aaa tat cag cat agc aaa gac aca gac agc tct ttg gaa tct       1508
Glu Phe Lys Tyr Gln His Ser Lys Asp Thr Asp Ser Ser Leu Glu Ser
        455                 460                 465 ctc caa tgg cga aga aga caa gcc atg ggt atc cca ttc atc cta caa       1556
Leu Gln Trp Arg Arg Arg Gln Ala Met Gly Ile Pro Phe Ile Leu Gln
    470                 475                 480 tgc gat ctt tgt ctc aaa tgg aga gtc ctg cct tcc tct tcc aat tac       1604
Cys Asp Leu Cys Leu Lys Trp Arg Val Leu Pro Ser Ser Ser Asn Tyr
485                 490                 495                 500 cag gaa aaa gga tta cct gac cta tgg att tgt gcc agt aat ccc aac       1652
Gln Glu Lys Gly Leu Pro Asp Leu Trp Ile Cys Ala Ser Asn Pro Asn
                505                 510                 515 aac ctg gaa aac agc tgt aac cag ata gag cgc ctg cct tct atc cca       1700
Asn Leu Glu Asn Ser Cys Asn Gln Ile Glu Arg Leu Pro Ser Ile Pro
            520                 525                 530 ctg ggc acc gtg aac aga aga cca cca tca aaa gat gag aga gag agg       1748
Leu Gly Thr Val Asn Arg Arg Pro Pro Ser Lys Asp Glu Arg Glu Arg
        535                 540                 545 caa ctt caa gag tca gtc cag aga tat cag gac aag ctg gtg gaa gcg       1796
```

```
                                                              -continued

Gln Leu Gln Glu Ser Val Gln Arg Tyr Gln Asp Lys Leu Val Glu Ala
    550                 555                 560 cag ccg cag aag tct caa ctt ata gta aca agc aag atc ccc gag ttc      1844
Gln Pro Gln Lys Ser Gln Leu Ile Val Thr Ser Lys Ile Pro Glu Phe
565                 570                 575                 580 aag tcc tcc tgc ctt tcc tca gca ctc aag gaa aaa tcc aaa ctt ggg      1892
Lys Ser Ser Cys Leu Ser Ser Ala Leu Lys Glu Lys Ser Lys Leu Gly
                585                 590                 595 aga atc cag cct tca ggg gca gac ctg act cag ggc agt ccc tca tct      1940
Arg Ile Gln Pro Ser Gly Ala Asp Leu Thr Gln Gly Ser Pro Ser Ser
            600                 605                 610 gtt aag ctt tcg ttc atg caa aga agc caa aag agg agc aca gag gat      1988
Val Lys Leu Ser Phe Met Gln Arg Ser Gln Lys Arg Ser Thr Glu Asp
        615                 620                 625 act cac tcg gac gtg gag ttc atc tgc atg acg aag att ccg aag aag      2036
Thr His Ser Asp Val Glu Phe Ile Cys Met Thr Lys Ile Pro Lys Lys
    630                 635                 640 tct gtg aag aag acc gtg aag tac ctg cag cct ggt cac gct cca gct      2084
Ser Val Lys Lys Thr Val Lys Tyr Leu Gln Pro Gly His Ala Pro Ala
645                 650                 655                 660 cta ttg gaa aac ctc aaa ctc gag gac aca gcc cag gtt tct tca cgg      2132
Leu Leu Glu Asn Leu Lys Leu Glu Asp Thr Ala Gln Val Ser Ser Arg
                665                 670                 675 gaa ata aaa aag cag cag agt gag agc ctc gtg cag gca ggc aag gca      2180
Glu Ile Lys Lys Gln Gln Ser Glu Ser Leu Val Gln Ala Gly Lys Ala
            680                 685                 690 tcc act gac gtg gct agc agc aga gat cca act gtg acc atg gtt tgg      2228
Ser Thr Asp Val Ala Ser Ser Arg Asp Pro Thr Val Thr Met Val Trp
        695                 700                 705 gat caa agc agc acc aag gtc tca ctg aaa caa gaa gaa gag gag gaa      2276
Asp Gln Ser Ser Thr Lys Val Ser Leu Lys Gln Glu Glu Glu Glu Glu
    710                 715                 720 gtt ccc ctc ata aag cca gac aaa caa gag ctg tgt gat gat act cca      2324
Val Pro Leu Ile Lys Pro Asp Lys Gln Glu Leu Cys Asp Asp Thr Pro
725                 730                 735                 740 gta gtg aaa gga aat tct tca gcg ctt cac tgg aaa agc ttg ccc ggg      2372
Val Val Lys Gly Asn Ser Ser Ala Leu His Trp Lys Ser Leu Pro Gly
                745                 750                 755 gtg caa atg gaa gat tta agt cca cgt tct gga cac aaa atc aac tct      2420
Val Gln Met Glu Asp Leu Ser Pro Arg Ser Gly His Lys Ile Asn Ser
            760                 765                 770 gtg agt ggt gac tgt cag ctg ccg gct tca cca atg cct tct caa agc      2468
Val Ser Gly Asp Cys Gln Leu Pro Ala Ser Pro Met Pro Ser Gln Ser
        775                 780                 785 atg tct gtg gaa gaa aca gca aga aaa ctg ctg tct aac tta agg gaa      2516
Met Ser Val Glu Glu Thr Ala Arg Lys Leu Leu Ser Asn Leu Arg Glu
    790                 795                 800 att ctt cta tac ttt gtt ccc gag ttt cag cta tca tca gaa ttt gag      2564
Ile Leu Leu Tyr Phe Val Pro Glu Phe Gln Leu Ser Ser Glu Phe Glu
805                 810                 815                 820 tgc aca tct gtg gaa gaa ctc ata aca aat cct gag ctg gag cga tgc      2612
Cys Thr Ser Val Glu Glu Leu Ile Thr Asn Pro Glu Leu Glu Arg Cys
                825                 830                 835 cca gag aat ata aac gaa aag cta aaa acg tgt ttc aac cag atc cag      2660
Pro Glu Asn Ile Asn Glu Lys Leu Lys Thr Cys Phe Asn Gln Ile Gln
            840                 845                 850 aat atc tac atg gct cag tat gag aaa aga ctc aag agg aaa atg cag      2708
Asn Ile Tyr Met Ala Gln Tyr Glu Lys Arg Leu Lys Arg Lys Met Gln
        855                 860                 865
```

```
tcc att gtc tat gag gca aac aga agg ggc tta ctc aac caa gtg ttt    2756
Ser Ile Val Tyr Glu Ala Asn Arg Arg Gly Leu Leu Asn Gln Val Phe
    870                 875                 880 ctg gga cag tgt gaa ctg aaa agg aag agg act gag gag aaa ctc agt    2804
Leu Gly Gln Cys Glu Leu Lys Arg Lys Arg Thr Glu Glu Lys Leu Ser
885                 890                 895                 900 gac ctt cgt gca aag ctg gcc ttg ctg ctg cag aaa ctt cag ctg ggt    2852
Asp Leu Arg Ala Lys Leu Ala Leu Leu Leu Gln Lys Leu Gln Leu Gly
                905                 910                 915 ggt cca gca gga gac ccg cag cag att gat gct tac tta gaa gat ttg    2900
Gly Pro Ala Gly Asp Pro Gln Gln Ile Asp Ala Tyr Leu Glu Asp Leu
            920                 925                 930 ctt aaa gaa gat cgg ctc ccg acc gct tta cat gaa aag tct cca gag    2948
Leu Lys Glu Asp Arg Leu Pro Thr Ala Leu His Glu Lys Ser Pro Glu
        935                 940                 945 tca gcg taagcaaaag atacagaacc ctgagagggt atctcagaag tcagaaaaga    3004
Ser Ala
    950 tgttttttct taaaccact aataaagaaa actggaaaat ccttttta               3051
```

<210> SEQ ID NO 2
<211> LENGTH: 950
<212> TYPE: PRT
<213> ORGANISM: Mus musculus

<400> SEQUENCE: 2

```
Met Asp Lys Tyr Ala Leu Leu Gln Arg Ala Lys Leu His Leu Asp Phe
1               5                   10                  15

Ile His Ala Asn Ser Thr Thr His Ser Phe Leu Phe Gly Ala Leu Ala
                20                  25                  30

Glu Leu Leu Asp Asn Ala Arg Asp Ala Gly Ala Val Arg Leu Asp Val
            35                  40                  45

Phe Ser Val Asp Asn Glu Thr Leu Gln Gly Gly Phe Met Leu Cys Phe
        50                  55                  60

Leu Asp Asp Gly Cys Gly Met Ser Pro Asp Glu Ala Ser Asp Val Ile
65                  70                  75                  80

Tyr Phe Gly Thr Ser Lys Lys Arg Leu Ser Thr Leu Lys Phe Ile Gly
                85                  90                  95

Gln Tyr Gly Asn Gly Leu Lys Ser Gly Ser Met Arg Ile Gly Lys Asp
                100                 105                 110

Cys Ile Leu Phe Thr Lys Glu Glu Thr Met Thr Cys Leu Phe Phe
            115                 120                 125

Ser Gln Thr Phe Cys Glu Lys Glu Gly Leu Thr Glu Val Val Val Pro
        130                 135                 140

Ile Pro Ser Trp Leu Thr Arg Thr Arg Glu Ser Ile Thr Asp Asp Pro
145                 150                 155                 160

Gln Lys Phe Phe Thr Glu Leu Ser Ile Ile Phe Lys Tyr Ser Pro Phe
                165                 170                 175

Lys Thr Glu Ala Glu Leu Met Gln Gln Phe Asp Met Ile Tyr Gly Arg
            180                 185                 190

Cys Gly Thr Leu Leu Ile Ile Tyr Asn Leu Lys Leu Leu Ser Gly
        195                 200                 205

Glu Pro Glu Leu Asp Val Thr Thr Asp Lys Glu Asp Ile Leu Met Ala
    210                 215                 220

Glu Ala Pro Glu Glu Ile Pro Glu Arg Arg Ser Phe Arg Ala Tyr Thr
225                 230                 235                 240
```

```
Ala Val Leu Tyr Phe Glu Pro Arg Met Lys Ile Phe Ile Gln Ala Lys
                245                 250                 255

Arg Val Gln Thr Lys His Leu Cys Tyr Ser Leu Tyr Lys Pro Arg Lys
            260                 265                 270

Tyr Gln Tyr Thr Thr Ser Ser Phe Lys Gly Lys Phe Lys Thr Glu Val
        275                 280                 285

Gln Lys Ala Glu Glu Ala Val Lys Arg Ala Glu Leu Leu Phe Lys Glu
    290                 295                 300

Val Gln Ala Lys Val Asn Gln Pro Asp Arg Ile Ala Leu Ser Ser Thr
305                 310                 315                 320

Gln Asp Ala Leu Gln Lys Ala Leu Gln Asp Val Asp Thr Lys His Lys
                325                 330                 335

Ser Leu Arg Gln Lys Gln Arg Ala Leu Arg Lys Ala Arg Thr Leu Ser
            340                 345                 350

Leu Phe Phe Gly Val Asn Thr Glu Asp Gln His Gln Ala Gly Met Phe
        355                 360                 365

Ile Tyr Ser Asn Asn Arg Leu Ile Lys Met Tyr Glu Lys Val Gly Pro
    370                 375                 380

Gln Leu Lys Met Lys Ser Leu Leu Gly Ala Gly Ile Ile Gly Ile Val
385                 390                 395                 400

Asn Ile Pro Leu Glu Thr Met Glu Pro Ser His Asn Lys Gln Glu Phe
                405                 410                 415

Leu Asn Val Gln Glu Tyr Asn His Leu Leu Lys Val Met Gly Gln Tyr
            420                 425                 430

Leu Ile Gln Tyr Cys Lys Asp Ile Gly Ile Ser Asn Arg Asn Leu Thr
        435                 440                 445

Leu Phe Trp Asp Glu Phe Lys Tyr Gln His Ser Lys Asp Thr Asp Ser
    450                 455                 460

Ser Leu Glu Ser Leu Gln Trp Arg Arg Gln Ala Met Gly Ile Pro
465                 470                 475                 480

Phe Ile Leu Gln Cys Asp Leu Cys Leu Lys Trp Arg Val Leu Pro Ser
                485                 490                 495

Ser Ser Asn Tyr Gln Glu Lys Gly Leu Pro Asp Leu Trp Ile Cys Ala
            500                 505                 510

Ser Asn Pro Asn Asn Leu Glu Asn Ser Cys Asn Gln Ile Glu Arg Leu
        515                 520                 525

Pro Ser Ile Pro Leu Gly Thr Val Asn Arg Arg Pro Pro Ser Lys Asp
    530                 535                 540

Glu Arg Glu Arg Gln Leu Gln Glu Ser Val Gln Arg Tyr Gln Asp Lys
545                 550                 555                 560

Leu Val Glu Ala Gln Pro Gln Lys Ser Gln Leu Ile Val Thr Ser Lys
                565                 570                 575

Ile Pro Glu Phe Lys Ser Ser Cys Leu Ser Ser Ala Leu Lys Glu Lys
            580                 585                 590

Ser Lys Leu Gly Arg Ile Gln Pro Ser Gly Ala Asp Leu Thr Gln Gly
        595                 600                 605

Ser Pro Ser Ser Val Lys Leu Ser Phe Met Gln Arg Ser Gln Lys Arg
    610                 615                 620

Ser Thr Glu Asp Thr His Ser Asp Val Glu Phe Ile Cys Met Thr Lys
625                 630                 635                 640

Ile Pro Lys Lys Ser Val Lys Lys Thr Val Lys Tyr Leu Gln Pro Gly
                645                 650                 655

His Ala Pro Ala Leu Leu Glu Asn Leu Lys Leu Glu Asp Thr Ala Gln
```

```
                   660                 665                 670
Val Ser Ser Arg Glu Ile Lys Lys Gln Gln Ser Glu Ser Leu Val Gln
        675                 680                 685

Ala Gly Lys Ala Ser Thr Asp Val Ala Ser Ser Arg Asp Pro Thr Val
    690                 695                 700

Thr Met Val Trp Asp Gln Ser Ser Thr Lys Val Ser Leu Lys Gln Glu
705                 710                 715                 720

Glu Glu Glu Glu Val Pro Leu Ile Lys Pro Asp Lys Gln Glu Leu Cys
                725                 730                 735

Asp Asp Thr Pro Val Val Lys Gly Asn Ser Ser Ala Leu His Trp Lys
            740                 745                 750

Ser Leu Pro Gly Val Gln Met Glu Asp Leu Ser Pro Arg Ser Gly His
        755                 760                 765

Lys Ile Asn Ser Val Ser Gly Asp Cys Gln Leu Pro Ala Ser Pro Met
    770                 775                 780

Pro Ser Gln Ser Met Ser Val Glu Glu Thr Ala Arg Lys Leu Leu Ser
785                 790                 795                 800

Asn Leu Arg Glu Ile Leu Leu Tyr Phe Val Pro Glu Phe Gln Leu Ser
                805                 810                 815

Ser Glu Phe Glu Cys Thr Ser Val Glu Glu Leu Ile Thr Asn Pro Glu
            820                 825                 830

Leu Glu Arg Cys Pro Glu Asn Ile Asn Glu Lys Leu Lys Thr Cys Phe
        835                 840                 845

Asn Gln Ile Gln Asn Ile Tyr Met Ala Gln Tyr Glu Lys Arg Leu Lys
    850                 855                 860

Arg Lys Met Gln Ser Ile Val Tyr Glu Ala Asn Arg Arg Gly Leu Leu
865                 870                 875                 880

Asn Gln Val Phe Leu Gly Gln Cys Glu Leu Lys Arg Lys Arg Thr Glu
                885                 890                 895

Glu Lys Leu Ser Asp Leu Arg Ala Lys Leu Ala Leu Leu Gln Lys
            900                 905                 910

Leu Gln Leu Gly Gly Pro Ala Gly Asp Pro Gln Gln Ile Asp Ala Tyr
        915                 920                 925

Leu Glu Asp Leu Leu Lys Glu Asp Arg Leu Pro Thr Ala Leu His Glu
    930                 935                 940

Lys Ser Pro Glu Ser Ala
945                 950

<210> SEQ ID NO 3
<211> LENGTH: 3739
<212> TYPE: DNA
<213> ORGANISM: Homo sapiens
<220> FEATURE:
<221> NAME/KEY: CDS
<222> LOCATION: (63)..(3014)

<400> SEQUENCE: 3
ggcgaacggc tgccggtcag gtgtccttgt cccttgagt tgcgcgggtc gtgttcgagg     60 gc atg gac gac agg tac cct gcg ctt cag cgg gcc cag ctg cgt ctg     107
   Met Asp Asp Arg Tyr Pro Ala Leu Gln Arg Ala Gln Leu Arg Leu
   1               5                  10                  15 gat ttc atc cac gcc aac tcc acc act cac agt ttc ctt ttt gga gca   155
Asp Phe Ile His Ala Asn Ser Thr Thr His Ser Phe Leu Phe Gly Ala
                20                  25                  30 ctg gct gaa ttg ctg gac aat gca aga gat gca ggg gct gaa aga ctt   203
Leu Ala Glu Leu Leu Asp Asn Ala Arg Asp Ala Gly Ala Glu Arg Leu
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 35  |     |     |     |     | 40  |     |     |     |     | 45  |     |      |
| gat | gtc | ttt | tca | gtg | gat | aat | gaa | aaa | ctg | cag | ggg | gga | ttc | atg | ttg | 251  |
| Asp | Val | Phe | Ser | Val | Asp | Asn | Glu | Lys | Leu | Gln | Gly | Gly | Phe | Met | Leu |      |
|     |     |     | 50  |     |     |     |     | 55  |     |     |     |     | 60  |     |     |      |
| tgt | ttc | ctg | gat | gat | gga | tgt | ggc | atg | agc | cct | gag | gaa | gct | tca | gac | 299  |
| Cys | Phe | Leu | Asp | Asp | Gly | Cys | Gly | Met | Ser | Pro | Glu | Glu | Ala | Ser | Asp |      |
|     | 65  |     |     |     |     | 70  |     |     |     |     | 75  |     |     |     |     |      |
| atc | att | tac | ttt | gga | cga | tcc | aaa | aaa | cgg | ctg | tca | acc | ttg | aag | ttc | 347  |
| Ile | Ile | Tyr | Phe | Gly | Arg | Ser | Lys | Lys | Arg | Leu | Ser | Thr | Leu | Lys | Phe |      |
| 80  |     |     |     |     | 85  |     |     |     |     | 90  |     |     |     |     | 95  |      |
| ata | ggg | caa | tac | ggc | aat | ggt | ctt | aaa | agt | ggg | tcc | atg | aga | att | gga | 395  |
| Ile | Gly | Gln | Tyr | Gly | Asn | Gly | Leu | Lys | Ser | Gly | Ser | Met | Arg | Ile | Gly |      |
|     |     |     |     | 100 |     |     |     |     | 105 |     |     |     |     | 110 |     |      |
| aaa | gac | ttt | att | ctt | ttt | acg | aag | aag | gaa | gaa | acg | atg | acc | tgt | gtg | 443  |
| Lys | Asp | Phe | Ile | Leu | Phe | Thr | Lys | Lys | Glu | Glu | Thr | Met | Thr | Cys | Val |      |
|     |     |     | 115 |     |     |     |     | 120 |     |     |     |     | 125 |     |     |      |
| ttt | ttt | tct | cag | aca | ttc | tgt | gaa | gaa | gaa | agt | ctt | agt | gag | gtt | gta | 491  |
| Phe | Phe | Ser | Gln | Thr | Phe | Cys | Glu | Glu | Glu | Ser | Leu | Ser | Glu | Val | Val |      |
|     |     | 130 |     |     |     |     | 135 |     |     |     |     | 140 |     |     |     |      |
| gtt | cca | atg | ccc | tca | tgg | tta | ata | aga | acc | aga | gaa | tct | gtc | aca | gat | 539  |
| Val | Pro | Met | Pro | Ser | Trp | Leu | Ile | Arg | Thr | Arg | Glu | Ser | Val | Thr | Asp |      |
|     | 145 |     |     |     |     | 150 |     |     |     |     | 155 |     |     |     |     |      |
| gat | ccc | cag | aaa | ttt | gca | atg | gaa | tta | tct | ata | att | tat | aaa | tac | tcc | 587  |
| Asp | Pro | Gln | Lys | Phe | Ala | Met | Glu | Leu | Ser | Ile | Ile | Tyr | Lys | Tyr | Ser |      |
| 160 |     |     |     |     | 165 |     |     |     |     | 170 |     |     |     |     | 175 |      |
| cca | ttt | aaa | act | gaa | gca | gaa | ttg | atg | cag | cag | ttt | gat | gtg | atc | tat | 635  |
| Pro | Phe | Lys | Thr | Glu | Ala | Glu | Leu | Met | Gln | Gln | Phe | Asp | Val | Ile | Tyr |      |
|     |     |     |     | 180 |     |     |     |     | 185 |     |     |     |     | 190 |     |      |
| gga | aaa | tgt | ggt | act | ttg | ctg | gtt | att | tat | aac | ttg | aag | ctt | ctg | ctt | 683  |
| Gly | Lys | Cys | Gly | Thr | Leu | Leu | Val | Ile | Tyr | Asn | Leu | Lys | Leu | Leu | Leu |      |
|     |     |     | 195 |     |     |     |     | 200 |     |     |     |     | 205 |     |     |      |
| aat | gga | gaa | cca | gag | ttg | gat | gtt | aaa | act | gac | aaa | gaa | gat | ata | ctg | 731  |
| Asn | Gly | Glu | Pro | Glu | Leu | Asp | Val | Lys | Thr | Asp | Lys | Glu | Asp | Ile | Leu |      |
|     |     | 210 |     |     |     |     | 215 |     |     |     |     | 220 |     |     |     |      |
| atg | gct | gga | gct | ctg | gag | gat | ttc | cca | gcg | agg | tgg | tca | ttc | aga | gcc | 779  |
| Met | Ala | Gly | Ala | Leu | Glu | Asp | Phe | Pro | Ala | Arg | Trp | Ser | Phe | Arg | Ala |      |
|     | 225 |     |     |     |     | 230 |     |     |     |     | 235 |     |     |     |     |      |
| tac | aca | tct | gtt | ctg | tat | ttt | aac | cca | tgg | atg | aga | ata | ttc | att | caa | 827  |
| Tyr | Thr | Ser | Val | Leu | Tyr | Phe | Asn | Pro | Trp | Met | Arg | Ile | Phe | Ile | Gln |      |
| 240 |     |     |     |     | 245 |     |     |     |     | 250 |     |     |     |     | 255 |      |
| gcc | aag | aga | gtt | aaa | act | aaa | cat | ctt | tgc | tat | tgc | ctc | tac | aga | ccc | 875  |
| Ala | Lys | Arg | Val | Lys | Thr | Lys | His | Leu | Cys | Tyr | Cys | Leu | Tyr | Arg | Pro |      |
|     |     |     |     | 260 |     |     |     |     | 265 |     |     |     |     | 270 |     |      |
| aga | aag | tat | ctt | tat | gtc | aca | tct | tct | ttt | aaa | gga | gca | ttt | aaa | gat | 923  |
| Arg | Lys | Tyr | Leu | Tyr | Val | Thr | Ser | Ser | Phe | Lys | Gly | Ala | Phe | Lys | Asp |      |
|     |     |     | 275 |     |     |     |     | 280 |     |     |     |     | 285 |     |     |      |
| gaa | gtt | aaa | aag | gca | gaa | gaa | gca | gta | aag | att | gct | gaa | tcc | ata | ttg | 971  |
| Glu | Val | Lys | Lys | Ala | Glu | Glu | Ala | Val | Lys | Ile | Ala | Glu | Ser | Ile | Leu |      |
|     |     | 290 |     |     |     |     | 295 |     |     |     |     | 300 |     |     |     |      |
| aaa | gaa | gca | caa | atc | aaa | gta | aac | cag | tgt | gac | aga | acc | tct | tta | tct | 1019 |
| Lys | Glu | Ala | Gln | Ile | Lys | Val | Asn | Gln | Cys | Asp | Arg | Thr | Ser | Leu | Ser |      |
|     | 305 |     |     |     |     | 310 |     |     |     |     | 315 |     |     |     |     |      |
| tct | gcc | aag | gat | gta | tta | cag | aga | gct | ttg | gaa | gat | gta | gaa | gca | aag | 1067 |
| Ser | Ala | Lys | Asp | Val | Leu | Gln | Arg | Ala | Leu | Glu | Asp | Val | Glu | Ala | Lys |      |
| 320 |     |     |     |     | 325 |     |     |     |     | 330 |     |     |     |     | 335 |      |
| caa | aag | aat | ctt | aaa | gag | aaa | caa | aga | gaa | tta | aaa | aca | gca | aga | acg | 1115 |
| Gln | Lys | Asn | Leu | Lys | Glu | Lys | Gln | Arg | Glu | Leu | Lys | Thr | Ala | Arg | Thr |      |
|     |     |     |     | 340 |     |     |     |     | 345 |     |     |     |     | 350 |     |      |
| ctc | tcc | ctg | ttc | tat | gga | gtg | aac | gta | gaa | aac | cga | agc | caa | gct | gga | 1163 |

-continued

```
Leu Ser Leu Phe Tyr Gly Val Asn Val Glu Asn Arg Ser Gln Ala Gly
            355                 360                 365 atg ttc att tac agt aat aac cgt ttg atc aaa atg cat gaa aaa gtg      1211
Met Phe Ile Tyr Ser Asn Asn Arg Leu Ile Lys Met His Glu Lys Val
        370                 375                 380 ggc tca cag ttg aaa ctg aag tcc tta ctt ggc gca ggc gtg gtt gga      1259
Gly Ser Gln Leu Lys Leu Lys Ser Leu Leu Gly Ala Gly Val Val Gly
    385                 390                 395 att gtt aat ata ccc ttg gag gtc atg gaa cca tcc cat aat aaa cag      1307
Ile Val Asn Ile Pro Leu Glu Val Met Glu Pro Ser His Asn Lys Gln
400                 405                 410                 415 gaa ttt ctc aat gtc caa gag tat aat cat cta cta aaa gtc atg gga      1355
Glu Phe Leu Asn Val Gln Glu Tyr Asn His Leu Leu Lys Val Met Gly
                420                 425                 430 cag tac ttg gtc cag tac tgt aag gac acc ggc atc aat aat aga aat      1403
Gln Tyr Leu Val Gln Tyr Cys Lys Asp Thr Gly Ile Asn Asn Arg Asn
            435                 440                 445 tta aca ttg ttt tgc aat gaa ttt gga tac cag aat gac atc gac gtg      1451
Leu Thr Leu Phe Cys Asn Glu Phe Gly Tyr Gln Asn Asp Ile Asp Val
        450                 455                 460 gag aaa cct tta aat tct att caa tat caa aga aga caa gcc atg ggt      1499
Glu Lys Pro Leu Asn Ser Ile Gln Tyr Gln Arg Arg Gln Ala Met Gly
    465                 470                 475 atc cca ttc atc ata caa tgt gat ctt tgt ctt aaa tgg aga gtc ttg      1547
Ile Pro Phe Ile Ile Gln Cys Asp Leu Cys Leu Lys Trp Arg Val Leu
480                 485                 490                 495 cct tcc tct act aat tat cag gaa aaa gaa ttt ttt gac att tgg att      1595
Pro Ser Ser Thr Asn Tyr Gln Glu Lys Glu Phe Phe Asp Ile Trp Ile
                500                 505                 510 tgt gct aat aat ccc aac cgc ttg gaa aac agt tgt cat cag gta gaa      1643
Cys Ala Asn Asn Pro Asn Arg Leu Glu Asn Ser Cys His Gln Val Glu
            515                 520                 525 tgt cta cct tcc atc cca ctg ggc acc atg agc aca ata tca cca tca      1691
Cys Leu Pro Ser Ile Pro Leu Gly Thr Met Ser Thr Ile Ser Pro Ser
        530                 535                 540 aaa aat gag aaa gag aag caa ctt aga gag tcg gtc ata aag tat caa      1739
Lys Asn Glu Lys Glu Lys Gln Leu Arg Glu Ser Val Ile Lys Tyr Gln
    545                 550                 555 aat aga ctg gca gaa cag cag cca cag cct caa ttt ata cca gtg gac      1787
Asn Arg Leu Ala Glu Gln Gln Pro Gln Pro Gln Phe Ile Pro Val Asp
560                 565                 570                 575 gaa atc act gtc act tcc acc tgc cta act tca gca cat aag gaa aat      1835
Glu Ile Thr Val Thr Ser Thr Cys Leu Thr Ser Ala His Lys Glu Asn
                580                 585                 590 acc aaa acc cag aaa atc agg ctt ttg ggc gat gac ttg aag cat gaa      1883
Thr Lys Thr Gln Lys Ile Arg Leu Leu Gly Asp Asp Leu Lys His Glu
            595                 600                 605 tct ctt tca tcc ttt gag ctt tca gcg agc cgt aga gga cag aaa aga      1931
Ser Leu Ser Ser Phe Glu Leu Ser Ala Ser Arg Arg Gly Gln Lys Arg
        610                 615                 620 aac ata gaa gag aca gac tct gat gta gag tat att tca gaa aca aaa      1979
Asn Ile Glu Glu Thr Asp Ser Asp Val Glu Tyr Ile Ser Glu Thr Lys
    625                 630                 635 att atg aaa aag tct atg gag gag aaa atg aac tct caa cag cag aga      2027
Ile Met Lys Lys Ser Met Glu Glu Lys Met Asn Ser Gln Gln Gln Arg
640                 645                 650                 655 att cca gta gct ctg cca gaa aat gtc aaa cta gct gag aga tcc cag      2075
Ile Pro Val Ala Leu Pro Glu Asn Val Lys Leu Ala Glu Arg Ser Gln
                660                 665                 670
```

|  |  |
|---|---|
| aga agt cag att gct aat att acc act gtc tgg aga gct caa cca act<br>Arg Ser Gln Ile Ala Asn Ile Thr Thr Val Trp Arg Ala Gln Pro Thr<br>              675                  680              685 | 2123 |
| gaa ggg tgc ctg aag aat gcc cag gcc gct tct tgg gaa atg aaa agg<br>Glu Gly Cys Leu Lys Asn Ala Gln Ala Ala Ser Trp Glu Met Lys Arg<br>        690                  695                  700 | 2171 |
| aag cag agt ctc aac ttt gta gag gaa tgt aag gta ttg act gaa gat<br>Lys Gln Ser Leu Asn Phe Val Glu Glu Cys Lys Val Leu Thr Glu Asp<br>705                  710                  715 | 2219 |
| gag aac acg agt gat tca gat ata atc ctg gtt tca gat aaa agc aac<br>Glu Asn Thr Ser Asp Ser Asp Ile Ile Leu Val Ser Asp Lys Ser Asn<br>720                  725                  730              735 | 2267 |
| act gat gtt tca ttg aaa caa gaa aaa aag gaa att cct ctt tta aac<br>Thr Asp Val Ser Leu Lys Gln Glu Lys Lys Glu Ile Pro Leu Leu Asn<br>              740                  745              750 | 2315 |
| caa gaa aaa cag gag ctg tgc aat gat gtt cta gca atg aaa aga agc<br>Gln Glu Lys Gln Glu Leu Cys Asn Asp Val Leu Ala Met Lys Arg Ser<br>        755                  760                  765 | 2363 |
| tct tca tta cct agc tgg aaa agc ttg ctc aat gtg ccg atg gaa gat<br>Ser Ser Leu Pro Ser Trp Lys Ser Leu Leu Asn Val Pro Met Glu Asp<br>770                  775                  780 | 2411 |
| gtg aat cta agt tct gga cac ata gcc aga gtt tct gtg agt ggc agt<br>Val Asn Leu Ser Ser Gly His Ile Ala Arg Val Ser Val Ser Gly Ser<br>785                  790                  795 | 2459 |
| tgt aaa gtt gct tct tcg cca gcg tct tct caa agc aca cct gtc aag<br>Cys Lys Val Ala Ser Ser Pro Ala Ser Ser Gln Ser Thr Pro Val Lys<br>800                  805                  810              815 | 2507 |
| gaa aca gtg aga aaa ctg aag tct aag tta agg gag att ctt ctg tat<br>Glu Thr Val Arg Lys Leu Lys Ser Lys Leu Arg Glu Ile Leu Leu Tyr<br>              820                  825              830 | 2555 |
| ttt ttt cct gag tat cag cta cca tca gaa ttg gaa gaa cct gca tta<br>Phe Phe Pro Glu Tyr Gln Leu Pro Ser Glu Leu Glu Glu Pro Ala Leu<br>        835                  840                  845 | 2603 |
| agt tgt gag ctg gag cag tgc cca gag cag atg aac aaa aag ctg aaa<br>Ser Cys Glu Leu Glu Gln Cys Pro Glu Gln Met Asn Lys Lys Leu Lys<br>              850                  855              860 | 2651 |
| atg tgt ttc aac cag ata cag aat act tac atg gtc caa tat gaa aaa<br>Met Cys Phe Asn Gln Ile Gln Asn Thr Tyr Met Val Gln Tyr Glu Lys<br>865                  870                  875 | 2699 |
| aaa ata aag agg aaa ttg cag tcc att atc tat gat tca aat aca aga<br>Lys Ile Lys Arg Lys Leu Gln Ser Ile Ile Tyr Asp Ser Asn Thr Arg<br>880                  885                  890              895 | 2747 |
| gga ata cat aat gaa atc tct ctg ggg caa tgt gaa aat aaa aga aaa<br>Gly Ile His Asn Glu Ile Ser Leu Gly Gln Cys Glu Asn Lys Arg Lys<br>              900                  905              910 | 2795 |
| atc tct gag gat aag ctg aag aat ctt cgt ata aaa ctg gca cta ttg<br>Ile Ser Glu Asp Lys Leu Lys Asn Leu Arg Ile Lys Leu Ala Leu Leu<br>              915                  920              925 | 2843 |
| ttg cag aaa ctc caa ctg ggt ggt cca gaa ggt gac ctg gag cag act<br>Leu Gln Lys Leu Gln Leu Gly Gly Pro Glu Gly Asp Leu Glu Gln Thr<br>        930                  935                  940 | 2891 |
| gac act tat tta gaa gct ttg ctt aaa gaa gat aat ctt ctc ttc cag<br>Asp Thr Tyr Leu Glu Ala Leu Leu Lys Glu Asp Asn Leu Leu Phe Gln<br>945                  950                  955 | 2939 |
| aac aat tta aat aaa gta act ata gat gca aga cat aga ctc cct tta<br>Asn Asn Leu Asn Lys Val Thr Ile Asp Ala Arg His Arg Leu Pro Leu<br>960                  965                  970              975 | 2987 |
| gaa aaa aat gaa aag act tcg gaa aat taagtcagag atggtattac<br>Glu Lys Asn Glu Lys Thr Ser Glu Asn<br>              980 | 3034 |

| | |
|---|---|
| cttttaaaaa atgctaataa gaaaattgga agattctttt aaaaattttt cttttttgtt | 3094 |
| gttgttactg taaagtctat tctgtttaac aataagaaat aagaaataat ttttttcaaa | 3154 |
| taagaaaatt gtgtactcta gaaatggaga ccgatttaca atttatgtat tccctaatcc | 3214 |
| aattatctaa atcttccttt tctttcagaa atattaataa tatctagagt tctctaattt | 3274 |
| tcatgtgagc tactgaaaaa aatgaaaatg tcactcaagc ttaacttttg ttattcctta | 3334 |
| aaagattgtt attgtaattt tgttattcct taaaaacatt taaaagcaga ttttttcaaa | 3394 |
| atcgatatgt gaaggactac agaatcacct cctcttgaag atattgaaaa agaaagacat | 3454 |
| tatgcccttt ctccactata gccaacactc agtcaagcag aaaatacaaa tccccccaaa | 3514 |
| actttgagac atagcttata taattttatt atttagtcat agtaaaagaa taaatctcct | 3574 |
| aagcataata tgtatacata ttacacatat gtaaaaattg ttgttttaca tttacatata | 3634 |
| cgtaaagaag tatgttttta cacttttctt gataagtgtt tttttttgtt tagaaatgtc | 3694 |
| tgaaacttta gacaaaaaca ataaaacatt taatattcat ttgat | 3739 |

<210> SEQ ID NO 4
<211> LENGTH: 984
<212> TYPE: PRT
<213> ORGANISM: Homo sapiens

<400> SEQUENCE: 4

```
Met Asp Asp Arg Tyr Pro Ala Leu Gln Arg Ala Gln Leu Arg Leu Asp
  1               5                  10                  15

Phe Ile His Ala Asn Ser Thr Thr His Ser Phe Leu Phe Gly Ala Leu
             20                  25                  30

Ala Glu Leu Leu Asp Asn Ala Arg Asp Ala Gly Ala Glu Arg Leu Asp
         35                  40                  45

Val Phe Ser Val Asp Asn Glu Lys Leu Gln Gly Gly Phe Met Leu Cys
     50                  55                  60

Phe Leu Asp Asp Gly Cys Gly Met Ser Pro Glu Glu Ala Ser Asp Ile
 65                  70                  75                  80

Ile Tyr Phe Gly Arg Ser Lys Lys Arg Leu Ser Thr Leu Lys Phe Ile
                 85                  90                  95

Gly Gln Tyr Gly Asn Gly Leu Lys Ser Gly Ser Met Arg Ile Gly Lys
            100                 105                 110

Asp Phe Ile Leu Phe Thr Lys Lys Glu Glu Thr Met Thr Cys Val Phe
        115                 120                 125

Phe Ser Gln Thr Phe Cys Glu Glu Ser Leu Ser Glu Val Val Val
    130                 135                 140

Pro Met Pro Ser Trp Leu Ile Arg Thr Arg Glu Ser Val Thr Asp Asp
145                 150                 155                 160

Pro Gln Lys Phe Ala Met Glu Leu Ser Ile Ile Tyr Lys Tyr Ser Pro
                165                 170                 175

Phe Lys Thr Glu Ala Glu Leu Met Gln Gln Phe Asp Val Ile Tyr Gly
            180                 185                 190

Lys Cys Gly Thr Leu Leu Val Ile Tyr Asn Leu Lys Leu Leu Leu Asn
        195                 200                 205

Gly Glu Pro Glu Leu Asp Val Lys Thr Asp Lys Glu Asp Ile Leu Met
    210                 215                 220

Ala Gly Ala Leu Glu Asp Phe Pro Ala Arg Trp Ser Phe Arg Ala Tyr
225                 230                 235                 240

Thr Ser Val Leu Tyr Phe Asn Pro Trp Met Arg Ile Phe Ile Gln Ala
```

-continued

```
                        245                 250                 255
Lys Arg Val Lys Thr Lys His Leu Cys Tyr Cys Leu Tyr Arg Pro Arg
                260                 265                 270
Lys Tyr Leu Tyr Val Thr Ser Ser Phe Lys Gly Ala Phe Lys Asp Glu
            275                 280                 285
Val Lys Lys Ala Glu Ala Val Lys Ile Ala Glu Ser Ile Leu Lys
        290                 295                 300
Glu Ala Gln Ile Lys Val Asn Gln Cys Asp Arg Thr Ser Leu Ser Ser
305                 310                 315                 320
Ala Lys Asp Val Leu Gln Arg Ala Leu Glu Asp Val Glu Ala Lys Gln
                325                 330                 335
Lys Asn Leu Lys Glu Lys Gln Arg Glu Leu Lys Thr Ala Arg Thr Leu
                340                 345                 350
Ser Leu Phe Tyr Gly Val Asn Val Glu Asn Arg Ser Gln Ala Gly Met
                355                 360                 365
Phe Ile Tyr Ser Asn Asn Arg Leu Ile Lys Met His Glu Lys Val Gly
    370                 375                 380
Ser Gln Leu Lys Leu Lys Ser Leu Leu Gly Ala Gly Val Val Gly Ile
385                 390                 395                 400
Val Asn Ile Pro Leu Glu Val Met Glu Pro Ser His Asn Lys Gln Glu
                405                 410                 415
Phe Leu Asn Val Gln Glu Tyr Asn His Leu Leu Lys Val Met Gly Gln
                420                 425                 430
Tyr Leu Val Gln Tyr Cys Lys Asp Thr Gly Ile Asn Asn Arg Asn Leu
            435                 440                 445
Thr Leu Phe Cys Asn Glu Phe Gly Tyr Gln Asn Asp Ile Asp Val Glu
        450                 455                 460
Lys Pro Leu Asn Ser Ile Gln Tyr Gln Arg Arg Gln Ala Met Gly Ile
465                 470                 475                 480
Pro Phe Ile Ile Gln Cys Asp Leu Cys Leu Lys Trp Arg Val Leu Pro
                485                 490                 495
Ser Ser Thr Asn Tyr Gln Glu Lys Glu Phe Phe Asp Ile Trp Ile Cys
            500                 505                 510
Ala Asn Asn Pro Asn Arg Leu Glu Asn Ser Cys His Gln Val Glu Cys
        515                 520                 525
Leu Pro Ser Ile Pro Leu Gly Thr Met Ser Thr Ile Ser Pro Ser Lys
530                 535                 540
Asn Glu Lys Glu Lys Gln Leu Arg Glu Ser Val Ile Lys Tyr Gln Asn
545                 550                 555                 560
Arg Leu Ala Glu Gln Gln Pro Gln Pro Gln Phe Ile Pro Val Asp Glu
                565                 570                 575
Ile Thr Val Thr Ser Thr Cys Leu Thr Ser Ala His Lys Glu Asn Thr
            580                 585                 590
Lys Thr Gln Lys Ile Arg Leu Leu Gly Asp Asp Leu Lys His Glu Ser
        595                 600                 605
Leu Ser Ser Phe Glu Leu Ser Ala Ser Arg Arg Gly Gln Lys Arg Asn
    610                 615                 620
Ile Glu Glu Thr Asp Ser Asp Val Glu Tyr Ile Ser Glu Thr Lys Ile
625                 630                 635                 640
Met Lys Lys Ser Met Glu Glu Lys Met Asn Ser Gln Gln Arg Ile
                645                 650                 655
Pro Val Ala Leu Pro Glu Asn Val Lys Leu Ala Glu Arg Ser Gln Arg
                660                 665                 670
```

```
Ser Gln Ile Ala Asn Ile Thr Thr Val Trp Arg Ala Gln Pro Thr Glu
            675                 680                 685

Gly Cys Leu Lys Asn Ala Gln Ala Ala Ser Trp Glu Met Lys Arg Lys
    690                 695                 700

Gln Ser Leu Asn Phe Val Glu Glu Cys Lys Val Leu Thr Glu Asp Glu
705                 710                 715                 720

Asn Thr Ser Asp Ser Asp Ile Ile Leu Val Ser Asp Lys Ser Asn Thr
                725                 730                 735

Asp Val Ser Leu Lys Gln Glu Lys Lys Glu Ile Pro Leu Leu Asn Gln
            740                 745                 750

Glu Lys Gln Glu Leu Cys Asn Asp Val Leu Ala Met Lys Arg Ser Ser
        755                 760                 765

Ser Leu Pro Ser Trp Lys Ser Leu Leu Asn Val Pro Met Glu Asp Val
770                 775                 780

Asn Leu Ser Ser Gly His Ile Ala Arg Val Ser Val Ser Gly Ser Cys
785                 790                 795                 800

Lys Val Ala Ser Ser Pro Ala Ser Ser Gln Ser Thr Pro Val Lys Glu
                805                 810                 815

Thr Val Arg Lys Leu Lys Ser Lys Leu Arg Glu Ile Leu Leu Tyr Phe
            820                 825                 830

Phe Pro Glu Tyr Gln Leu Pro Ser Glu Leu Glu Glu Pro Ala Leu Ser
        835                 840                 845

Cys Glu Leu Glu Gln Cys Pro Gly Gln Met Asn Lys Lys Leu Lys Met
    850                 855                 860

Cys Phe Asn Gln Ile Gln Asn Thr Tyr Met Val Gln Tyr Glu Lys Lys
865                 870                 875                 880

Ile Lys Arg Lys Leu Gln Ser Ile Ile Tyr Asp Ser Asn Thr Arg Gly
                885                 890                 895

Ile His Asn Glu Ile Ser Leu Gly Gln Cys Glu Asn Lys Arg Lys Ile
            900                 905                 910

Ser Glu Asp Lys Leu Lys Asn Leu Arg Ile Lys Leu Ala Leu Leu Leu
        915                 920                 925

Gln Lys Leu Gln Leu Gly Gly Pro Glu Gly Asp Leu Glu Gln Thr Asp
930                 935                 940

Thr Tyr Leu Glu Ala Leu Leu Lys Glu Asp Asn Leu Leu Phe Gln Asn
945                 950                 955                 960

Asn Leu Asn Lys Val Thr Ile Asp Ala Arg His Arg Leu Pro Leu Glu
                965                 970                 975

Lys Asn Glu Lys Thr Ser Glu Asn
            980

<210> SEQ ID NO 5
<211> LENGTH: 59
<212> TYPE: DNA
<213> ORGANISM: Artificial Sequence
<220> FEATURE:
<223> OTHER INFORMATION: Description of Artificial Sequence: This is an
      oligonucleotide primer.

<400> SEQUENCE: 5
ggaaccctta atataacttc gtataatgta tgctatacga agttattagg tccctcgac         59

<210> SEQ ID NO 6
<211> LENGTH: 24
<212> TYPE: DNA
<213> ORGANISM: Artificial Sequence
```

```
<220> FEATURE:
<223> OTHER INFORMATION: Description of Artificial Sequence:  This is an
      oligonucleotide primer.

<400> SEQUENCE: 6
agttagccgt tattagtgga gagg                                               24

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:  This is an
      oligonucleotide primer.

<400> SEQUENCE: 7
aacttgtaac tcaggctaca t                                                  21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:  This is an
      oligonucleotide primer.

<400> SEQUENCE: 8
ggttggcttc aaattcatgg t                                                  21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:  This is an
      oligonucleotide primer.

<400> SEQUENCE: 9
catggaggtg tgagctaggt g                                                  21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:  This is an
      oligonucleotide primer.

<400> SEQUENCE: 10
cgtgggcgtg ggccaacagt t                                                  21

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence:  This is an
      oligonucleotide primer.

<400> SEQUENCE: 11
atggggagta cttgaaaatg atggac                                             26

<210> SEQ ID NO 12
<211> LENGTH: 23
<212> TYPE: DNA
<213> ORGANISM: Artificial Sequence
<220> FEATURE:
```

<223> OTHER INFORMATION: :

<400> SEQUENCE: 12
agatgccggg gctgtaagac tcg    23

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: This is an
      oligonucleotide primer.

<400> SEQUENCE: 13
ttcatccggg gttcaaaata caga    24

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: This is an
      oligonucleotide primer.

<400> SEQUENCE: 14
aagcgcagcc gcagaagtct caact    25

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: This is an
      oligonucleotide primer.

<400> SEQUENCE: 15
gccggcagct gacagtcacc actc    24

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: This is an
      oligonucleotide primer.

<400> SEQUENCE: 16
cttcttcgcc agcgtcttct ca    22

<210> SEQ ID NO 17
<211> LENGTH: 21
<212> TYPE: PRT
<213> ORGANISM: Artificial Sequence
<220> FEATURE:
<223> OTHER INFORMATION: Description of Artificial Sequence: This is an
      immunogenic peptide.

<400> SEQUENCE: 17

Asp Lys Tyr Ala Leu Leu Gln Arg Ala Lys Leu His Leu Asp Phe Ile
 1               5                  10                  15

His Ala Gly Gly Cys
            20

<210> SEQ ID NO 18
<211> LENGTH: 20
<212> TYPE: PRT

-continued

```
<213> ORGANISM: Artificial Sequence
<220> FEATURE:
<223> OTHER INFORMATION: Description of Artificial Sequence:  This is an
      immunogenic peptide.

<400> SEQUENCE: 18

Cys Gly Gly Lys Glu Asp Arg Leu Pro Thr Ala Leu His Glu Lys Ser
  1               5                  10                  15

Pro Glu Ser Ala
            20
```